(12) United States Patent
Allen et al.

(10) Patent No.: US 12,247,200 B2
(45) Date of Patent: Mar. 11, 2025

(54) COMPOSITIONS AND METHODS FOR GENERATING MASSIVELY PARALLEL NUCLEIC ACID SEQUENCING LIBRARIES

(71) Applicant: BIOO Scientific Corporation, Austin, TX (US)

(72) Inventors: Kevin D. Allen, Austin, TX (US); Kerry Gunning, Austin, TX (US)

(73) Assignee: BIOO Scientific Corporation, Austin, TX (US)

( * ) Notice: Subject to any disclaimer, the term of this patent is extended or adjusted under 35 U.S.C. 154(b) by 838 days.

(21) Appl. No.: 17/181,947

(22) Filed: Feb. 22, 2021

(65) Prior Publication Data

US 2021/0261952 A1 Aug. 26, 2021

Related U.S. Application Data

(60) Provisional application No. 63/018,712, filed on May 1, 2020, provisional application No. 62/979,697, filed on Feb. 21, 2020.

(51) Int. Cl.
*C12N 15/10* (2006.01)
*C12Q 1/6876* (2018.01)

(52) U.S. Cl.
CPC ....... *C12N 15/1093* (2013.01); *C12Q 1/6876* (2013.01)

(58) Field of Classification Search
None
See application file for complete search history.

(56) References Cited

U.S. PATENT DOCUMENTS 9,677,130 B2   6/2017   Wang et al.

FOREIGN PATENT DOCUMENTS

CA          2271256 A1 * 11/1999 ......... C12N 15/1096

OTHER PUBLICATIONS

Jacobsen et al., Direct Isolation of Poly(A)+ RNA from 4 M Guanidine Thiocyanate-Lysed Cell Extracts Using Locked Nucleic Acid-Oligo(T) Capture, 2004, Nucleic Acids Research, vol. 32, No. 7, 1-10 (Year: 2004).*
Collins, J. et al., High-throughput and quantitative genome-wide messenger RNA sequencing for molecular phenotyping. BMC Genomics, Biomed Central, 16(1):578, Aug. 5, 2015, 13 pages.
Jacobsen, N. et al., Direct Isolation of Poly(A)+ RNA From 4 M Guanidine Thiocyanate-Lysed Cell Extracts Using Locked Nucleic Acid-Oligo(T) Capture, Nucleic Acids Research, Oxford University Press, GB, 32(7): E64, Apr. 19, 2004, 10 pages.
Jordan-Starck, T. et al., Mouse apolipoprotein J: Characterization of a gene implicated in atherosclerosis, Journal of Lipid Research, American Society for Biochemistry and Molecular Biology, Inc., US, 35(2): 194-210, Feb. 1994.
Perez-Perri, J. et al., Discovery of RNA-binding proteins and characterization of their dynamic responses by enhanced RNA interactome capture, Nature Communications, 9(1): 1-13, Dec. 1, 2018.
Zhang, B. et al., Allelic reprogramming of the histone modification H3K4me3 in early mammalian development, Nature, 537(7621): 553-557, Sep. 14, 2016.
International Preliminary Report on Patentability for PCT Application No. PCT/US2021/019094 mailed Sep. 1, 2022, 8 pages.

* cited by examiner

*Primary Examiner* — Nancy J Leith
*Assistant Examiner* — Jessica D Parisi
(74) *Attorney, Agent, or Firm* — Julie K. Staple; Dinsmore & Shohl LLP

(57) ABSTRACT

Oligonucleotide primers and methods of use in producing sequencing libraries are provided according to aspects of the present disclosure which include, from 5' to 3', a homopolymer-hybridizing region, and an anchor region comprising 5'-$(\lambda)_n N_m$-3', wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements, wherein X is any nucleotide or nucleotide analog with the proviso that $\lambda$ is not a nucleotide or nucleotide analog complementary to a complementary element of the complementary homopolymer tract, and wherein N is any nucleotide or nucleotide analog.

8 Claims, 7 Drawing Sheets

Specification includes a Sequence Listing.

SEQUENCE LISTING

```
<160> NUMBER OF SEQ ID NOS: 41

<210> SEQ ID NO 1
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(10)
<223> OTHER INFORMATION: n is nucleotide analog 5-hydroxybutynl-2'-
      deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 1
nnnnnnnnnn nn                                                         12

<210> SEQ ID NO 2
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(9)
<223> OTHER INFORMATION: n is nucleotide analog 5-hydroxybutynl-2'-
      deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 2
nnnnnnnnnt nn                                                         12
```

```
<210> SEQ ID NO 3
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(8)
<223> OTHER INFORMATION: n is nucleotide analog propynyl-deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 3
nnnnnnnntt nn                                                            12

<210> SEQ ID NO 4
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(7)
<223> OTHER INFORMATION: n is nucleotide analog propynyl-deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 4
nnnnnnnttt nn                                                            12

<210> SEQ ID NO 5
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(5)
<223> OTHER INFORMATION: n is nucleotide analog propynyl-deoxyuridine
<220> FEATURE:
<221> NAME/KEY: misc_feature
<222> LOCATION: (7)..(7)
<223> OTHER INFORMATION: n is nucleotide analog propynyl-deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 5
```
nnnnntnttt nn                                                            12

<210> SEQ ID NO 6
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(6)
<223> OTHER INFORMATION: n is nucleotide analog propynyl-deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 6
nnnnnntttt nn                                                            12

<210> SEQ ID NO 7
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(10)
<223> OTHER INFORMATION: n is nucleotide analog propynyl-deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 7
nnnnnnnnnn nn                                                            12

<210> SEQ ID NO 8
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(9)
<223> OTHER INFORMATION: n is nucleotide analog propynyl-deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 8
nnnnnnnnnt nn                                                            12

<210> SEQ ID NO 9
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(2)
<223> OTHER INFORMATION: n is nucleotide analog propynyl-deoxyuridine
<220> FEATURE:
<221> NAME/KEY: misc_feature
<222> LOCATION: (4)..(5)
<223> OTHER INFORMATION: n is nucleotide analog propynyl-deoxyuridine
<220> FEATURE:
<221> NAME/KEY: misc_feature
<222> LOCATION: (7)..(8)
<223> OTHER INFORMATION: n is nucleotide analog propynyl-deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 9
nntnntnntt nn                                                         12

<210> SEQ ID NO 10
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(8)
<223> OTHER INFORMATION: n is nucleotide analog 5-hydroxybutynl-2'-
      deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 10
nnnnnnnntt nn                                                         12

<210> SEQ ID NO 11
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(7)
<223> OTHER INFORMATION: n is nucleotide analog 5-hydroxybutynl-2'-
      deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog

```
       complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 11
nnnnnnnttt nn                                                            12

<210> SEQ ID NO 12
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(2)
<223> OTHER INFORMATION: n is nucleotide analog 5-hydroxybutynl-2'-
       deoxyuridine
<220> FEATURE:
<221> NAME/KEY: misc_feature
<222> LOCATION: (4)..(5)
<223> OTHER INFORMATION: n is nucleotide analog 5-hydroxybutynl-2'-
       deoxyuridine
<220> FEATURE:
<221> NAME/KEY: misc_feature
<222> LOCATION: (7)..(8)
<223> OTHER INFORMATION: n is nucleotide analog 5-hydroxybutynl-2'-
       deoxyuridine
<220> FEATURE:
<221> NAME/KEY: misc_feature
<222> LOCATION: (11)..(11)
<223> OTHER INFORMATION: n is any nucleotide or nucleotide analog with
       the proviso that n is not a nucleotide or nucleotide analog
       complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 12
nntnntnntt nn                                                            12

<210> SEQ ID NO 13
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(6)
<223> OTHER INFORMATION: n is nucleotide analog 5-hydroxybutynl-2'-
       deoxyuridine
<220> FEATURE:
<221> NAME/KEY: misc_feature
<222> LOCATION: (11)..(11)
<223> OTHER INFORMATION: n is any nucleotide or nucleotide analog with
       the proviso that n is not a nucleotide or nucleotide analog
       complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 13
nnnnnntttt nn                                                            12

<210> SEQ ID NO 14
<211> LENGTH: 12
<212> TYPE: DNA
<213> ORGANISM: Artificial Sequence
```

```
<220> FEATURE:
<223> OTHER INFORMATION: Oligonucleotide Primer
<220> FEATURE:
<221> NAME/KEY: misc_feature
<222> LOCATION: (1)..(5)
<223> OTHER INFORMATION: n is nucleotide analog 5-hydroxybutynl-2'-
      deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 14 nnnnntttttt nn                                                          12

<210> SEQ ID NO 15
<211> LENGTH: 12
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(4)
<223> OTHER INFORMATION: n is nucleotide analog 5-hydroxybutynl-2'-
      deoxyuridine
<220> FEATURE:
<221> NAME/KEY: misc_feature
<222> LOCATION: (11)..(11)
<223> OTHER INFORMATION: n is any nucleotide or nucleotide analog with
      the proviso that n is not a nucleotide or nucleotide analog
      complementary to A
<220> FEATURE:
<221> NAME/KEY: misc_feature
<222> LOCATION: (12)..(12)
<223> OTHER INFORMATION: n is any nucleotide or nucleotide analog

<400> SEQUENCE: 15
nnnntttttt nn                                                           12

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (22)..(22)
<223> OTHER INFORMATION: n is any nucleotide or nucleotide analog

<400> SEQUENCE: 16
tttttttttt tttttttttt vn                                                22

<210> SEQ ID NO 17
<211> LENGTH: 42
<212> TYPE: DNA
<213> ORGANISM: Artificial Sequence
<220> FEATURE:
<223> OTHER INFORMATION: Sequencing Library Adapter Oligonucleotide
<220> FEATURE:
<221> NAME/KEY: modified_base
<222> LOCATION: (1)..(1)
<223> OTHER INFORMATION: dideoxynucleotide
<220> FEATURE:
<221> NAME/KEY: misc_feature
<222> LOCATION: (1)..(1)
```

```
<223> OTHER INFORMATION: n is a, c, g, t or u
<220> FEATURE:
<221> NAME/KEY: misc_feature
<222> LOCATION: (39)..(42)
<223> OTHER INFORMATION: n is a, c, g, t or u

<400> SEQUENCE: 17
nvtttttttt ttguucagag uucuacaguc cgacgaucnn nn                 42

<210> SEQ ID NO 18
<211> LENGTH: 65
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (25)..(32)
<223> OTHER INFORMATION: n is a, c, g, or t

<400> SEQUENCE: 18
caagcagaag acggcatacg agatnnnnnn nngtgactgg agttccttgg cacccgagaa    60
ttcca                                                               65

<210> SEQ ID NO 19
<211> LENGTH: 63
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (30)..(37)
<223> OTHER INFORMATION: n is a, c, g, or t

<400> SEQUENCE: 19
aatgatacgg cgaccaccga gatctacacn nnnnnnnaca cgttcagagt tctacagtcc    60 gav                                                                 63

<210> SEQ ID NO 20
<211> LENGTH: 73
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (25)..(47)
<223> OTHER INFORMATION: n is a, c, g, or t

<400> SEQUENCE: 20
tccttggcac ccgagaattc catvnnnnnn nnnnnnnnnn nnnnnngat cgtcggactg     60 tagaactctg aac                                                      73

<210> SEQ ID NO 21
<211> LENGTH: 65
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (25)..(32)
<223> OTHER INFORMATION: n is a, c, g, or t

<400> SEQUENCE: 21
caagcagaag acggcatacg agatnnnnnn nngtgactgg agttccttgg cacccgagaa    60
``` ttcca 65

<210> SEQ ID NO 22
<211> LENGTH: 62
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (30)..(37)
<223> OTHER INFORMATION: n is a, c, g, or t

<400> SEQUENCE: 22
aatgatacgg cgaccaccga gatctacacn nnnnnnaca cgttcagagt tctacagtcc   60
ga                                                                 62

<210> SEQ ID NO 23
<211> LENGTH: 157
<212> TYPE: DNA
<213> ORGANISM: Artificial Sequence
<220> FEATURE:
<223> OTHER INFORMATION: Sequencing Library Oligonucleotide
<220> FEATURE:
<221> NAME/KEY: misc_feature
<222> LOCATION: (30)..(37)
<223> OTHER INFORMATION: n is a, c, g, or t
<220> FEATURE:
<221> NAME/KEY: misc_feature
<222> LOCATION: (68)..(90)
<223> OTHER INFORMATION: n is a, c, g, or t
<220> FEATURE:
<221> NAME/KEY: misc_feature
<222> LOCATION: (126)..(133)
<223> OTHER INFORMATION: n is a, c, g, or t

<400> SEQUENCE: 23
aatgatacgg cgaccaccga gatctacacn nnnnnnaca cgttcagagt tctacagtcc   60
gacgatcnnn nnnnnnnnn nnnnnnnnnn batggaattc tcgggtgcca aggaactcca  120
gtcacnnnnn nnnatctcgt atgccgtctt ctgcttg                          157

<210> SEQ ID NO 24
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(32)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 24
tccttggcac ccgagaattc cannnnnnnn nnvn                              34

<210> SEQ ID NO 25
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(31)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 25
tccttggcac ccgagaattc cannnnnnnn ntvn                              34

<210> SEQ ID NO 26
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(30)
<223> OTHER INFORMATION: n is nucleotide analog propynyl-deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 26
tccttggcac ccgagaattc cannnnnnnn ttvn                              34

<210> SEQ ID NO 27
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(29)
<223> OTHER INFORMATION: n is nucleotide analog propynyl-deoxyuridine
<220> FEATURE:
<221> NAME/KEY: misc_feature
<222> LOCATION: (23)..(29)
<223> OTHER INFORMATION: n is nucleotide analog propynyl-deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 27
tccttggcac ccgagaattc cannnnnnnt ttvn                              34

<210> SEQ ID NO 28
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(27)
<223> OTHER INFORMATION: n is nucleotide analog propynyl-deoxyuridine
<220> FEATURE:
<221> NAME/KEY: misc_feature
<222> LOCATION: (29)..(29)
<223> OTHER INFORMATION: n is nucleotide analog propynyl-deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 28
tccttggcac ccgagaattc cannnnntnt ttvn                              34

<210> SEQ ID NO 29
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(28)
<223> OTHER INFORMATION: n is nucleotide analog propynyl-deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 29
tccttggcac ccgagaattc cannnnnntt ttvn        34

<210> SEQ ID NO 30
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(32)
<223> OTHER INFORMATION: n is nucleotide analog propynyl-deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 30
tccttggcac ccgagaattc cannnnnnnn nnvn        34

<210> SEQ ID NO 31
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(31)
<223> OTHER INFORMATION: n is nucleotide analog propynyl-deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 31
tccttggcac ccgagaattc cannnnnnnn ntvn        34

<210> SEQ ID NO 32
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(24)
<223> OTHER INFORMATION: n is nucleotide analog propynyl-deoxyuridine
<220> FEATURE:
<221> NAME/KEY: misc_feature
<222> LOCATION: (26)..(27)
<223> OTHER INFORMATION: n is nucleotide analog propynyl-deoxyuridine
<220> FEATURE:
<221> NAME/KEY: misc_feature
<222> LOCATION: (29)..(30)

<223> OTHER INFORMATION: n is nucleotide analog propynyl-deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 32
tccttggcac ccgagaattc canntnntnn ttvn                              34

<210> SEQ ID NO 33
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(30)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 33
tccttggcac ccgagaattc cannnnnnnn ttvn                              34

<210> SEQ ID NO 34
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(29)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 34
tccttggcac ccgagaattc cannnnnnnt ttvn                              34

<210> SEQ ID NO 35
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(24)
<223> OTHER INFORMATION: n is nucleotide analog 5-hydroxybutynl-2'-
      deoxyuridine
<220> FEATURE:
<221> NAME/KEY: misc_feature
<222> LOCATION: (26)..(27)
<223> OTHER INFORMATION: n is nucleotide analog 5-hydroxybutynl-2'-
      deoxyuridine
<220> FEATURE:
<221> NAME/KEY: misc_feature
<222> LOCATION: (29)..(30)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

```
<400> SEQUENCE: 35
tccttggcac ccgagaattc canntnntnn ttvn                              34

<210> SEQ ID NO 36
<211> LENGTH: 44
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (44)..(44)
<223> OTHER INFORMATION: n is a, c, g, or t

<400> SEQUENCE: 36
tccttggcac ccgagaattc cattttttt ttttttttt ttvn                     44

<210> SEQ ID NO 37
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (34)..(34)
<223> OTHER INFORMATION: n is a, g, c, t, or u

<400> SEQUENCE: 37
tccttggcac ccgagaattc cattttttt ttvn                               34

<210> SEQ ID NO 38
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(28)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 38
tccttggcac ccgagaattc cannnnnntt ttvn                              34

<210> SEQ ID NO 39
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(27)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 39
tccttggcac ccgagaattc cannnnnttt ttvn                              34
```

```
<210> SEQ ID NO 40
<211> LENGTH: 34
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (23)..(26)
<223> OTHER INFORMATION: n is nucleotide analog 5-hydroxybutynl-2'-
      deoxyuridine
<220> FEATURE:
<221> NAME/KEY: misc_feature
<222> LOCATION: (34)..(34)
<223> OTHER INFORMATION: n is a, g, c, t, or u

<400> SEQUENCE: 40
tccttggcac ccgagaattc cannnntttt ttvn                              34

<210> SEQ ID NO 41
<211> LENGTH: 22
<212> TYPE: DNA
<213> ORGANISM: Artificial Sequence
<220> FEATURE:
<223> OTHER INFORMATION: 5' primer tag sequence

<400> SEQUENCE: 41
tccttggcac ccgagaattc ca                                           22
```

COMPOSITIONS AND METHODS FOR GENERATING MASSIVELY PARALLEL NUCLEIC ACID SEQUENCING LIBRARIES

REFERENCE TO RELATED APPLICATIONS

This application claims priority to U.S. Provisional Patent Application Serial Nos. 62/979,697, filed Feb. 21, 2020 and 63/018,712, filed May 1, 2020. The entire content of both of which is incorporated herein by reference.

SEQUENCE LISTING

The instant application contains a Sequence Listing which has been submitted electronically as an ASCII text file and is hereby incorporated by reference in its entirety. Said ASCII text file, created on Apr. 25, 2021, is named 16NEN26902PA_ST25.txt and is 19,978 bytes in size.

FIELD OF THE INVENTION

The present disclosure pertains generally to the field of nucleic acid sequencing. In specific aspects, the present disclosure describes compositions and methods for generating massively parallel nucleic acid sequencing libraries.

BACKGROUND OF THE INVENTION

Current methods of generating nucleic acid sequencing libraries from target RNA require addition of a poly(A) tail of indeterminate length to target RNA molecules. Following reverse transcription and PCR, a sequencing library generated from such material will typically have a poly(A) stretch of 100 or more nucleotides in length which causes errors and inefficiencies in sequencing and prevents paired end reads.

Compositions and methods detailed in this disclosure provide sequencing libraries which allow for reduction in errors, increased efficiency, and allow for paired end reads.

SUMMARY OF THE INVENTION

Oligonucleotide primers and methods of use in producing sequencing libraries are provided according to aspects of the present disclosure which include, from 5' to 3', a homopolymer-hybridizing region, and an anchor region comprising 5'-$(\lambda)_n N_m$-3', wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, where n is an integer in the range of 1 to 20, or greater, and m is an integer in the range of 1-10, or greater, wherein the homopolymer-hybridizing region hybridizes to a complementary homopolymer tract of a target nucleic acid, wherein the complementary homopolymer tract comprises a contiguous sequence of complementary elements, wherein λ is any nucleotide or nucleotide analog with the proviso that X is not a nucleotide or nucleotide analog complementary to a complementary element of the complementary homopolymer tract, and wherein N is any nucleotide or nucleotide analog.

According to aspects of the present disclosure, the homopolymer-hybridizing region, and anchor region together have a total length in the range of about 7 to about 200 nucleotides, $T_m$ increasing nucleotide analogs, and nucleotide analogs. According to aspects of the present disclosure, the homopolymer-hybridizing region, and anchor region together have a total length in the range of about 8 to about 150 nucleotides, $T_m$ increasing nucleotide analogs, and nucleotide analogs. According to aspects of the present disclosure, the homopolymer-hybridizing region, and anchor region together have a total length in the range of about 9 to about 100 nucleotides, $T_m$ increasing nucleotide analogs, and nucleotide analogs. According to aspects of the present disclosure, the homopolymer-hybridizing region, and anchor region together have a total length in the range of about 10 to about 125 nucleotides, $T_m$ increasing nucleotide analogs, and nucleotide analogs. According to aspects of the present disclosure, the homopolymer-hybridizing region, and anchor region together have a total length in the range of about 10 to about 100 nucleotides, $T_m$ increasing nucleotide analogs, and nucleotide analogs. According to aspects of the present disclosure, the homopolymer-hybridizing region, and anchor region together have a total length in the range of about 10 to about 90 nucleotides, $T_m$ increasing nucleotide analogs, and nucleotide analogs. According to aspects of the present disclosure, the homopolymer-hybridizing region, and anchor region together have a total length in the range of about 10 to about 80 nucleotides, $T_m$ increasing nucleotide analogs, and nucleotide analogs. According to aspects of the present disclosure, the homopolymer-hybridizing region, and anchor region together have a total length in the range of about 10 to about 70 nucleotides, $T_m$ increasing nucleotide analogs, and nucleotide analogs. According to aspects of the present disclosure, the homopolymer-hybridizing region, and anchor region together have a total length in the range of about 10 to about 60 nucleotides, $T_m$ increasing nucleotide analogs, and nucleotide analogs. According to aspects of the present disclosure, the homopolymer-hybridizing region, and anchor region together have a total length in the range of about 10 to about 50 nucleotides, $T_m$ increasing nucleotide analogs, and nucleotide analogs.

According to aspects of the present disclosure, the homopolymer-hybridizing region, and anchor region together have a total length in the range of about 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides, $T_m$ increasing nucleotide analogs, and nucleotide analogs.

Oligonucleotide primers are provided according to aspects of the present disclosure which include, from 5' to 3', a poly(A) homopolymer-hybridizing region, and the anchor region comprising 5'-$(\lambda)_n N_m$-3', where n is an integer in the range of 1 to 20, or greater, and m is an integer in the range of 1-10, or greater, wherein the poly(A) homopolymer-hybridizing region is a contiguous sequence of 5 to 20 elements, wherein the elements are nucleotides or $T_m$ increasing nucleotide analogs, wherein the poly(A) homopolymer-hybridizing region hybridizes to a poly(A) homopolymer tract of a target nucleic acid, wherein at least 4 of the elements are $T_m$ increasing nucleotide analogs, wherein λ is any nucleotide or nucleotide analog with the proviso that X is not a nucleotide or nucleotide analog complementary to a residue of the poly(A) homopolymer tract, and wherein N is any nucleotide or nucleotide analog.

Oligonucleotide primers are provided according to aspects of the present disclosure which include, from 5' to 3', a poly(U) homopolymer-hybridizing region, and the anchor region comprising 5'-$(\lambda)_n N_m$-3', where n is an integer in the range of 1 to 20, or greater, and m is an integer in the range of 1-10, or greater, wherein the poly(U) homopolymer-hybridizing region is a contiguous sequence of 5 to 20 elements, wherein the elements are nucleotides or $T_m$ increasing nucleotide analogs, wherein the poly(U) homopolymer-hybridizing region hybridizes to a poly(U) homopolymer tract of a target nucleic acid, wherein at least 4 of the elements are $T_m$ increasing nucleotide analogs, wherein λ is any nucleotide or nucleotide analog with the proviso that X is not a nucleotide or nucleotide analog complementary to a residue of the poly(U) homopolymer tract, and wherein N is any nucleotide or nucleotide analog.

Oligonucleotide primers are provided according to aspects of the present disclosure which include, from 5' to 3', a poly(G) homopolymer-hybridizing region, and the anchor region comprising 5'-(λ)$_n$N$_m$-3', where n is an integer in the range of 1 to 20, or greater, and m is an integer in the range of 1-10, or greater, wherein the poly(G) homopolymer-hybridizing region is a contiguous sequence of 5 to 20 elements, wherein the elements are nucleotides or $T_m$ increasing nucleotide analogs, wherein the homopolymer-hybridizing region hybridizes to a poly(G) homopolymer tract of a target nucleic acid, wherein at least 4 of the elements are $T_m$ increasing nucleotide analogs, wherein λ is any nucleotide or nucleotide analog with the proviso that X is not a nucleotide or nucleotide analog complementary to a residue of the poly(G) homopolymer tract, and wherein N is any nucleotide or nucleotide analog.

Oligonucleotide primers are provided according to aspects of the present disclosure which include, from 5' to 3', a poly(C)-homopolymer-hybridizing region, and the anchor region comprising 5'-(λ)$_n$N$_m$-3', where n is an integer in the range of 1 to 20, or greater, and m is an integer in the range of 1-10, or greater, wherein the poly(C) homopolymer-hybridizing region is a contiguous sequence of 5 to 20 elements, wherein the elements are nucleotides or $T_m$ increasing nucleotide analogs, wherein the homopolymer-hybridizing region hybridizes to a poly(C) homopolymer tract of a target nucleic acid, wherein at least 4 of the elements are $T_m$ increasing nucleotide analogs, wherein λ is any nucleotide or nucleotide analog with the proviso that X is not a nucleotide or nucleotide analog complementary to a residue of the poly(C) homopolymer tract, and wherein N is any nucleotide or nucleotide analog.

Oligonucleotide primers are provided according to aspects of the present disclosure which include, from 5' to 3', a poly(T)-homopolymer-hybridizing region, and the anchor region comprising 5'-(λ)$_n$N$_m$-3', where n is an integer in the range of 1 to 20, or greater, and m is an integer in the range of 1-10, or greater, wherein the poly(T) homopolymer-hybridizing region is a contiguous sequence of 5 to 20 elements, wherein the elements are nucleotides or $T_m$ increasing nucleotide analogs, wherein the homopolymer-hybridizing region hybridizes to a poly(T) homopolymer tract of a target nucleic acid, wherein at least 4 of the elements are $T_m$ increasing nucleotide analogs, wherein λ is any nucleotide or nucleotide analog with the proviso that X is not a nucleotide or nucleotide analog complementary to a residue of the poly(T) homopolymer tract, and wherein N is any nucleotide or nucleotide analog.

The $T_m$ increasing nucleotide analogs included in oligonucleotide primers according to aspects of the present invention are not limited and include, but are not limited to, a locked nucleic acid, a peptide nucleic acid, and a bridged nucleic acid, or a combination of any two or more thereof. The $T_m$ increasing nucleotide analogs included in oligonucleotide primers according to aspects of the present invention are not limited and include, but are not limited to, propynyl-deoxyuridine and 5-hydroxybutynl-2'-deoxyuridine, 5-methyl dC, 2, 6-diaminopurine, and combinations thereof.

Oligonucleotide primers are provided according to aspects of the present disclosure which include a 5' primer tag sequence (PTS) covalently bonded to a 5' residue of the homopolymer-hybridizing region.

Oligonucleotide primers are provided according to aspects of the present disclosure wherein the homopolymer-hybridizing region is a contiguous sequence of 7 to 11 elements, and wherein 5, 6, or 7 of the elements are $T_m$ increasing nucleotide analogs.

Oligonucleotide primers are provided according to aspects of the present disclosure which include, from 5' to 3', a primer tag sequence, a homopolymer hybridizing region, and an anchor region comprising 5'-(λ)$_n$N$_m$-3', where n is an integer in the range of 1 to 20, or greater, and m is an integer in the range of 1-10, or greater, wherein the homopolymer hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer hybridizing region hybridizes to a complementary homopolymer tract of a target nucleic acid, wherein the complementary homopolymer tract comprises a contiguous sequence of complementary elements, wherein λ is any nucleotide or nucleotide analog with the proviso that λ is not a nucleotide or nucleotide analog complementary to a complementary element of the complementary homopolymer tract, and wherein N is any nucleotide or nucleotide analog. Optionally, the homopolymer hybridizing region is a contiguous sequence of 5 to 15 elements.

Oligonucleotide primers are provided according to aspects of the present disclosure which include, from 5' to 3', a poly(A) homopolymer-hybridizing region, and the anchor region comprising 5'-(λ)$_n$N$_m$-3', where n is an integer in the range of 1 to 20, or greater, and m is an integer in the range of 1-10, or greater, wherein the poly(A) homopolymer-hybridizing region is a contiguous sequence of 5 to 15 elements, wherein the elements are nucleotides or $T_m$ increasing nucleotide analogs, wherein the poly(A) homopolymer-hybridizing region hybridizes to a poly(A) homopolymer tract of a target nucleic acid, wherein at least 4 of the elements are $T_m$ increasing nucleotide analogs, wherein λ is any nucleotide or nucleotide analog with the proviso that λ is not a nucleotide or nucleotide analog complementary to a residue of the poly(A) homopolymer tract, and wherein N is any nucleotide or nucleotide analog.

Oligonucleotide primers are provided according to aspects of the present disclosure which include, from 5' to 3', the primer tag sequence (PTS), the poly(A) homopolymer-hybridizing region, and the anchor region comprising 5'-(λ)$_n$N$_m$-3', where n is an integer in the range of 1 to 20, or greater, and m is an integer in the range of 1-10, or greater, wherein the poly(A) homopolymer-hybridizing region is a contiguous sequence of 5 to 15 elements, wherein the elements are nucleotides or $T_m$ increasing nucleotide analogs, wherein the poly(A) homopolymer-hybridizing region hybridizes to the poly(A) homopolymer tract of a target nucleic acid, wherein at least 4 of the elements are $T_m$ increasing nucleotide analogs, wherein λ is any nucleotide or nucleotide analog with the proviso that λ is not a nucleotide or nucleotide analog complementary to a residue of the poly(A) homopolymer tract, and wherein N is any nucleotide or nucleotide analog.

Oligonucleotide primer sets are provided according to aspects of the present disclosure which include two or more oligonucleotide primers described herein. According to further aspects, the two or more oligonucleotide primers included in a primer set according to aspects of the present disclosure have different anchor regions.

Oligonucleotide primer sets are provided according to aspects of the present disclosure which include at least 12 or more oligonucleotide primers which include, from 5' to 3', a homopolymer-hybridizing region, and an anchor region comprising 5'-$(\lambda)_n N_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements, wherein $\lambda$ is any nucleotide or nucleotide analog with the proviso that $\lambda$ is not a nucleotide or nucleotide analog complementary to a complementary element of the complementary homopolymer tract, and wherein N is any nucleotide or nucleotide analog, for use where the complementary elements of the target nucleic acid are "A", (i.e. a poly(A) tract) and the oligonucleotide primer set comprises at least twelve oligonucleotide primers where the anchor region 5'-$(\lambda)_n N_m$-3' includes at least 5'-$(\lambda)_1 N_1$-3', such that the oligonucleotide primer set includes at least one oligonucleotide primer where 5'-$(\lambda)_1 N_1$-3' is 5'-AA-3', at least one oligonucleotide primer where 5'-$(\lambda)_1 N_1$-3' is 5'-AT-3', at least one oligonucleotide primer where 5'-$(\lambda)_1 N_1$-3' is 5'-AC-3', at least one oligonucleotide primer where 5'-$(\lambda)_1 N_1$-3' is 5'-AG-3', at least one oligonucleotide primer where 5'-$(\lambda)_1 N_1$-3' is 5'-CA-3', at least one oligonucleotide primer where 5'-$(\lambda)_1 N_1$-3' is 5'-CT-3' at least one oligonucleotide primer where 5'-$(\lambda)_1 N_1$-3' is 5'-CC-3', at least one oligonucleotide primer where 5'-$(\lambda)_1 N_1$-3' is 5'-CG-3', at least one oligonucleotide primer where 5'-$(\lambda)_1 N_1$-3' is 5'-GA-3', at least one oligonucleotide primer where 5'-$(\lambda)_1 N_1$-3' is 5'-GT-3', at least one oligonucleotide primer where 5'-$(\lambda)_1 N_1$-3' is 5'-GC-3', and at least one oligonucleotide primer where 5'-$(\lambda)_1 N_1$-3' is 5'-GG-3'. In each case, each of the specified nucleotides of 5'-$(\lambda)_1 N_1$-3' can be the specified nucleotides or one or both can be a corresponding nucleotide analog.

Oligonucleotide primer sets are provided according to aspects of the present disclosure which include at least 12 or more oligonucleotide primers which include, from 5' to 3', a homopolymer-hybridizing region, and an anchor region comprising 5'-$(\lambda)_n N_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements, wherein $\lambda$ is any nucleotide or nucleotide analog with the proviso that $\lambda$ is not a nucleotide or nucleotide analog complementary to a complementary element of the complementary homopolymer tract, and wherein N is any nucleotide or nucleotide analog, for use where the complementary elements of the target nucleic acid are "C", (i.e. a poly(C) tract) and the oligonucleotide primer set comprises at least twelve oligonucleotide primers where the anchor region 5'-$(\lambda)_n N_m$-3' includes at least 5'-$(\lambda)_1 N_1$-3', such that the oligonucleotide primer set includes at least one oligonucleotide primer where 5'-$(\lambda)_1 N_1$-3' is 5'-AA-3', at least one oligonucleotide primer where 5'-$(\lambda)_1 N_1$-3' is 5'-AT-3', at least one oligonucleotide primer where 5'-$(\lambda)_1 N_1$-3' is 5'-AC-3', at least one oligonucleotide primer where 5'-$(\lambda)_1 N_1$-3' is 5'-AG-3', at least one oligonucleotide primer where 5'-$(\lambda)_1 N_1$-3' is 5'-CA-3', at least one oligonucleotide primer where 5'-$(\lambda)_1 N_1$-3' is 5'-CT-3' at least one oligonucleotide primer where 5'-$(\lambda)_1 N_1$-3' is 5'-CC-3', at least one oligonucleotide primer where 5'-$(\lambda)_1 N_1$-3' is 5'-CG-3', at least one oligonucleotide primer where 5'-$(\lambda)_1 N_1$-3' is 5'-TA-3', at least one oligonucleotide primer where 5'-$(\lambda)_1 N_1$-3' is 5'-TT-3', at least one oligonucleotide primer where 5'-$(\lambda)_1 N_1$-3' is 5'-TC-3', and at least one oligonucleotide primer where 5'-$(\lambda)_1 N_1$-3' is 5'-TG-3'. In each case, each of the specified nucleotides of 5'-$(\lambda)_1 N_1$-3' can be the specified nucleotides or one or both can be a corresponding nucleotide analog.

Oligonucleotide primer sets are provided according to aspects of the present disclosure which include at least 12 or more oligonucleotide primers which include, from 5' to 3', a homopolymer-hybridizing region, and an anchor region comprising 5'-$(\lambda)_n N_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements, wherein $\lambda$ is any nucleotide or nucleotide analog with the proviso that $\lambda$ is not a nucleotide or nucleotide analog complementary to a complementary element of the complementary homopolymer tract, and wherein N is any nucleotide or nucleotide analog, for use where the complementary elements of the target nucleic acid are "G", (i.e. a poly(G) tract) and the oligonucleotide primer set comprises at least twelve oligonucleotide primers where the anchor region 5'-$(\lambda)_n N_m$-3' includes at least 5'-$(\lambda)_1 N_1$-3', such that the oligonucleotide primer set includes at least one oligonucleotide primer where 5'-$(\lambda)_1 N_1$-3' is 5'-AA-3', at least one oligonucleotide primer where 5'-$(\lambda)_1 N_1$-3' is 5'-AT-3', at least one oligonucleotide primer where 5'-$(\lambda)_1 N_1$-3' is 5'-AC-3', at least one oligonucleotide primer where 5'-$(\lambda)_1 N_1$-3' is 5'-AG-3', at least one oligonucleotide primer where 5'-$(\lambda)_1 N_1$-3' is 5'-GA-3', at least one oligonucleotide primer where 5'-$(\lambda)_1 N_1$-3' is 5'-GT-3' at least one oligonucleotide primer where 5'-$(\lambda)_1 N_1$-3' is 5'-GC-3', at least one oligonucleotide primer where 5'-$(\lambda)_1 N_1$-3' is 5'-GG-3', at least one oligonucleotide primer where 5'-$(\lambda)_1 N_1$-3' is 5'-TA-3', at least one oligonucleotide primer where 5'-$(\lambda)_1 N_1$-3' is 5'-TT-3', at least one oligonucleotide primer where 5'-$(\lambda)_1 N_1$-3' is 5'-TC-3', and at least one oligonucleotide primer where 5'-$(\lambda)_1 N_1$-3' is 5'-TG-3'. In each case, each of the specified nucleotides of 5'-$(\lambda)_1 N_1$-3' can be the specified nucleotides or one or both can be a corresponding nucleotide analog.

Oligonucleotide primer sets are provided according to aspects of the present disclosure which include at least 12 or more oligonucleotide primers which include, from 5' to 3', a homopolymer-hybridizing region, and an anchor region comprising 5'-$(\lambda)_n N_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements, wherein λ is any nucleotide or nucleotide analog with the proviso that λ is not a nucleotide or nucleotide analog complementary to a complementary element of the complementary homopolymer tract, and wherein N is any nucleotide or nucleotide analog for use where the complementary elements of the target nucleic acid are "T", or "U" (i.e. a poly(T) tract or poly (U) tract) and the oligonucleotide primer set comprises at least twelve oligonucleotide primers where the anchor region 5'-(λ)$_n$N$_m$-3' includes at least 5'-(λ)$_1$N$_1$-3', such that the oligonucleotide primer set includes at least one oligonucleotide primer where 5'-(λ)$_1$N$_1$-3' is 5'-CA-3', at least one oligonucleotide primer where 5'-(λ)$_1$N$_1$-3' is 5'-CT-3', at least one oligonucleotide primer where 5'-(λ)$_1$N$_1$-3' is 5'-CC-3', at least one oligonucleotide primer where 5'-(λ)$_1$N$_1$-3' is 5'-CG-3', at least one oligonucleotide primer where 5'-(λ)$_1$N$_1$-3' is 5'-GA-3', at least one oligonucleotide primer where 5'-(λ)$_1$N$_1$-3' is 5'-GT-3' at least one oligonucleotide primer where 5'-(λ)$_1$N$_1$-3' is 5'-GC-3', at least one oligonucleotide primer where 5'-(λ)$_1$N$_1$-3' is 5'-GG-3', at least one oligonucleotide primer where 5'-(λ)$_1$N$_1$-3' is 5'-TA-3', at least one oligonucleotide primer where 5'-(λ)$_1$N$_1$-3' is 5'-TT-3', at least one oligonucleotide primer where 5'-(λ)$_1$N$_1$-3' is 5'-TC-3', and at least one oligonucleotide primer where 5'-(λ)$_1$N$_1$-3' is 5'-TG-3'. In each case, each of the specified nucleotides of 5'-(λ)$_1$N$_1$-3' can be the specified nucleotides or one or both can be a corresponding nucleotide analog.

According to aspects of the present disclosure, the oligonucleotide primers of a primer set are provided in an equimolar mixture.

Methods of generating a sequencing library are provided according to aspects of the present disclosure which include providing an oligonucleotide primer or oligonucleotide primer set according to aspects of the present invention; annealing the oligonucleotide primer or oligonucleotide primer set to target nucleic acid, the target nucleic acid comprising the complementary homopolymer tract having at least 5 to 20 contiguous complementary elements, or at least 5 to 15 contiguous complementary elements; and extending the oligonucleotide primer under extension reaction conditions, producing an extension product complementary to at least a portion of the target nucleic acid. According to particular aspects, the target nucleic acid is RNA and extending the oligonucleotide primer comprises reverse transcription using a reverse transcriptase to produce a complementary DNA (cDNA). According to further aspects, methods of generating a sequencing library include polymerizing a second strand of DNA complementary to the extension product, producing double-stranded nucleic acid. According to further aspects, methods of generating a sequencing library include amplifying the double-stranded nucleic acid.

Kits are provided herein which include an oligonucleotide or oligonucleotide primer set according to aspects of the present disclosure.

DETAILED DESCRIPTION OF THE INVENTION

Figure 1:
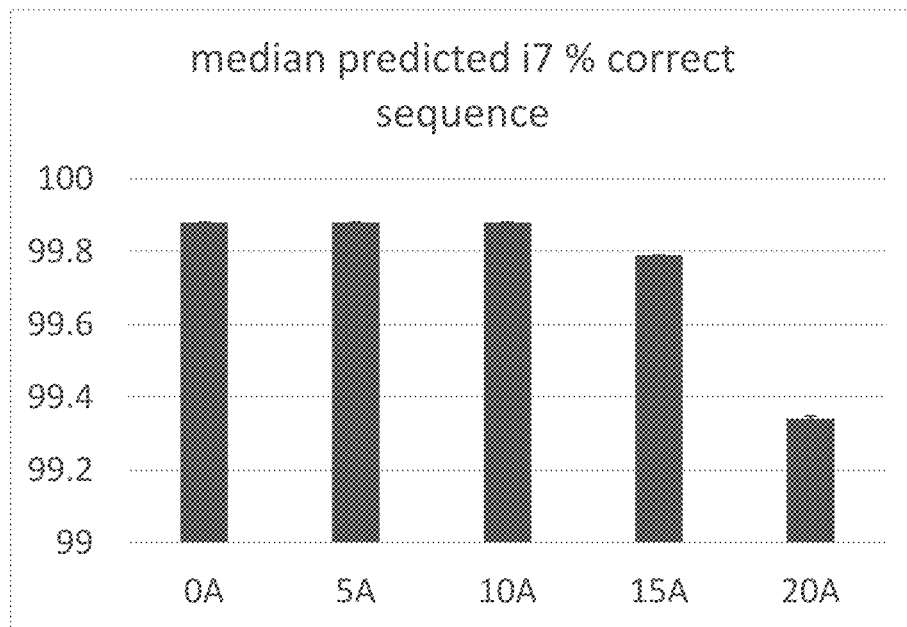
FIG. 1 is a graph showing that longer poly(A) runs in a target nucleic acid cause a decrease in index quality, here i7 quality, an effect that was detected with 15A and 20A configurations.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Herdewijn, P. (Ed.), Oligonucleotide Synthesis: Methods and Applications, Methods in Molecular Biology, Humana Press, 2004; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

Oligonucleotide primers, sets of oligonucleotide primers, and methods of their use in producing sequencing libraries are provided according to aspects of the present disclosure.

Oligonucleotide primers are provided according to the present disclosure which include, from 5' to 3', a homopolymer-hybridizing region, and an anchor region 5'-(λ)$_n$N$_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the homopolymer-hybridizing region is a contiguous, covalently bonded, linear sequence of the 5 to 20 elements, wherein the homopolymer-hybridizing region hybridizes to a complementary homopolymer tract of a target nucleic acid, wherein the complementary homopolymer tract comprises a contiguous sequence of "complementary elements", wherein the "complementary elements" are complementary to the elements of the homopolymer-hybridizing region, wherein λ is any nucleotide or nucleotide analog with the proviso that λ is not a nucleotide or nucleotide analog complementary to a complementary element of the complementary homopolymer tract, and wherein N is any nucleotide or nucleotide analog.

Optionally included is a primer tag sequence (PTS) such that oligonucleotide primers are provided according to the present disclosure which include, from 5' to 3', a PTS, a homopolymer-hybridizing region, and an anchor region 5'-(λ)$_n$N$_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the homopolymer-hybridizing region is a contiguous, covalently bonded, linear, sequence of the 5 to 20 elements, wherein the homopolymer-hybridizing region hybridizes to a complementary homopolymer tract of a target nucleic acid, wherein the complementary homopolymer tract comprises a contiguous sequence of complementary elements, wherein the complementary elements are complementary to the elements of the homopolymer-hybridizing region, wherein "V" is any nucleotide or nucleotide analog with the proviso that "V" is not a nucleotide or nucleotide analog complementary to an element of the complementary homopolymer tract, and wherein N is any nucleotide or nucleotide analog.

Figures 10, 11:
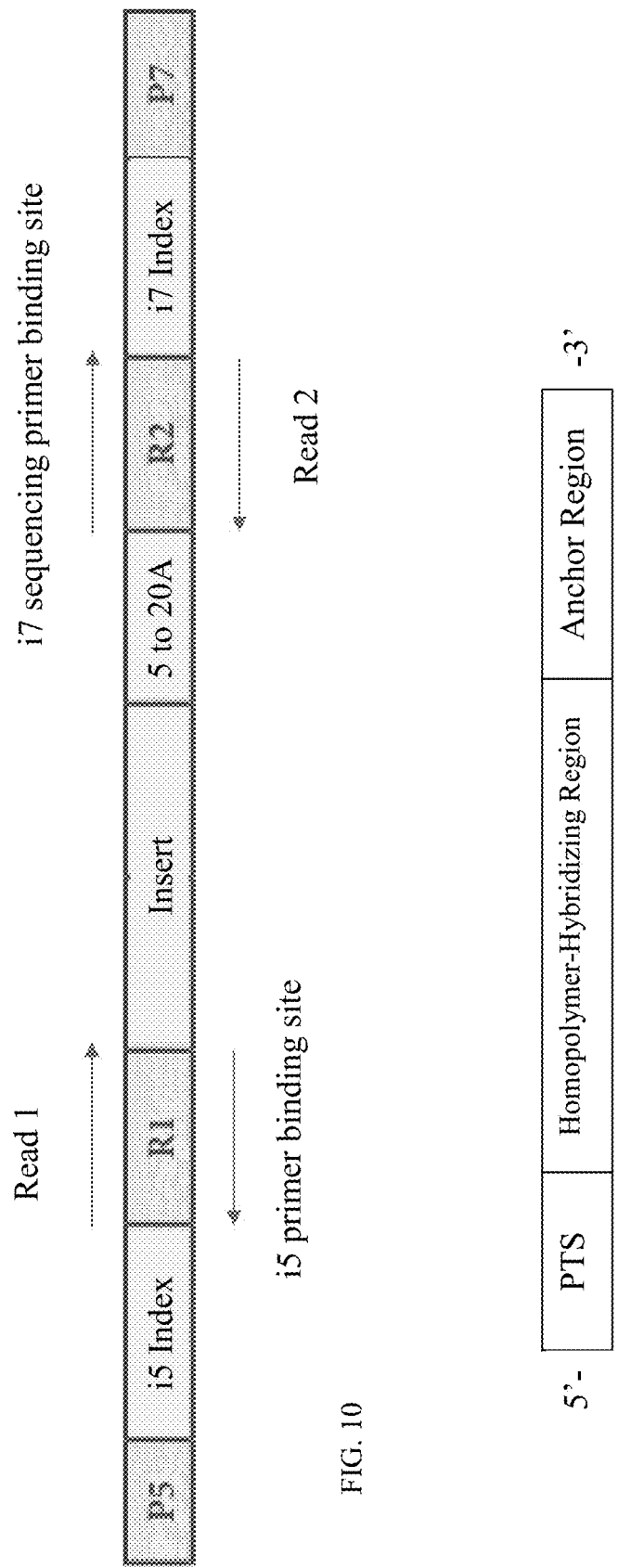
FIG. 10 is a schematic diagram illustrating an example sequencing library product of the present disclosure useful for paired end dual index sequencing.
FIG. 11 is a schematic diagram showing an oligonucleotide primer according to aspects of the present disclosure which includes, from 5' to 3', a PTS, a homopolymer-hybridizing region, and an anchor region including at least λN.

FIG. 11 is a schematic diagram showing an oligonucleotide primer according to aspects of the present disclosure which includes, from 5' to 3', a PTS, a homopolymer-hybridizing region, and an anchor region 5'-(λ)$_n$N$_m$-3', where n is an integer in the range of 1 to 20, or greater, and m is an integer in the range of 1-10, or greater.

As stated, the homopolymer-hybridizing region is a contiguous, covalently bonded, linear sequence of the 5 to 20 elements wherein the elements are nucleotides or $T_m$ increasing nucleotide analogs, wherein the homopolymer-hybridizing region hybridizes to a complementary homopolymer tract of a target nucleic acid, wherein the complementary homopolymer tract comprises a contiguous sequence of "complementary elements" that are complementary to the elements of the homopolymer-hybridizing region. The complementary homopolymer tract of a target nucleic acid can be a polyadenylic acid (poly(A)) sequence according to aspects of the present disclosure. The complementary homopolymer tract of a target nucleic acid can be a polyuridylic acid (poly(U)) sequence according to aspects of the present disclosure. The complementary homopolymer tract of a target nucleic acid can be a polyguanylic acid (poly(G)) sequence according to aspects of the present disclosure. The complementary homopolymer tract of a target nucleic acid can be a polycytidylic acid (poly(C)) sequence according to aspects of the present disclosure. The complementary homopolymer tract of a target nucleic acid can be a polythymidylic acid (poly(T)) sequence according to aspects of the present disclosure.

Thus, oligonucleotide primers are provided according to aspects of the present disclosure which include from 5' to 3', a poly(A)-homopolymer-hybridizing region, and an anchor region 5'-(λ)$_n$N$_m$-3', where n is an integer in the range of 1 to 20, or greater, and m is an integer in the range of 1-10, or greater, wherein the poly(A)-homopolymer hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the poly(A)-homopolymer-hybridizing region is a contiguous, covalently bonded, linear sequence of the 5 to 20 elements, wherein the poly(A)-homopolymer-hybridizing region hybridizes to a poly(A) homopolymer tract of a target nucleic acid, wherein λ is any nucleotide or nucleotide analog with the proviso that λ is not a nucleotide or nucleotide analog complementary to a residue of the poly(A) homopolymer tract, and wherein N is any nucleotide or nucleotide analog. According to aspects of the present disclosure, λ is V as defined in Table IV. According to aspects of the present disclosure, the $T_m$ increasing nucleotide analogs included in the poly(A)-homopolymer-hybridizing region are complementary to A residues of the poly (A)-homopolymer-hybridizing region and are independently selected from: a locked nucleic acid (LNA), a peptide nucleic acid (PNA), and a bridged nucleic acid (BNA). Any of various $T_m$ increasing nucleotide analogs complementary to A residues of the poly(A)-homopolymer-hybridizing region can be used including, but not limited to, propynyl-deoxyuridine and 5-hydroxybutynl-2'-deoxyuridine, according to aspects of the present disclosure.

Oligonucleotide primers are provided according to aspects of the present disclosure which include from 5' to 3', a poly(U)-homopolymer-hybridizing region, and an anchor region 5'-(λ)$_n$N$_m$-3', where n is an integer in the range of 1 to 20, or greater, and m is an integer in the range of 1-10, or greater, wherein the poly(U)-homopolymer-hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the poly(U)-homopolymer-hybridizing region is a contiguous, covalently bonded, linear sequence of the 5 to 20 elements, wherein the poly(U)-homopolymer-hybridizing region hybridizes to a poly(U) homopolymer tract of a target nucleic acid, wherein λ is any nucleotide or nucleotide analog with the proviso that λ is not a nucleotide or nucleotide analog complementary to a residue of the poly(U) homopolymer tract, and wherein N is any nucleotide or nucleotide analog. According to aspects of the present disclosure, λ is B as defined in Table IV. According to aspects of the present disclosure, the $T_m$ increasing nucleotide analogs included in the poly(U)-homopolymer-hybridizing region are complementary to U residues of the poly (U)-homopolymer-hybridizing region and are independently selected from: a locked nucleic acid (LNA), a peptide nucleic acid (PNA), and a bridged nucleic acid (BNA). Any of various $T_m$ increasing nucleotide analogs complementary to U residues of the poly(U)-homopolymer-hybridizing region can be used including, but not limited to, 2, 6-diaminopurine, according to aspects of the present disclosure.

Oligonucleotide primers are provided according to aspects of the present disclosure which include from 5' to 3', a poly(G)-homopolymer-hybridizing region, and an anchor region 5'-($\lambda$)$_n$N$_m$-3', where n is an integer in the range of 1 to 20, or greater, and m is an integer in the range of 1-10, or greater, wherein the poly(G)-homopolymer-hybridizing region is a contiguous sequence of 5 to 20 elements, wherein the elements are nucleotides or T$_m$ increasing nucleotide analogs, wherein at least 4, and up to 20, such as 4, 5, 6, 7, 8, 9, 10, 11, 12, 13, 14, 15, 16, 17, 18, 19, or 20, of the elements are T$_m$ increasing nucleotide analogs, wherein the poly(G)-homopolymer-hybridizing region is a contiguous, covalently bonded, linear sequence of the 5 to 20 elements, wherein the poly(G)-homopolymer-hybridizing region hybridizes to a poly(G) homopolymer tract of a target nucleic acid, wherein $\lambda$ is any nucleotide or nucleotide analog with the proviso that $\lambda$ is not a nucleotide or nucleotide analog complementary to a residue of the poly(G) homopolymer tract, and wherein N is any nucleotide or nucleotide analog. According to aspects of the present disclosure, $\lambda$ is D as defined in Table IV. According to aspects of the present disclosure, the T$_m$ increasing nucleotide analogs included in the poly(G)-homopolymer-hybridizing region are complementary to G residues of the poly(G)-homopolymer-hybridizing region and are independently selected from: a locked nucleic acid, a peptide nucleic acid, and a bridged nucleic acid. Any of various T$_m$ increasing nucleotide analogs complementary to G residues of the poly(G)-homopolymer-hybridizing region can be used including, but not limited to, 5-methyl dC, according to aspects of the present disclosure.

Oligonucleotide primers are provided according to aspects of the present disclosure which include from 5' to 3', a poly(C)-homopolymer-hybridizing region, and an anchor region 5'-($\lambda$)$_n$N$_m$-3', where n is an integer in the range of 1 to 20, or greater, and m is an integer in the range of 1-10, or greater, wherein the poly(C)-homopolymer-hybridizing region is a contiguous sequence of 5 to 20 elements, wherein the elements are nucleotides or T$_m$ increasing nucleotide analogs, wherein at least 4, and up to 20, such as 4, 5, 6, 7, 8, 9, 10, 11, 12, 13, 14, 15, 16, 17, 18, 19, or 20, of the elements are T$_m$ increasing nucleotide analogs, wherein the poly(C)-homopolymer-hybridizing region is a contiguous, covalently bonded, linear sequence of the 5 to 20 elements, wherein the poly(C)-homopolymer-hybridizing region hybridizes to a poly(C) homopolymer tract of a target nucleic acid, wherein $\lambda$ is any nucleotide or nucleotide analog with the proviso that $\lambda$ is not a nucleotide or nucleotide analog complementary to a residue of the poly(C) homopolymer tract, and wherein N is any nucleotide or nucleotide analog. According to aspects of the present disclosure, $\lambda$ is H as defined in Table IV. According to aspects of the present disclosure, the T$_m$ increasing nucleotide analogs included in the poly(C)-homopolymer-hybridizing region are complementary to C residues of the poly(C)-homopolymer-hybridizing region and are independently selected from: a locked nucleic acid, a peptide nucleic acid, and a bridged nucleic acid. Any of various T$_m$ increasing nucleotide analogs complementary to C residues of the poly(C)-homopolymer-hybridizing region can be used according to aspects of the present disclosure.

Oligonucleotide primers are provided according to aspects of the present disclosure which include from 5' to 3', a poly(T)-homopolymer-hybridizing region, and an anchor region 5'-($\lambda$)$_n$N$_m$-3', where n is an integer in the range of 1 to 20, or greater, and m is an integer in the range of 1-10, or greater, wherein the poly(T)-homopolymer-hybridizing region is a contiguous sequence of 5 to 20 elements, wherein the elements are nucleotides or T$_m$ increasing nucleotide analogs, wherein at least 4, and up to 20, such as 4, 5, 6, 7, 8, 9, 10, 11, 12, 13, 14, 15, 16, 17, 18, 19, or 20, of the elements are T$_m$ increasing nucleotide analogs, wherein the poly(T)-homopolymer-hybridizing region is a contiguous, covalently bonded, linear sequence of the 5 to 20 elements, wherein the poly(T)-homopolymer-hybridizing region hybridizes to a poly(T) homopolymer tract of a target nucleic acid, wherein $\lambda$ is any nucleotide or nucleotide analog with the proviso that $\lambda$ is not a nucleotide or nucleotide analog complementary to a residue of the poly(T) homopolymer tract, and wherein N is any nucleotide or nucleotide analog. According to aspects of the present disclosure, $\lambda$ is B as defined in Table IV. According to aspects of the present disclosure, the T$_m$ increasing nucleotide analogs included in the poly(T)-homopolymer-hybridizing region are complementary to T residues of the poly(T)-homopolymer-hybridizing region and are independently selected from: a locked nucleic acid (LNA), a peptide nucleic acid (PNA), and a bridged nucleic acid (BNA). Any of various T$_m$ increasing nucleotide analogs complementary to T residues of the poly(T)-homopolymer-hybridizing region can be used including, but not limited to, 2, 6-diaminopurine, according to aspects of the present disclosure.

According to aspects of the present disclosure, the homopolymer-hybridizing region is a contiguous, covalently bonded, linear sequence of 5 to 15 elements wherein the elements are nucleotides or T$_m$ increasing nucleotide analogs, wherein the homopolymer-hybridizing region hybridizes to a complementary homopolymer tract of a target nucleic acid, wherein the complementary homopolymer tract includes a contiguous sequence of complementary elements.

According to aspects of the present disclosure, oligonucleotide primers are provided which include, from 5' to 3', a poly(A)-homopolymer-hybridizing region, and an anchor region 5'-($\lambda$)$_n$N$_m$-3', where n is an integer in the range of 1 to 20, or greater, and m is an integer in the range of 1-10, or greater, wherein the poly(A)-homopolymer-hybridizing region is a contiguous sequence of 5 to 15 elements, wherein the elements are nucleotides or T$_m$ increasing nucleotide analogs, wherein at least 5, and up to 15, such as 5, 6, 7, 8, 9, 10, 11, 12, 13, 14, or 15, of the elements are T$_m$ increasing nucleotide analogs, wherein the poly(A)-homopolymer-hybridizing region is a contiguous, covalently bonded, linear sequence of the 5 to 15 elements, wherein the poly(A)-homopolymer-hybridizing region hybridizes to a poly(A) homopolymer tract of a target nucleic acid, wherein $\lambda$ is any nucleotide or nucleotide analog with the proviso that $\lambda$ is not a nucleotide or nucleotide analog complementary to a residue of the poly(A) homopolymer tract, and wherein N is any nucleotide or nucleotide analog. According to aspects of the present disclosure, the T$_m$ increasing nucleotide analogs are independently selected from: a locked nucleic acid, a peptide nucleic acid, a bridged nucleic acid. Any of various T$_m$ increasing nucleotide analogs complementary to A residues of the poly(A)-homopolymer-hybridizing region can be used including, but not limited to, propynyl-deoxyuridine and 5-hydroxybutynl-2'-deoxyuridine, according to aspects of the present disclosure.

According to aspects of the present disclosure oligonucleotide primers are provided which include, from 5' to 3', a primer tag sequence, a poly(A)-hybridizing region, and an anchor region 5'-($\lambda$)$_n$N$_m$-3', where n is an integer in the range of 1 to 20, or greater, and m is an integer in the range of 1-10, or greater, wherein the poly(A)-homopolymer-hybridizing region is a contiguous sequence of 5 to 15 elements, wherein the elements are nucleotides or $T_m$ increasing nucleotide analogs, wherein at least 4, and up to 15, such as 5, 6, 7, 8, 9, 10, 11, 12, 13, 14, or 15, of the elements are $T_m$ increasing nucleotide analogs, wherein the poly(A)-homopolymer-hybridizing region is a contiguous, covalently bonded, linear sequence of the 5 to 15 elements, wherein the poly(A)-homopolymer-hybridizing region hybridizes to a poly(A) homopolymer tract of a target nucleic acid, wherein λ is any nucleotide or nucleotide analog with the proviso that λ is not a nucleotide or nucleotide analog complementary to a residue of the poly(A) homopolymer tract, and wherein N is any nucleotide or nucleotide analog. According to aspects of the present disclosure, the $T_m$ increasing nucleotide analogs are independently selected from: a locked nucleic acid, a peptide nucleic acid, a bridged nucleic acid. Any of various $T_m$ increasing nucleotide analogs complementary to A residues of the poly(A)-homopolymer-hybridizing region can be used including, but not limited to, propynyl-deoxyuridine and 5-hydroxybutynl-2'-deoxyuridine, according to aspects of the present disclosure.

According to aspects of the present disclosure oligonucleotide primers are provided which include, from 5' to 3', an optional primer tag sequence, a poly(U)-, a poly(T)-, a poly(C)-, or a poly(G)-hybridizing region, and an anchor region 5'-(λ)$_n$N$_m$-3', where n is an integer in the range of 1 to 20, or greater, and m is an integer in the range of 1-10, or greater, wherein the poly(U)-, poly(T)-, poly(C)-, or poly (G)-homopolymer-hybridizing region is a contiguous sequence of 5 to 15 elements, wherein the elements are nucleotides or $T_m$ increasing nucleotide analogs, wherein at least 4, and up to 15, such as 5, 6, 7, 8, 9, 10, 11, 12, 13, 14, or 15, of the elements are $T_m$ increasing nucleotide analogs, wherein the poly(U)-, poly(T)-, poly(C)-, or poly(G)-homopolymer-hybridizing region is a contiguous, covalently bonded, linear sequence of the 5 to 15 elements, wherein the poly(U)-, poly(T)-, poly(C)-, or poly(G)-homopolymer-hybridizing region hybridizes to a complementary homopolymer tract of a target nucleic acid, wherein λ is any nucleotide or nucleotide analog with the proviso that λ is not a nucleotide or nucleotide analog complementary to a residue of the complementary homopolymer tract, and wherein N is any nucleotide or nucleotide analog. According to aspects of the present disclosure, the $T_m$ increasing nucleotide analogs are independently selected from: a locked nucleic acid, a peptide nucleic acid, a bridged nucleic acid. Any of various $T_m$ increasing nucleotide analogs complementary to residues of the poly(U)-, poly(T)-, poly(C)-, or poly(G)-homopolymer-hybridizing region can be used according to aspects of the present disclosure.

Oligonucleotide primers provided according to the present disclosure have various utilities, for example, use in preparation of libraries, such as sequencing libraries.

Preparation of a sequencing library using an oligonucleotide primer of the present disclosure allows for incorporation of fewer residues of a homopolymer tract of a target nucleic acid into the nucleic acid sequences which make up the library. The resulting shorter homopolymer tracts incorporated into the nucleic acid sequences which make up the library allow for more reliable sequencing of the library nucleic acid sequences.

Thus, for example, fewer "A" residues of a poly(A) tract, fewer "U" residues of a poly(U) tract, fewer "G" residues of a poly(G) tract, fewer "T" residues of a poly(T) tract, or fewer "C" residues of a poly(C) tract, of a target nucleic acid, are incorporated into the nucleic acid sequences which make up the sequencing library.

This has particular advantages when generating sequencing libraries from mRNA since mRNA molecules typically have long poly(A) tracts known as poly(A) tails. Poly(A) tails typically extend from about 100 to 250 residues in length.

Further, a homopolymer tract, such as a poly(A) tract, a poly(U) tract, a poly(T) tract, a poly(C) tract, or a poly(G) tract, may be added to RNA fragments during the process of library generation. When such homopolymer tracts are incorporated into libraries the sequencing quality is generally poor, including errors, inefficiencies in sequencing and preventing paired end reads.

By contrast, use of oligonucleotide primers according to aspects of the present disclosure produces sequencing libraries which have a reduced number of homopolymer tracts having more than 11 residues in length, and consequently, allows for a reduction in index errors, such as i7 index errors, and increased sequencing quality in the R2 direction, which enables paired-end sequencing runs from libraries generated using this method.

FIG. 10 illustrates an example sequencing library product of the present disclosure useful for paired end dual index sequencing. Each of the two reads (R1 and R2) includes an "insert" (target nucleic acid) derived from the starting nucleic acid modified according to methods of the present disclosure to include an adjacent homopolymer tract of 5 to 20 elements, in the illustrated case, a poly(A) tract comprising 5 to 20 adenines. It will be appreciated by those who are skilled in the art that there are many configurations of this example that are specific to particular equipment platforms, and that the compositions and methods of this disclosure are not limited to use with such specific equipment and associated procedures. Rather, the compositions and methods of the present disclosure may be used in any of various sequencing protocols and with various sequencing equipment.

According to aspects of the present disclosure, the homopolymer-hybridizing region is a contiguous sequence of 5 to 20 elements, wherein the elements are nucleotides or $T_m$ increasing nucleotide analogs, the nucleotides and $T_m$ increasing nucleotide analogs may be present in any order, in contiguous sequences of two or more nucleotides or contiguous sequences of two or more $T_m$ increasing nucleotide analogs, or interspersed so that no nucleotide is adjacent another nucleotide and no $T_m$ increasing nucleotide analog is adjacent to another $T_m$ increasing nucleotide analog in the nucleic acid sequence of the homopolymer-hybridizing region.

According to aspects of the present disclosure, the poly (A)-homopolymer-hybridizing region is a contiguous sequence of 5 to 20 elements, wherein the elements are nucleotides or $T_m$ increasing nucleotide analogs, the nucleotides and $T_m$ increasing nucleotide analogs may be present in any order, in contiguous sequences of two or more nucleotides or contiguous sequences of two or more $T_m$ increasing nucleotide analogs, or interspersed so that no nucleotide is adjacent another nucleotide and no $T_m$ increasing nucleotide analog is adjacent $T_m$ increasing nucleotide analog in the nucleic acid sequence of the poly(A)-homopolymer-hybridizing region.

According to aspects of the present disclosure, the poly (U)-homopolymer-hybridizing region is a contiguous sequence of 5 to 20 elements, wherein the elements are nucleotides or $T_m$ increasing nucleotide analogs, the nucleotides and $T_m$ increasing nucleotide analogs may be present in any order, in contiguous sequences of two or more nucleotides or contiguous sequences of two or more $T_m$ increasing nucleotide analogs, or interspersed so that no nucleotide is adjacent another nucleotide and no $T_m$ increasing nucleotide analog is adjacent $T_m$ increasing nucleotide analog in the nucleic acid sequence of the poly(U)-homopolymer-hybridizing region.

According to aspects of the present disclosure, the poly (G) homopolymer-hybridizing region is a contiguous sequence of 5 to 20 elements, wherein the elements are nucleotides or $T_m$ increasing nucleotide analogs, the nucleotides and $T_m$ increasing nucleotide analogs may be present in any order, in contiguous sequences of two or more nucleotides or contiguous sequences of two or more $T_m$ increasing nucleotide analogs, or interspersed so that no nucleotide is adjacent another nucleotide and no $T_m$ increasing nucleotide analog is adjacent $T_m$ increasing nucleotide analog in the nucleic acid sequence of the poly(G)-homopolymer-hybridizing region.

According to aspects of the present disclosure, the poly (C)-homopolymer-hybridizing region is a contiguous sequence of 5 to 20 elements, wherein the elements are nucleotides or $T_m$ increasing nucleotide analogs, the nucleotides and $T_m$ increasing nucleotide analogs may be present in any order, in contiguous sequences of two or more nucleotides or contiguous sequences of two or more $T_m$ increasing nucleotide analogs, or interspersed so that no nucleotide is adjacent another nucleotide and no $T_m$ increasing nucleotide analog is adjacent $T_m$ increasing nucleotide analog in the nucleic acid sequence of the poly(C)-homopolymer-hybridizing region.

According to aspects of the present disclosure, the poly (T)-homopolymer-hybridizing region is a contiguous sequence of 5 to 20 elements, wherein the elements are nucleotides or $T_m$ increasing nucleotide analogs, the nucleotides and $T_m$ increasing nucleotide analogs may be present in any order, in contiguous sequences of two or more nucleotides or contiguous sequences of two or more $T_m$ increasing nucleotide analogs, or interspersed so that no nucleotide is adjacent another nucleotide and no $T_m$ increasing nucleotide analog is adjacent $T_m$ increasing nucleotide analog in the nucleic acid sequence of the poly(T)-homopolymer-hybridizing region.

The term "upstream" refers to a nucleotide, nucleotide analog, or sequence including two or more nucleotides and/or nucleotide analogs that is located 5' to a reference nucleotide, nucleotide analog, or sequence including two or more nucleotides and/or nucleotide analogs. By contrast, the term "downstream" refers to a nucleotide, nucleotide analog, or sequence including two or more nucleotides and/or nucleotide analogs that is located 3' to a reference nucleotide, nucleotide analog, or sequence including two or more nucleotides and/or nucleotide analogs.

The term "anchor region" refers to an oligonucleotide region which is complementary to a region upstream of, and adjacent to, the complementary homopolymer tract. The anchor region has the general structural formula 5'-$(\lambda)_n N_m$-3', where n is an integer in the range of 1 to 20, or greater, and m is an integer in the range of 1-10, or greater. The anchor region is not limited with respect to the number of nucleotides, as long as it includes at least 5'-$\lambda_1 N_1$-3' where $\lambda$ is any nucleotide or nucleotide analog except a nucleotide or nucleotide analog complementary to a residue of the homopolymer tract of a target nucleic acid, and wherein N is any nucleotide or nucleotide analog.

According to particular aspects, the anchor region has the structural formula 5'-$(\lambda)_n N_m$-3', where n is 1, 2, 3, 4, 5, 6, 7, 8, 9, 10, 11, 12, 13, 14, 15, 16, 17, 18, 19, or 20 and m is 1, 2, 3, 4, 5, 6, 7, 8, 9, or 10.

According to particular aspects, the anchor region has the structural formula 5'-$(\lambda)_n N_m$-3', where n is 1, 2, 3, 4, 5, 6, 7, 8, 9, or 10 and m is 1, 2, 3, 4, 5, 6, 7, 8, 9, or 10. According to particular aspects, the anchor region has the structural formula 5'-$(\lambda)_n N_m$-3', where n is 11, 12, 13, 14, 15, 16, 17, 18, 19, or 20 and m is 1, 2, 3, 4, 5, 6, 7, 8, 9, or 10. According to particular aspects, the anchor region has the structural formula 5'-$(\lambda)_n N_m$-3', where n is 1, 2, 3, 4, 5, 6, 7, 8, 9, or 10 and m is 1, 2, 3, 4, or 5. According to particular aspects, the anchor region has the structural formula 5'-$(\lambda)_n N_m$-3', where n is 11, 12, 13, 14, 15, 16, 17, 18, 19, or 20 and m is 1, 2, 3, 4, or 5.

According to particular aspects, the anchor region has the structural formula 5'-$(\lambda)_n N_m$-3', where n is 5, 6, 7, 8, 9, or 10 and m is 1, 2, 3, 4, or 5. According to particular aspects, the anchor region has the structural formula 5'-$(\lambda)_n N_m$-3', where n is 5, 6, 7, 8, 9, or 10 and m is 5, 6, 7, 8, 9, or 10. According to particular aspects, the anchor region has the structural formula 5'-$(\lambda)_n N_m$-3', where n is 1, 2, 3, 4, or 5 and m is 5, 6, 7, 8, 9, or 10.

According to particular aspects, the anchor region has the structural formula 5'-$(\lambda)_n N_m$-3', where n is 1, 2, 3, 4, or 5 and m is 1, 2, 3, 4, or 5.

According to particular aspects, the anchor region has the structural formula 5'-$(\lambda)_n N_m$-3', where n is 1, 2, 3, or 4 and m is 1, 2, 3, or 4. According to particular aspects, the anchor region has the structural formula 5'-$(\lambda)_n N_m$-3', where n is 1, 2, or 3 and m is 1, 2, or 3. According to particular aspects, the anchor region has the structural formula 5'-$(\lambda)_n N_m$-3', where n is 1 or 2 and m is 1 or 2. According to particular aspects, the anchor region has the structural formula 5'-$(\lambda)_n N_m$-3', where n is 1 and m is 1.

According to aspects of the present disclosure where the homopolymer-hybridizing region is complementary to a poly(A) homopolymer tract of the target nucleic acid, the anchor region of the oligonucleotide primer is 5'-$(\lambda)_n N_m$-3', where n is an integer in the range of 1 to 20, or greater, and m is an integer in the range of 1-10, or greater, wherein $\lambda$ is any nucleotide or nucleotide analog except a nucleotide or nucleotide analog complementary to an A residue of the poly(A) homopolymer tract, and wherein N is any nucleotide or nucleotide analog.

According to aspects of the present disclosure where the poly(U)-homopolymer-hybridizing region is complementary to a poly(U) homopolymer tract of the target nucleic acid, the anchor region of the oligonucleotide primer is 5'-$(\lambda)_n N_m$-3', where n is an integer in the range of 1 to 20, or greater, and m is an integer in the range of 1-10, or greater, wherein $\lambda$ is any nucleotide or nucleotide analog except a nucleotide or nucleotide analog complementary to a U residue of the poly(U) homopolymer tract, and wherein N is any nucleotide or nucleotide analog.

According to aspects of the present disclosure where the poly(G)-homopolymer-hybridizing region is complementary to a poly(G) homopolymer tract of the target nucleic acid, the anchor region of the oligonucleotide primer is 5'-$(\lambda)_n N_m$-3', where n is an integer in the range of 1 to 20, or greater, and m is an integer in the range of 1-10, or greater, wherein $\lambda$ is any nucleotide or nucleotide analog except a nucleotide or nucleotide analog complementary to a G residue of the poly(G) homopolymer tract, and wherein N is any nucleotide or nucleotide analog.

According to aspects of the present disclosure where the poly(C)-homopolymer-hybridizing region is complementary to a poly(C) homopolymer tract of the target nucleic acid, the anchor region of the oligonucleotide primer is 5'-(λ)$_n$N$_m$-3', where n is an integer in the range of 1 to 20, or greater, and m is an integer in the range of 1-10, or greater, wherein λ is any nucleotide or nucleotide analog except a nucleotide or nucleotide analog complementary to a C residue of the poly(C) homopolymer tract, and wherein N is any nucleotide or nucleotide analog.

According to aspects of the present disclosure where the poly(T)-homopolymer-hybridizing region is complementary to a poly(T) homopolymer tract of the target nucleic acid, the anchor region of the oligonucleotide primer is 5'-(λ)$_n$N$_m$-3', where n is an integer in the range of 1 to 20, or greater, and m is an integer in the range of 1-10, or greater, wherein λ is any nucleotide or nucleotide analog except a nucleotide or nucleotide analog complementary to a T residue of the poly(T) homopolymer tract, and wherein N is any nucleotide or nucleotide analog.

The term "primer tag sequence," abbreviated PTS herein, refers to a contiguous, covalently bonded, linear sequence of nucleotides useful as a linker for linking to the ends of other DNA molecules, or to provide a common nucleic acid sequence for manipulations, such as a site for enzymatic cleavage, sequencing, PCR, or hybridization. A primer tag sequence may be included in an oligonucleotide primer used for annealing to the target nucleic acid, or it may be added later, such as by ligation or incorporation by PCR.

An included primer tag sequence may be a "5' overhang" primer tag sequence. The term "overhang" refers to a portion at the end of the oligonucleotide primer which is not complementary to the target nucleic acid and therefore does not anneal to the target nucleic acid.

The term "nucleotide" refers to a molecule including a nucleobase, sugar, and phosphate. Nucleotides are the monomeric units of a nucleic acid sequence, e.g. a DNA or RNA sequence. The term nucleotide includes ribonucleoside triphosphates, such as ATP, TTP, UTP, CTP, and GTP, and deoxyribonucleoside triphosphates, such as dATP, dCTP, dUTP, dGTP, and dTTP. Nucleotides are commonly referred to as A, T, G, C, or U as an abbreviation, in reference to the nucleobase, see Table IV.

The terms "Tm" and "melting temperature" refer to a temperature at which 50% (half) of population of double-stranded nucleic acid molecules become separated, i.e. single stranded. Methods for calculating Tm are well-known in the art.

The term "Tm increasing nucleotide analog" refers to a nucleotide analog that increases the melting temperature (Tm) of a double-stranded oligonucleotide that includes the nucleotide analog compared to the same double-stranded oligonucleotide without the nucleotide analog. A T$_m$ increasing nucleotide analog may include a modified nucleobase, a modified sugar, a modified phosphate, or a combination of any two or more such modifications. T$_m$ increasing nucleotide analogs include, but are not limited to, a locked nucleic acid, a peptide nucleic acid, and a bridged nucleic acid. Any of various T$_m$ increasing nucleotide analogs complementary to a specified residue of a homopolymer-hybridizing region or a combination thereof, can be used including, but not limited to, a locked nucleic acid, a peptide nucleic acid, a bridged nucleic acid, or a combination of any two or more thereof, according to aspects of the present disclosure. Any of various T$_m$ increasing nucleotide analogs complementary to a specified residue of a homopolymer-hybridizing region can be used including, but not limited to, 5-methyl dC, 2, 6-diaminopurine, propynyl-deoxyuridine, or 5-hydroxy-butynl-2'-deoxyuridine, according to aspects of the present disclosure. Combinations of propynyl-deoxyuridine, and 5-hydroxybutynl-2'-deoxyuridine can be used according to aspects of the present disclosure. Derivatives of Tm increasing nucleotide analogs can be included so long as the derivatives retain the function of increasing the melting temperature (Tm) of a double-stranded oligonucleotide that includes the nucleotide analog compared to the same double-stranded oligonucleotide without the nucleotide analog.

According to aspects of the disclosure, an included T$_m$ increasing nucleotide analog is not a locked nucleic acid.

The terms "nucleotide sequence" and "nucleic acid sequence" are used to refer to the ordering of nucleotides in an oligonucleotide or polynucleotide.

The terms "hybridization" and "hybridized" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide, betaine and polyethylene glycol. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. The term "annealing" as used herein refers to the pairing and binding of an oligonucleotide primer to a target nucleic acid, thereby enabling a nucleic acid polymerase to polymerize nucleotides into a nucleic acid molecule which is complementary to the target nucleic acid or a portion thereof. There is no intended distinction between the terms "annealing" and "hybridizing."

The term "complementary" as used herein encompasses, but is not limited to, Watson-Crick base pairing between nucleotides, between nucleotide analogs, or between nucleotides and nucleotide analogs, wherein nucleotides and/or nucleotide analogs are hydrogen bonded to one another, for example with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA-5' is 100%, or completely, complementary to a region of the nucleotide sequence 5'-TTAGCTGG-3'.

Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize. The terms "specific hybridization" and "specifically hybridizes" refer to hybridization of a particular nucleic acid to a target nucleic acid without substantial hybridization to nucleic acids other than the target nucleic acid in a sample.

The term "poly(A) tract," refers to a nucleic acid sequence of adenine, adenosine, or adenosine monophosphate residues which is located in a target nucleic acid molecule, such as a DNA molecule or an RNA molecule.

The term "poly(U) tract," refers to a nucleic acid sequence of uracil, uridine, or uridine monophosphate residues which is located in a target nucleic acid molecule, such as a DNA molecule or an RNA molecule.

The term "poly(G) tract," refers to a nucleic acid sequence of guanine, guanosine, or guanosine monophosphate residues which is located in a target nucleic acid molecule, such as a DNA molecule or an RNA molecule.

The term "poly(C) tract," refers to a nucleic acid sequence of cytosine, cytidine, or cytidine monophosphate residues which is located in a target nucleic acid molecule, such as a DNA molecule or an RNA molecule.

The term "poly(T) tract," refers to a nucleic acid sequence of thymine, thymidine, or thymidine monophosphate residues which is located in a target nucleic acid molecule, such as a DNA molecule or an RNA molecule.

As mentioned herein, oligonucleotide primers according to the present disclosure include an anchor region including $5'-(\lambda)_n N_m-3'$, where n is an integer in the range of 1 to 20, or greater, and m is an integer in the range of 1-10, or greater, wherein $\lambda$ is any nucleotide or nucleotide analog with the proviso that $\lambda$ is not a nucleotide or nucleotide analog complementary to a complementary element of the complementary homopolymer tract, and wherein N is any nucleotide or nucleotide analog.

Nucleotides and analogs thereof, including, but not limited to, deoxynucleotide triphosphates (dNTPs) and analogs thereof can be included in the anchor region including $5'-(\lambda)_n N_m-3'$, where n is an integer in the range of 1 to 20, or greater, and m is an integer in the range of 1-10, or greater, of oligonucleotide primers according to aspects of the present disclosure. The term "nucleotide analog" in this context refers to a modified or non-naturally occurring nucleotide, particularly nucleotide analogs which can be polymerized, with naturally occurring nucleotides and/or non-naturally occurring nucleotides, by template-directed nucleic acid polymerization, or non-template-directed nucleic acid polymerization, catalyzed by a nucleic acid polymerase. Nucleotides and nucleotide analogs are well-known in the art. Particular nucleotide analogs are capable of Watson-Crick pairing via hydrogen bonds with a complementary nucleotide and illustratively include, but are not limited to, naturally-occurring and non-naturally-occurring nucleotides and analogs thereof including those containing an analog of a nucleotide base such as substituted purines or pyrimidines, deazapurines, methylpurines, methylpyrimidines, aminopurines, aminopyrimidines, thiopurines, thiopyrimidines, indoles, pyrroles, 7-deazaguanine, 7-deazaadenine, 7-methylguanine, hypoxanthine, pseudocytosine, pseudoisocytosine, isocytosine, isoguanine, 2-thiopyrimidines, 4-thiothymine, 6-thioguanine, nitropyrrole, nitroindole, and 4-methylindole. Nucleotide analogs include those containing an analog of a deoxyribose such as a substituted deoxyribose, a substituted or non-substituted arabinose, a substituted or non-substituted xylose, and a substituted or non-substituted pyranose. Nucleotide analogs include those containing an analog of a phosphate ester such as phosphorothioates, phosphorodithioates, phosphoroamidates, phosphoroselenoates, phosophoroanilothioates, phosphoroanilidates, phosphoroamidates, boronophosphates, phosphotriesters, and alkylphosphonates such as methylphosphonates.

Non-limiting examples of poly(A)-homopolymer-hybridizing region nucleic acid sequences are shown in Table I below, each including a poly(A)-homopolymer-hybridizing region and an anchor region, 5'-λN-3'.

TABLE I

| Oligonucleotide Primer Name | Sequence |
| --- | --- |
| SEQ ID NO: 1 | 5' X1X1X1X1X1X1X1X1X1X1λn 3' |
| SEQ ID NO: 2 | 5' X1X1X1X1X1X1XIX1X1TλN 3' |
| SEQ ID NO: 3 | 5' X2X2X2X2X2X2X2X2TTλN 3' |
| SEQ ID NO: 4 | 5' X2X2X2X2X2X2X2TTTλN 3' |
| SEQ ID NO: 5 | 5' X2X2X2X2X2TX2TTTλN 3' |
| SEQ ID NO: 6 | 5' X2X2X2X2X2TTTTλN 3' |
| SEQ ID NO: 7 | 5' X2X2X2X2X2X2X2X2X2λN 3' |
| SEQ ID NO: 8 | 5' X2X2X2X2X2X2X2X2TλN 3' |
| SEQ ID NO: 9 | 5' X2X2TX2X2TX2X2TTλN 3' |
| SEQ ID NO: 10 | 5' X1X1X1X1X1X1X1X1TTλN 3' |
| SEQ ID NO: 11 | 5' X1X1X1X1X1X1X1TTTλN 3' |
| SEQ ID NO: 12 | 5' X1X1TX1X1TX1X1TTλN 3' |
| SEQ ID NO: 13 | 5' X1X1X1X1XIXITTTTλN 3' |
| SEQ ID NO: 14 | 5'-X1X1X1X1X1TTTTTλN 3' |
| SEQ ID NO: 15 | 5' X1X1X1X1TTTTTλN 3' |

In Table I, X1=5-hydroxybutynl-2'-deoxyuridine (Super T); and X2=propynyl-deoxyuridine. In these sequences, λ is any nucleotide or nucleotide analog with the proviso that X is not a nucleotide or nucleotide analog complementary to A; N is any nucleotide or nucleotide analog. According to aspects of the present disclosure, an oligonucleotide primer set is provided wherein the oligonucleotide primer set includes 2 or more oligonucleotide primers, such as, 2, 3, 4, 5, 6, 7, 8, 9, 10, 11, 12, or more oligonucleotide primers which have different anchor regions.

According to aspects of the present disclosure, an oligonucleotide primer set is provided wherein the oligonucleotide primer set includes 2 or more oligonucleotide primers, such as, 2, 3, 4, 5, 6, 7, 8, 9, 10, 11, 12, or more oligonucleotide primers wherein the oligonucleotide primers include, from 5' to 3', a homopolymer-hybridizing region, and an anchor region $5'-(\lambda)_n N_m-3'$, where n is an integer in the range of 1 to 20, or greater, and m is an integer in the range of 1-10, or greater, wherein the anchor regions of the oligonucleotide primers differ, wherein the homopolymer-hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the homopolymer-hybridizing region is a contiguous, covalently bonded, linear sequence of the 5 to 20 elements, wherein the homopolymer-hybridizing region hybridizes to a complementary homopolymer tract of a target nucleic acid, wherein the complementary homopolymer tract comprises a contiguous sequence of complementary elements, wherein the complementary elements are complementary to the elements of the homopolymer-hybridizing region, wherein λ is any nucleotide or nucleotide analog with the proviso that λ is not a nucleotide or nucleotide analog complementary to a complementary element of the complementary homopolymer tract, and wherein N is any nucleotide or nucleotide analog.

According to aspects of the present disclosure, an oligonucleotide primer set is provided wherein the oligonucleotide primer set includes at least 12 oligonucleotide primers which have different anchor regions.

According to aspects of the present disclosure, an oligonucleotide primer set is provided wherein the oligonucleotide primer set includes 2 to $1\times10^9$ oligonucleotide primers which have different anchor regions, such as 2, 3, 4, 5, 6, 7, 8, 9, 10, 11, 12, 12 to 36, 12 to 108, 12 to 324, 12 to 972, 1000 to 5000, 1000 to 10,000, 1000 to 100,000, 1000 to 1,000,000, 1000 to 1,000,000,000, or greater.

Oligonucleotide primers of an oligonucleotide primer set according to aspects of the present disclosure include, from 5' to 3', a homopolymer-hybridizing region, and an anchor region 5'-$(λ)_n N_m$-3' which is or includes 5'-$(λ)_1 N_1$-3', wherein the homopolymer-hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the homopolymer-hybridizing region is a contiguous, covalently bonded, linear sequence of the 5 to 20 elements, wherein the homopolymer-hybridizing region hybridizes to a complementary homopolymer tract of a target nucleic acid, wherein the complementary homopolymer tract comprises a contiguous sequence of "complementary elements", wherein the "complementary elements" are complementary to the elements of the homopolymer-hybridizing region, wherein λ is any nucleotide or nucleotide analog with the proviso that λ is not a nucleotide or nucleotide analog complementary to a complementary element of the complementary homopolymer tract.

In an oligonucleotide primer set for use where the complementary elements of the complementary homopolymer tract are "A", i.e. a poly(A) tract, the oligonucleotide primer set according to aspects of the present disclosure includes at least one oligonucleotide primer having an anchor region 5'-$(λ)_n N_m$-3' including 5'-$(λ)_1 N_1$-3' where 5'-$(λ)_1 N_1$-3' is 5'-AA-3', at least one oligonucleotide primer having an anchor region 5'-$(λ)_n N_m$-3' including 5'-$(λ)_1 N_1$-3' where 5'-$(λ)_1 N_1$-3' is 5'-AT-3', at least one oligonucleotide primer having an anchor region 5'-$(λ)_n N_m$-3' including 5'-$(λ)_1 N_1$-3' where 5'-$(λ)_1 N_1$-3' is 5'-AC-3', at least one oligonucleotide primer having an anchor region 5'-$(λ)_n N_m$-3' including 5'-$(λ)_1 N_1$-3' where 5'-$(λ)_1 N_1$-3' is 5'-AG-3', at least one oligonucleotide primer having an anchor region 5'-$(λ)_n N_m$-3' including 5'-$(λ)_1 N_1$-3' where 5'-$(λ)_1 N_1$-3' is 5'-CA-3', at least one oligonucleotide primer having an anchor region 5'-$(λ)_n N_m$-3' including 5'-$(λ)_1 N_1$-3' where 5'-$(λ)_1 N_1$-3' is 5'-CT-3', at least one oligonucleotide primer having an anchor region 5'-$(λ)_n N_m$-3' including 5'-$(λ)_1 N_1$-3' where 5'-$(λ)_1 N_1$-3' is 5'-CC-3', at least one oligonucleotide primer having an anchor region 5'-$(λ)_n N_m$-3' including 5'-$(λ)_1 N_1$-3' where 5'-$(λ)_1 N_1$-3' is 5'-CG-3', at least one oligonucleotide primer having an anchor region 5'-$(λ)_n N_m$-3' including 5'-$(λ)_1 N_1$-3' where 5'-$(λ)_1 N_1$-3' is 5'-GA-3', at least one oligonucleotide primer having an anchor region 5'-$(λ)_n N_m$-3' including 5'-$(λ)_1 N_1$-3' where 5'-$(λ)_1 N_1$-3' is 5'-GT-3', at least one oligonucleotide primer having an anchor region 5'-$(λ)_n N_m$-3' including 5'-$(λ)_1 N_1$-3' where 5'-$(λ)_1 N_1$-3' is 5'-GC-3', and at least one oligonucleotide primer having an anchor region 5'-$(λ)_n N_m$-3' including 5'-$(λ)_1 N_1$-3' where 5'-$(λ)_1 N_1$-3' is 5'-GG-3'. In each case, each of the specified nucleotides of 5'-$(λ)_1 N_1$-3' can be the specified nucleotides or one or both can be a corresponding nucleotide analog.

In an oligonucleotide primer set for use where the complementary elements of the complementary homopolymer tract are "C", i.e. a poly(C) tract, the oligonucleotide primer set according to aspects of the present disclosure includes at least one oligonucleotide primer having an anchor region 5'-$(λ)_n N_m$-3' including 5'-$(λ)_1 N_1$-3' where 5'-$(λ)_1 N_1$-3' is 5'-AA-3', at least one oligonucleotide primer having an anchor region 5'-$(λ)_n N_m$-3' including 5'-$(λ)_1 N_1$-3' where 5'-$(λ)_1 N_1$-3' is 5'-AT-3', at least one oligonucleotide primer having an anchor region 5'-$(λ)_n N_m$-3' including 5'-$(λ)_1 N_1$-3' where 5'-$(λ)_1 N_1$-3' is 5'-AC-3', at least one oligonucleotide primer having an anchor region 5'-$(λ)_n N_m$-3' including 5'-$(λ)_1 N_1$-3' where 5'-$(λ)_1 N_1$-3' is 5'-AG-3', at least one oligonucleotide primer having an anchor region 5'-$(λ)_n N_m$-3' including 5'-$(λ)_1 N_1$-3' where 5'-$(λ)_1 N_1$-3' is 5'-CA-3', at least one oligonucleotide primer having an anchor region 5'-$(λ)_n N_m$-3' including 5'-$(λ)_1 N_1$-3' where 5'-$(λ)_1 N_1$-3' is 5'-CT-3' at least one oligonucleotide primer having an anchor region 5'-$(λ)_n N_m$-3' including 5'-$(λ)_1 N_1$-3' where 5'-$(λ)_1 N_1$-3' is 5'-CC-3', at least one oligonucleotide primer having an anchor region 5'-$(λ)_n N_m$-3' including 5'-$(λ)_1 N_1$-3' where 5'-$(λ)_1 N_1$-3' is 5'-CG-3', at least one oligonucleotide primer where 5'-$(λ)_1 N_1$-3' is 5'-TA-3', at least one oligonucleotide primer having an anchor region 5'-$(λ)_n N_m$-3' including 5'-$(λ)_1 N_1$-3' where 5'-$(λ)_1 N_1$-3' is 5'-TT-3', at least one oligonucleotide primer having an anchor region 5'-$(λ)_n N_m$-3' including 5'-$(λ)_1 N_1$-3' where 5'-$(λ)_1 N_1$-3' is 5'-TC-3', and at least one oligonucleotide primer having an anchor region 5'-$(λ)_n N_m$-3' including 5'-$(λ)_1 N_1$-3' where 5'-$(λ)_1 N_1$-3' is 5'-TG-3'. In each case, each of the specified nucleotides of 5'-$(λ)_1 N_1$-3' can be the specified nucleotides or one or both can be a corresponding nucleotide analog.

In an oligonucleotide primer set for use where the complementary elements of the complementary homopolymer tract are "G", i.e. a poly(G) tract, the oligonucleotide primer set according to aspects of the present disclosure includes at least one oligonucleotide primer having an anchor region 5'-$(λ)_n N_m$-3' including 5'-$(λ)_1 N_1$-3' where 5'-$(λ)_1 N_1$-3' is 5'-AA-3', at least one oligonucleotide primer having an anchor region 5'-$(λ)_n N_m$-3' including 5'-$(λ)_1 N_1$-3' where 5'-$(λ)_1 N_1$-3' is 5'-AT-3', at least one oligonucleotide primer having an anchor region 5'-$(λ)_n N_m$-3' including 5'-$(λ)_1 N_1$-3' where 5'-$(λ)_1 N_1$-3' is 5'-AC-3', at least one oligonucleotide primer having an anchor region 5'-$(λ)_n N_m$-3' including 5'-$(λ)_1 N_1$-3' where 5'-$(λ)_1 N_1$-3' is 5'-AG-3', at least one oligonucleotide primer having an anchor region 5'-$(λ)_n N_m$-3' including 5'-$(λ)_1 N_1$-3' where 5'-$(λ)_1 N_1$-3' is 5'-GA-3', at least one oligonucleotide primer having an anchor region 5'-$(λ)_n N_m$-3' including 5'-$(λ)_1 N_1$-3' where 5'-$(λ)_1 N_1$-3' is 5'-GT-3' at least one oligonucleotide primer having an anchor region 5'-$(λ)_n N_m$-3' including 5'-$(λ)_1 N_1$-3' where 5'-$(λ)_1 N_1$-3' is 5'-GC-3', at least one oligonucleotide primer having an anchor region 5'-$(λ)_n N_m$-3' including 5'-$(λ)_1 N_1$-3' where 5'-$(λ)_1 N_1$-3' is 5'-GG-3', at least one oligonucleotide primer having an anchor region 5'-$(λ)_n N_m$-3' including 5'-$(λ)_1 N_1$-3' where 5'-$(λ)_1 N_1$-3' is 5'-TA-3', at least one oligonucleotide primer having an anchor region 5'-$(λ)$ $_nN_m$-3' including 5'-$(\lambda)_1N_1$-3' where 5'-$(\lambda)_1N_1$-3' is 5'-TT-3', at least one oligonucleotide primer where 5'-$(\lambda)_1N_1$-3' is 5'-TC-3', and at least one oligonucleotide primer having an anchor region 5'-$(\lambda)_nN_m$-3' including 5'-$(\lambda)_1N_1$-3' where 5'-$(\lambda)_1N_1$-3' is 5'-TG-3'. In each case, each of the specified nucleotides of 5'-$(\lambda)_1N_1$-3' can be the specified nucleotides or one or both can be a corresponding nucleotide analog.

In an oligonucleotide primer set for use where the complementary elements of the complementary homopolymer tract are "T", or "U" i.e. a poly(T) tract or a poly(U) tract, the oligonucleotide primer set according to aspects of the present disclosure includes at least one oligonucleotide primer having an anchor region 5'-$(\lambda)_nN_m$-3' including 5'-$(\lambda)_1N_1$-3' where 5'-$(\lambda)_1N_1$-3' is 5'-CA-3', at least one oligonucleotide primer having an anchor region 5'-$(\lambda)_nN_m$-3' including 5'-$(\lambda)_1N_1$-3' where 5'-$(\lambda)_1N_1$-3' is 5'-CT-3', at least one oligonucleotide primer having an anchor region 5'-$(\lambda)_nN_m$-3' including 5'-$(\lambda)_1N_1$-3' where 5'-$(\lambda)_1N_1$-3' is 5'-CC-3', at least one oligonucleotide primer where 5'-$(\lambda)_1N_1$-3' is 5'-CG-3', at least one oligonucleotide primer having an anchor region 5'-$(\lambda)_nN_m$-3' including 5'-$(\lambda)_1N_1$-3' where 5'-$(\lambda)_1N_1$-3' is 5'-GA-3', at least one oligonucleotide primer having an anchor region 5'-$(\lambda)_nN_m$-3' including 5'-$(\lambda)_1N_1$-3' where 5'-$(\lambda)_1N_1$-3' is 5'-GT-3' at least one oligonucleotide primer having an anchor region 5'-$(\lambda)_nN_m$-3' including 5'-$(\lambda)_1N_1$-3' where 5'-$(\lambda)_1N_1$-3' is 5'-GC-3', at least one oligonucleotide primer having an anchor region 5'-$(\lambda)_nN_m$-3' including 5'-$(\lambda)_1N_1$-3' where 5'-$(\lambda)_1N_1$-3' is 5'-GG-3', at least one oligonucleotide primer having an anchor region 5'-$(\lambda)_nN_m$-3' including 5'-$(\lambda)_1N_1$-3' where 5'-$(\lambda)_1N_1$-3' is 5'-TA-3', at least one oligonucleotide primer having an anchor region 5'-$(\lambda)_nN_m$-3' including 5'-$(\lambda)_1N_1$-3' where 5'-$(\lambda)_1N_1$-3' is 5'-TT-3', at least one oligonucleotide primer having an anchor region 5'-$(\lambda)_nN_m$-3' including 5'-$(\lambda)_1N_1$-3' where 5'-$(\lambda)_1N_1$-3' is 5'-TC-3', and at least one oligonucleotide primer having an anchor region 5'-$(\lambda)_nN_m$-3' including 5'-$(\lambda)_1N_1$-3' where 5'-$(\lambda)_1N_1$-3' is 5'-TG-3'. In each case, each of the specified nucleotides of 5'-$(\lambda)_1N_1$-3' can be the specified nucleotides or one or both can be a corresponding nucleotide analog.

Optionally included is a primer tag sequence (PTS) in oligonucleotide primers of an oligonucleotide set. The term "starting nucleic acid" as used herein refers to nucleic acid, for example, DNA generally such as genomic DNA, mtDNA, DNA fragments, naturally occurring DNA, synthetic DNA, and RNA generally such as intact mRNA, fragmented mRNA, coding RNA, non-coding RNA, small RNA, miRNA, naturally occurring RNA, and synthetic RNA.

The starting nucleic acid, such as DNA or RNA, can be obtained from any source, including, but not limited to, a human, a non-human mammal, a vertebrate, an invertebrate, a microorganism, or a plant. The starting nucleic acid, such as DNA or RNA, can be obtained from one or more cells ex vivo or in vitro. For example, the starting nucleic acid, such as DNA or RNA, can be obtained from cultured cells, including, but not limited to, cell lines, primary cells or laboratory manipulated cells such as recombinant cells.

The starting nucleic acid, such as DNA or RNA, is typically contained within a biological sample, which can be obtained from an individual, such as from a bodily sample, for example, blood, buccal swab, skin tissue, urine, saliva, tissue, and the like, and cell lines derived therefrom. A prenatal sample can be obtained from amniotic fluid, products of conception, blastocysts and blastomeres, corionic villi, fetal cells, fetal DNA, and/or fetal RNA circulating in maternal blood. Samples also be obtained from in vitro sources such as cell lines.

Biological samples can be obtained from any source, including, but not limited to, a human, a non-human mammal, a vertebrate, an invertebrate, a microorganism, or a plant. Biological samples can be obtained from one or more cells ex vivo or in vitro. For example, biological samples can be obtained from cultured cells, including, but not limited to, cell lines, primary cells or laboratory manipulated cells such as recombinant cells.

Starting nucleic acid, such as DNA or RNA, is obtained by methods known in the art, for instance, as described in J. Sambrook and D. W. Russell, Molecular Cloning: A Laboratory Manual, Cold Spring Harbor Laboratory Press; 3rd Ed., 2001 or F. M. Ausubel, Ed., Short Protocols in Molecular Biology, Current Protocols; 5th Ed., 2002. Starting nucleic acid may also be obtained commercially and/or using commercial kits for isolation of starting nucleic acid.

The term "target nucleic acid" as used herein refers to nucleic acid to be annealed with an oligonucleotide primer of the present disclosure. The target nucleic acid may be identical to a "starting nucleic acid" or may be processed to yield a product amenable to a particular procedure. According to particular aspects of the present disclosure, target nucleic acid is fragmented, such as by enzymatic digestion of larger nucleic acids, and the resulting fragments are modified to include a homopolymer tract. The resulting fragments are polyadenylated to add a poly(A) tract according to aspects of the present disclosure, such as by enzymatic polyadenylation such as by poly(A) polymerase. Alternatively, a poly(U) tract is added to the resulting fragments according to aspects of the present disclosure, such as by enzymatic polyuridylation such as by a poly(U) polymerase. As a further alternative, a poly(C), a poly(T), or a poly(G) tract is added to the resulting fragments according to aspects of the present disclosure, such as by enzymatic polycytidylation, polythymidylation, or polyguanidylation such as by an appropriate polymerase, such as, but not limited to, a poly(C) polymerase or poly(G) polymerase. As a further alternative, a poly(A) polymerase can be used to add a poly(U), poly(C), or poly(G) tract, albeit with lower efficiency than for a poly(A) tract.

Methods and oligonucleotides described herein may be used to generate libraries from nucleic acids of any of various organisms including, but not limited to, humans, non-human primates, rodents, rabbits, dogs, cats, horses, cattle, pigs, goats and sheep. Non-mammalian sources of sample nucleic acid can also be used, illustratively including fish and other aquatic organisms, birds, poultry, bacteria, viruses, plants, insects, reptiles, amphibians, fungi and mycobacteria. Thus, target nucleic acid, such as target DNA or target RNA, may be obtained from any of these sources.

Oligonucleotide primers are provided according to the present disclosure which include, from 5' to 3', a PTS region, a homopolymer-hybridizing region and an anchor region, the anchor region including 5'-$(\lambda)_nN_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein the homopolymer-hybridizing region hybridizes to a complementary homopolymer tract of a target nucleic acid, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein λ is any nucleotide or nucleotide analog with the proviso that λ is not a nucleotide or nucleotide analog complementary to a complementary element of the complementary homopolymer tract, and wherein N is any nucleotide or nucleotide analog.

According to aspects, oligonucleotide primers are provided according to the present disclosure which include, from 5' to 3', an optional PTS region, a homopolymer-hybridizing region, and an anchor region including 5'-(λ)$_n$N$_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or T$_m$ increasing nucleotide analogs, wherein the homopolymer-hybridizing region hybridizes to a complementary homopolymer tract of a target RNA, and wherein 5, 6, or 7 of the elements are T$_m$ increasing nucleotide analogs.

According to aspects, oligonucleotide primers are provided according to the present disclosure which include, from 5' to 3', an optional PTS region, a homopolymer-hybridizing region, and an anchor region including 5'-(λ)$_n$N$_m$-3', where n is an integer in the range of 1 to 20, or greater, and m is an integer in the range of 1-10, or greater, wherein the homopolymer-hybridizing region is a contiguous sequence of 5 to 12 elements, 5 to 11 elements, 5 to 10 elements, 6 to 12 elements, 6 to 11 elements, 6 to 10 elements, 7 to 12 elements, 7 to 11 elements, 7 to 12 elements, 8 to 12 elements, 8 to 11 elements, 8 to 10 elements, 9 to 12 elements, 9 to 11 elements, 9 to 10 elements, or 10 elements, wherein 5, 6, 7, 8, 9, 10, 11, or 12 of the elements are T$_m$ increasing nucleotide analogs.

Oligonucleotides according to aspects of the present disclosure are generated synthetically using chemical synthetic and/or recombinant molecular biology techniques for example as detailed in Herdewijn, P. (Ed.), Oligonucleotide Synthesis: Methods and Applications, Methods in Molecular Biology, Humana Press, 2004.

Methods of generating a sequencing library are provided according to the present disclosure which include providing an oligonucleotide primer which includes, from 5' to 3', an optional PTS region, a homopolymer-hybridizing region, and an anchor region including 5'-(λ)$_n$N$_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or T$_m$ increasing nucleotide analogs, wherein the homopolymer-hybridizing region hybridizes to a complementary homopolymer tract of a target nucleic acid, wherein at least 4, and up to 20, of the elements are T$_m$ increasing nucleotide analogs, wherein the complementary homopolymer tract comprises a contiguous sequence of complementary elements, wherein λ is any nucleotide or nucleotide analog with the proviso that X is not a nucleotide or nucleotide analog complementary to a complementary element of the homopolymer tract, and wherein N is any nucleotide or nucleotide analog.

Methods of generating a sequencing library are provided according to the present disclosure which include providing an oligonucleotide primer which includes, from 5' to 3', an optional primer tag sequence, a homopolymer-hybridizing region, and an optional anchor region including 5'-(λ)$_n$N$_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or T$_m$ increasing nucleotide analogs, wherein at least 4 of the elements are T$_m$ increasing nucleotide analogs, wherein the homopolymer hybridizing region hybridizes to a complementary homopolymer tract of a target nucleic acid, wherein the complementary homopolymer tract comprises a contiguous sequence of complementary elements, wherein λ is any nucleotide or nucleotide analog with the proviso that X is not a nucleotide or nucleotide analog complementary to an complementary element of the complementary homopolymer tract, and wherein N is any nucleotide or nucleotide analog.

Methods of generating a sequencing library are provided according to the present disclosure which include providing an oligonucleotide primer set which includes 2 or more oligonucleotide primers, such as 2, 3, 4, 5, 6, 7, 8, 9, 10, 11, 12, or more oligonucleotide primers wherein each oligonucleotide primer includes, from 5' to 3', an optional primer tag sequence, a homopolymer-hybridizing region, and an anchor region including 5'-(λ)$_n$N$_m$-3', where n is an integer in the range of 1 to 20, or greater, and m is an integer in the range of 1-10, or greater, wherein the anchor region of the two or more oligonucleotide primers differs, wherein the homopolymer-hybridizing region is a contiguous sequence of 5 to 20 elements, wherein the elements are nucleotides or T$_m$ increasing nucleotide analogs, wherein at least 4 of the elements are T$_m$ increasing nucleotide analogs, wherein the homopolymer hybridizing region hybridizes to a complementary homopolymer tract of a target nucleic acid, wherein the complementary homopolymer tract comprises a contiguous sequence of complementary elements, wherein λ is any nucleotide or nucleotide analog with the proviso that λ is not a nucleotide or nucleotide analog complementary to an complementary element of the complementary homopolymer tract, and wherein N is any nucleotide or nucleotide analog.

Methods of generating a sequencing library are provided according to the present disclosure which include providing an oligonucleotide primer set wherein the oligonucleotide primer set includes at least 12 oligonucleotide primers.

Methods of generating a sequencing library are provided according to the present disclosure which include providing an oligonucleotide primer set according to aspects of the present disclosure which includes two or more oligo nucleotide primers, where each oligonucleotide primer includes, from 5' to 3', a homopolymer-hybridizing region, and an anchor region 5'-(λ)$_n$N$_m$-3' including at least 5'-(λ)$_1$N$_1$-3', wherein the anchor region of the 2 or more oligonucleotide primers differs, wherein the homopolymer-hybridizing region is a contiguous sequence of 5 to 20 elements, wherein the elements are nucleotides or T$_m$ increasing nucleotide analogs, wherein at least 4, and up to 20, such as 4, 5, 6, 7, 8, 9, 10, 11, 12, 13, 14, 15, 16, 17, 18, 19, or 20, of the elements are T$_m$ increasing nucleotide analogs, wherein the homopolymer-hybridizing region is a contiguous, covalently bonded, linear sequence of the 5 to 20 elements, wherein the homopolymer-hybridizing region hybridizes to a complementary homopolymer tract of a target nucleic acid, wherein the complementary homopolymer tract comprises a contiguous sequence of "complementary elements", wherein the "complementary elements" are complementary to the elements of the homopolymer-hybridizing region, wherein λ is any nucleotide or nucleotide analog with the proviso that λ is not a nucleotide or nucleotide analog complementary to a complementary element of the complementary homopolymer tract. Methods of generating a sequencing library are provided according to the present disclosure which include providing an oligonucleotide primer set according to aspects of the present disclosure for use where the complementary elements of the complementary homopolymer tract are "A", i.e. a poly(A) tract, wherein the primer set according to aspects of the present disclosure includes at least one oligonucleotide primer having an anchor region 5'-$(\lambda)_n N_m$-3' including 5'-$(\lambda)_1 N_1$-3' where 5'-$(\lambda)_1 N_1$-3' is 5'-AA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CT-3' at least one oligonucleotide primer having an anchor region 5'-$(\lambda)_n N_m$-3' including 5'-$(\lambda)_1 N_1$-3' where 5'-$(\lambda)_1 N_1$-3' is 5'-CC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GC-3', and at least one oligonucleotide primer having an anchor region 5'-$(\lambda)_n N_m$-3' including 5'-$(\lambda)_1 N_1$-3' where 5'-$(\lambda)_1 N_1$-3' is 5'-GG-3'. In each case, each of the specified nucleotides of 5'-$(\lambda)_1 N_1$-3' can be the specified nucleotides or one or both can be a corresponding nucleotide analog.

Methods of generating a sequencing library are provided according to the present disclosure which include providing an oligonucleotide primer set according to aspects of the present disclosure for use where the complementary elements of the complementary homopolymer tract are "C", i.e. a poly(C) tract, wherein the oligonucleotide primer set according to aspects of the present disclosure includes at least one oligonucleotide primer where 5'-$(\lambda)_1 N_1$-3' is 5'-AA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CT-3' at least one oligonucleotide primer having an anchor region 5'-$(\lambda)_n N_m$-3' including 5'-$(\lambda)_1 N_1$-3' where 5'-$(\lambda)_1 N_1$-3' is 5'-CC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TA-3', at least one oligonucleotide primer where 5'-$(\lambda)_1 N_1$-3' is 5'-TT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TC-3', and at least one oligonucleotide primer having an anchor region 5'-$(\lambda)_n N_m$-3' including 5'-$(\lambda)_1 N_1$-3' where 5'-$(\lambda)_1 N_1$-3' is 5'-TG-3'. In each case, each of the specified nucleotides of 5'-$(\lambda)_1 N_1$-3' can be the specified nucleotides or one or both can be a corresponding nucleotide analog.

Methods of generating a sequencing library are provided according to the present disclosure which include providing an oligonucleotide primer set according to aspects of the present disclosure for use where the complementary elements of the complementary homopolymer tract are "G", i.e. a poly(G) tract, wherein the oligonucleotide primer set according to aspects of the present disclosure includes at least one oligonucleotide primer having an anchor region 5'-$(\lambda)_n N_m$-3' including 5'-$(\lambda)_1 N_1$-3' where 5'-$(\lambda)_1 N_1$-3' is 5'-AA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GT-3' at least one oligonucleotide primer having an anchor region 5'-$(\lambda)_n N_m$-3' including 5'-$(\lambda)_1 N_1$-3' where 5'-$(\lambda)_1 N_1$-3' is 5'-GC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TC-3', and at least one oligonucleotide primer having an anchor region 5'-$(\lambda)_n N_m$-3' including 5'-$(\lambda)_1 N_1$-3' where 5'-$(\lambda)_1 N_1$-3' is 5'-TG-3'. In each case, each of the specified nucleotides of 5'-$(\lambda)_1 N_1$-3' can be the specified nucleotides or one or both can be a corresponding nucleotide analog.

Methods of generating a sequencing library are provided according to the present disclosure which include providing an oligonucleotide primer set according to aspects of the present disclosure for use where the complementary elements of the complementary homopolymer tract are "T", or "U" i.e. a poly(T) tract or a poly(U) tract, wherein the oligonucleotide primer set according to aspects of the present disclosure includes at least one oligonucleotide primer having an anchor region 5'-$(\lambda)_n N_m$-3' including 5'-$(\lambda)_1 N_1$-3' where 5'-$(\lambda)_1 N_1$-3' is 5'-CA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GT-3' at least one oligonucleotide primer having an anchor region 5'-$(\lambda)_n N_m$-3' including 5'-$(\lambda)_1 N_1$-3' where 5'-$(\lambda)_1 N_1$-3' is 5'-GC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TT-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-TC-3', and at least one oligonucleotide primer having an anchor region 5'-$(\lambda)_n N_m$-3' including 5'-$(\lambda)_1 N_1$-3' where 5'-(λ)₁N₁-3' is 5'-TG-3'. In each case, each of the specified nucleotides of 5'-(λ)₁N₁-3' can be the specified nucleotides or one or both can be a corresponding nucleotide analog.

The term "oligonucleotide primer" as used herein refers to an oligonucleotide capable of acting as a point of initiation of enzymatic synthesis of an oligonucleotide primer extension product under conditions in which synthesis of an oligonucleotide primer extension product which is complementary to a target nucleic acid is induced. Such conditions include the presence of nucleotides and a suitable polymerase, at a suitable temperature and pH.

According to aspects of methods of the present disclosure, the method includes annealing the oligonucleotide primer, or oligonucleotide primer set, to target nucleic acid; and extending the primer, producing a complementary strand complementary to the target nucleic acid, producing double-stranded nucleic acid.

Figure 12:
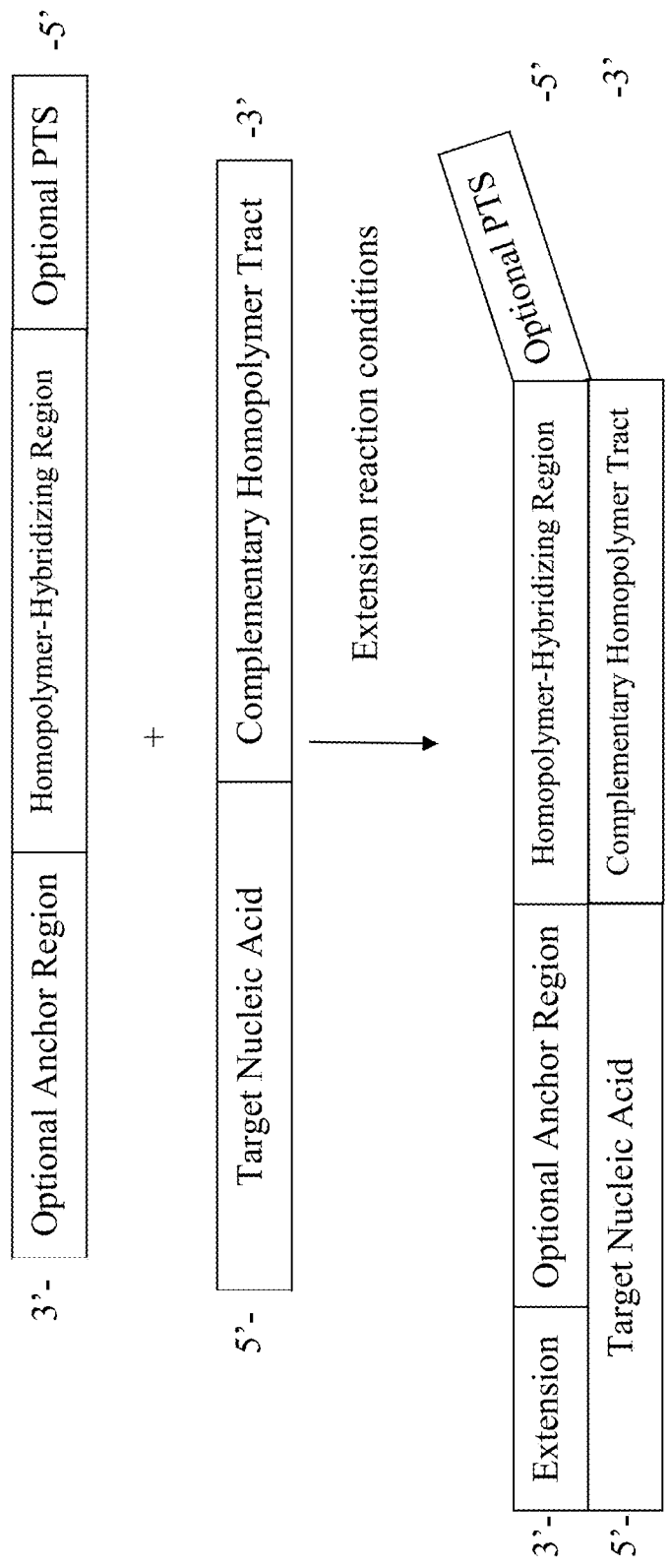
FIG. 12 is a schematic diagram illustrating methods according to aspects of the present disclosure.

FIG. 12 illustrates methods according to aspects of the present disclosure.

According to aspects of methods of the present disclosure, the method includes annealing the oligonucleotide primer, or oligonucleotide primer set, to target RNA; and reverse transcribing the target RNA, producing a first strand complementary DNA (cDNA) which is complementary to the target RNA.

Annealing the oligonucleotide primer, or oligonucleotide primer set, to the target nucleic acid is performed at an annealing temperature. The annealing temperature depends on factors, including the nucleic acid sequence of the oligonucleotide primer, or primers, and the target nucleic acid, and the composition of the reaction medium, including factors such as salt concentration, and concentration of additives, such as but not limited to, formamide, betaine, polyethylene glycol, SDS, and DMSO. Typically, the annealing temperature is in the range of 30° C. to 65° C., but can be higher or lower. The annealing temperature may be higher or lower than the oligo melting temperature ($T_m$). Often annealing temperatures are higher than the $T_m$ of the oligo to improve the stringency of the reaction.

Primer extension, producing a first strand complementary DNA, is accomplished using a polymerase enzyme under extension reaction conditions compatible with the polymerase activity to produce a complementary strand. Particular conditions and protocols for primer extension are detailed in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002.

Reverse transcribing target RNA, producing first strand complementary DNA (cDNA), is accomplished using a reverse transcriptase enzyme under reaction conditions compatible with reverse transcriptase enzyme activity to transcribe the target RNA. Particular conditions and protocols for reverse transcription are detailed in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002.

Methods of generating a sequencing library are provided according to the present disclosure which further include polymerizing a second strand of DNA complementary to the first strand cDNA, producing double-stranded cDNA. Polymerizing a second strand of DNA complementary to the first strand cDNA may include providing an appropriate DNA polymerase and polymerizing to produce double-stranded cDNA under reaction conditions compatible with DNA polymerase activity to produce double-stranded cDNA.

Suitable polymerases may include bacterial DNA polymerases, eukaryotic DNA polymerases, archaeal DNA polymerases, viral DNA polymerases, Taq polymerase, DNA polymerase I, T4 DNA polymerase, Pfu polymerase, and phage DNA polymerases, including the Klenow fragment of DNA polymerase I, SEQUENASE 1.0 and SEQUENASE 2.0 (U.S. Biochemical), T5 DNA polymerase, and Phi29 DNA polymerase, among others.

Methods of generating a library are provided according to the present disclosure which include amplifying the produced double-stranded nucleic acid.

The terms "amplify, "amplification," and "amplifying" are used to refer generally to a process of copying a nucleic acid molecule, or portion thereof, to produce at least one copy of the nucleic acid, or portion thereof.

Amplification of template DNA is achieved using an in vitro amplification method. The terms "amplify," "amplification," and "amplifying" are used to refer generally to a method or technique for copying a template nucleic acid, thereby producing nucleic acids including copies of all or a portion of the template nucleic acid, the produced nucleic acids also termed amplicons.

Amplification methods illustratively including PCR, ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

Amplicons optionally contain nucleic acid sequences present in the primers and not present in the original DNA template. Such primer-derived nucleic acids add functionality such as primer binding sites for additional amplification reactions and/or a functional group for chemical bonding to a substrate. Non-limiting examples of primer-derived nucleic acid sequences that can be incorporated into amplicons, and thereby incorporated into the library produced, include, universal sequences, adapters, index sequences, identification sequences, detection sequences, sorting sequences, captures sequences, restriction enzyme cleavage sites, sequencing primer binding site sequences, and amplification primer binding site sequences.

The term "universal sequence" refers to a nucleic acid sequence that is present in a plurality of nucleic acid molecules that also contain nucleic acid sequences which are not common to the plurality of nucleic acid molecules. A universal sequence allows the plurality of nucleic acid molecules to share a common functional aspect, such as binding to a particular primer or capture moiety. Non-limiting examples of universal extension primer binding sites include sequences that are identical to or complementary to P5 and P7 primers. P5 and P7 primers, their complements, and uses, such as in flow cells for capture on a flow cells substrate for next generation sequencing (NGS), are known in the art, for example as detailed in WO2015106941.

An index sequence is incorporated into amplicons during library preparation according to aspects of the present disclosure. An index sequence is a unique nucleic acid sequence common to a set of amplicons, e.g. to identify the set of amplicons as originating from a particular source. Index sequences allow for multiplexing since multiple nucleic acids from different sources can be pooled for sequencing and later can be "demultiplexed" for data analysis if desired.

Sequencing of amplicons is accomplished using any of various sequencing methodologies, including, traditional Sanger sequencing and massively parallel sequencing methodologies ("next generation sequencing").

Advantageously, paired end reads are performed. The term "paired end reads" refers to a sequencing technique including one sequencing "read" from each end of an amplicon to be sequenced. This allows for a greater yield of sequencing data and increased confidence in the sequencing results.

Kits are provided according to aspects of the disclosure which include an oligonucleotide primer which includes, from 5' to 3', a homopolymer-hybridizing region, and an anchor region comprising 5'-($\lambda$)$_n$N$_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements, wherein $\lambda$ is any nucleotide or nucleotide analog with the proviso that $\lambda$ is not a nucleotide or nucleotide analog complementary to an complementary element of the complementary homopolymer tract, and wherein N is any nucleotide or nucleotide analog. Optionally, an included oligonucleotide primer includes from 5' to 3', a PTS, a homopolymer-hybridizing region, and an anchor region comprising 5'-($\lambda$)$_n$N$_m$-3', where n is an integer in the range of 1 to 20, or greater, and m is an integer in the range of 1-10, or greater.

As stated, the homopolymer-hybridizing region is a contiguous, covalently bonded, linear, sequence of the 5 to 20 elements wherein the elements are nucleotides or $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements that are complementary to the elements. The contiguous sequence of complementary elements can be polyadenylic acid (poly(A)) sequence according to aspects of the present disclosure. The contiguous sequence of complementary elements can be a polyuridylic acid (poly(U)) sequence according to aspects of the present disclosure. The contiguous sequence of complementary elements can be a polyguanylic acid (poly(G)) sequence according to aspects of the present disclosure. The contiguous sequence of complementary elements can be a polycytidylic acid (poly(C)) sequence according to aspects of the present disclosure. The contiguous sequence of complementary elements can be a polythymidylic acid (poly(T)) sequence according to aspects of the present disclosure.

Kits are provided according to aspects of the disclosure which include an oligonucleotide primer which includes, from 5' to 3', a poly(A)-homopolymer-hybridizing region, and an anchor region including 5'-($\lambda$)$_n$N$_m$-3', where n is an integer in the range of 1 to 20, or greater, and m is an integer in the range of 1-10, or greater, wherein the poly(A)-homopolymer-hybridizing region is a contiguous sequence of 5 to 20 elements, wherein the elements are nucleotides or $T_m$ increasing nucleotide analogs, wherein the poly(A) homopolymer-hybridizing region hybridizes to a poly(A) homopolymer tract of a target nucleic acid, wherein at least 4, and up to 20, of the elements are $T_m$ increasing nucleotide analogs.

Kits are provided according to aspects of the disclosure which include an oligonucleotide primer which includes, from 5' to 3', a PTS, a poly(A)-homopolymer-hybridizing region, and an anchor region including 5'-($\lambda$)$_n$N$_m$-3', where n is an integer in the range of 1 to 20, or greater, and m is an integer in the range of 1-10, or greater, wherein the poly(A)-homopolymer-hybridizing region is a contiguous sequence of 5 to 20 elements, wherein the elements are nucleotides or $T_m$ increasing nucleotide analogs, wherein the poly(A)-homopolymer-hybridizing region hybridizes to a poly(A) homopolymer tract of a target RNA, wherein at least 4, and up to 20, of the elements are $T_m$ increasing nucleotide analogs.

Kits are provided according to aspects of the disclosure which include an oligonucleotide primer which includes, from 5' to 3', a poly(A)-homopolymer-hybridizing region, and an anchor region including 5'-($\lambda$)$_n$N$_m$-3', where n is an integer in the range of 1 to 20, or greater, and m is an integer in the range of 1-10, or greater, wherein the poly(A) homopolymer-hybridizing region is a contiguous sequence of 5 to 15 elements, wherein the elements are nucleotides or $T_m$ increasing nucleotide analogs, wherein the poly(A) homopolymer-hybridizing region hybridizes to a poly(A) homopolymer tract of a target nucleic acid, wherein at least 4, and up to 15, of the elements are $T_m$ increasing nucleotide analogs.

Kits are provided according to aspects of the disclosure which include an oligonucleotide primer which includes, from 5' to 3', a PTS, a poly(A) homopolymer-hybridizing region, and an anchor region including 5'-($\lambda$)$_n$N$_m$-3', where n is an integer in the range of 1 to 20, or greater, and m is an integer in the range of 1-10, or greater, wherein the poly(A) homopolymer-hybridizing region is a contiguous sequence of 5 to 15 elements, wherein the elements are nucleotides or $T_m$ increasing nucleotide analogs, wherein the poly(A) homopolymer-hybridizing region hybridizes to a poly(A) homopolymer tract of a target RNA, wherein at least 4, and up to 15, of the elements are $T_m$ increasing nucleotide analogs.

Kits are provided according to aspects of the disclosure which include an oligonucleotide primer which includes, from 5' to 3', a poly(U)-, a poly(C)-, a poly (G)-, or a poly(T)-homopolymer-hybridizing region, and an anchor region including 5'-($\lambda$)$_n$N$_m$-3', where n is an integer in the range of 1 to 20, or greater, and m is an integer in the range of 1-10, or greater, wherein the poly(U)-, poly(C)-, poly (G)-, or poly(T)-homopolymer-hybridizing region is a contiguous sequence of 5 to 20 elements, such as 5, 6, 7, 8, 9, 10, 11, 12, 13, 14, 15, 16, 17, 18, 19, or 20 elements, wherein the elements are nucleotides or $T_m$ increasing nucleotide analogs, wherein the poly(U)-, poly(C)-, poly (G)-, or poly (T)-homopolymer-hybridizing region hybridizes to a poly (U)-, poly(C)-, poly (G)-, or poly(T)-homopolymer tract of a target nucleic acid, wherein at least 4, and up to 20, of the elements are $T_m$ increasing nucleotide analogs.

Kits are provided according to aspects of the disclosure which include an oligonucleotide primer which includes, from 5' to 3', a PTS, a poly(U)-, a poly(C)-, a poly (G)-, or a poly(T)-homopolymer-hybridizing region, and an anchor region including 5'-($\lambda$)$_n$N$_m$-3', where n is an integer in the range of 1 to 20, or greater, and m is an integer in the range of 1-10, or greater, wherein the poly(U)-, poly(C)-, poly (G)-, or poly(T)-homopolymer-hybridizing region is a contiguous sequence of 5 to 20 elements, such as 5, 6, 7, 8, 9, 10, 11, 12, 13, 14, 15, 16, 17, 18, 19, or 20 elements, wherein the elements are nucleotides or $T_m$ increasing nucleotide analogs, wherein the poly(U)-, poly(C)-, poly (G)-, or poly (T)-homopolymer-hybridizing region hybridizes to a poly (A) homopolymer tract of a target RNA, wherein at least 4, and up to 20, of the elements are $T_m$ increasing nucleotide analogs.

Kits are provided according to aspects of the disclosure which include an oligonucleotide primer which includes, from 5' to 3', a poly(U)-, poly(C)-, poly (G)-, or poly(T)-homopolymer-hybridizing region, and an anchor region including 5'-$(\lambda)_n N_m$-3', where n is an integer in the range of 1 to 20, or greater, and m is an integer in the range of 1-10, or greater, wherein the poly(U)-, poly(C)-, poly (G)-, or poly(T)-homopolymer-hybridizing region is a contiguous sequence of 5 to 15 elements, such as 5, 6, 7, 8, 9, 10, 11, 12, 13, 14, or 15 elements, wherein the elements are nucleotides or $T_m$ increasing nucleotide analogs, wherein the poly (U)-, poly(C)-, poly (G)-, or poly(T)-homopolymer-hybridizing region hybridizes to a poly(U)-, poly(C)-, poly (G)-, or poly(T)-homopolymer tract of a target nucleic acid, wherein at least 4, and up to 15, of the elements are $T_m$ increasing nucleotide analogs.

Kits are provided according to aspects of the disclosure which include an oligonucleotide primer which includes, from 5' to 3', a PTS, a poly(U)-, poly(C)-, poly (G)-, or poly(T)-homopolymer-hybridizing region, and an anchor region including 5'-$(\lambda)_n N_m$-3', where n is an integer in the range of 1 to 20, or greater, and m is an integer in the range of 1-10, or greater, wherein the poly(U)-, poly(C)-, poly (G)-, or poly(T)-homopolymer-hybridizing region is a contiguous sequence of 5 to 15 elements, such as 5, 6, 7, 8, 9, 10, 11, 12, 13, 14, or 15 elements, wherein the elements are nucleotides or $T_m$ increasing nucleotide analogs, wherein the poly(U)-, poly(C)-, poly (G)-, or poly(T)-homopolymer-hybridizing region hybridizes to a poly(U)-, poly(C)-, poly (G)-, or poly(T)-) homopolymer tract of a target RNA, wherein at least 4, and up to 15, of the elements are $T_m$ increasing nucleotide analogs.

Kits are provided according to aspects of the disclosure which include an oligonucleotide primer set, wherein the oligonucleotide primer set includes 2 or more oligonucleotide primers, such as, 2, 3, 4, 5, 6, 7, 8, 9, 10, 11, 12, or more oligonucleotide primers which have different anchor regions.

Kits are provided according to aspects of the disclosure which include an oligonucleotide primer set, wherein the oligonucleotide primer set includes 2 or more oligonucleotide primers, such as, 2, 3, 4, 5, 6, 7, 8, 9, 10, 11, 12, or more oligonucleotide primers wherein the oligonucleotide primers include, from 5' to 3', a homopolymer-hybridizing region, and an anchor region 5'-$(\lambda)_n N_m$-3', where n is an integer in the range of 1 to 20, or greater, and m is an integer in the range of 1-10, or greater, wherein the anchor regions of the oligonucleotide primers differ, wherein the homopolymer-hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the homopolymer-hybridizing region is a contiguous, covalently bonded, linear sequence of the 5 to 20 elements, wherein the homopolymer-hybridizing region hybridizes to a complementary homopolymer tract of a target nucleic acid, wherein the complementary homopolymer tract comprises a contiguous sequence of "complementary elements", wherein the "complementary elements" are complementary to the elements of the homopolymer-hybridizing region, wherein $\lambda$ is any nucleotide or nucleotide analog with the proviso that $\lambda$ is not a nucleotide or nucleotide analog complementary to a complementary element of the complementary homopolymer tract, and wherein N is any nucleotide or nucleotide analog.

Kits are provided according to aspects of the disclosure which include an oligonucleotide primer set, wherein the oligonucleotide primer set includes at least 12 oligonucleotide primers which have different anchor regions.

Kits are provided according to aspects of the disclosure which include an oligonucleotide primer set including at least 12 or more oligonucleotide primers, wherein each oligonucleotide primer of an oligonucleotide primer set according to aspects of the present disclosure includes, from 5' to 3', a homopolymer-hybridizing region, and an anchor region 5'-$(\lambda)_n N_m$-3' including at least 5'-$(\lambda)_1 N_1$-3', wherein the anchor regions of the oligonucleotide primers differ, wherein the homopolymer-hybridizing region is a contiguous sequence of 5 to 20 elements, wherein the elements are nucleotides or $T_m$ increasing nucleotide analogs, wherein at least 4, and up to 20, such as 4, 5, 6, 7, 8, 9, 10, 11, 12, 13, 14, 15, 16, 17, 18, 19, or 20, of the elements are $T_m$ increasing nucleotide analogs, wherein the homopolymer-hybridizing region is a contiguous, covalently bonded, linear sequence of the 5 to 20 elements, wherein the homopolymer-hybridizing region hybridizes to a complementary homopolymer tract of a target nucleic acid, wherein the complementary homopolymer tract comprises a contiguous sequence of "complementary elements", wherein the "complementary elements" are complementary to the elements of the homopolymer-hybridizing region, wherein $\lambda$ is any nucleotide or nucleotide analog with the proviso that $\lambda$ is not a nucleotide or nucleotide analog complementary to a complementary element of the complementary homopolymer tract.

Kits are provided according to aspects of the disclosure which include an oligonucleotide primer set including at least 12 or more oligonucleotide primers for use where the complementary elements are "A", i.e. a poly(A) tract, then each oligonucleotide primer set according to aspects of the present disclosure includes at least one oligonucleotide primer having an anchor region 5'-$(\lambda)_n N_m$-3' including 5'-$(\lambda)_1 N_1$-3' where 5'-$(\lambda)_1 N_1$-3' is 5'-AA-3', at least one oligonucleotide primer where 5'-$(\lambda)_1 N_1$-3' is 5'-AT/U-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-AG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CT/U-3' at least one oligonucleotide primer having an anchor region 5'-$(\lambda)_n N_m$-3' including 5'-$(\lambda)_1 N_1$-3' where 5'-$(\lambda)_1 N_1$-3' is 5'-CC-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-CG-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GA-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GT/U-3', at least one oligonucleotide primer having an anchor region 5'-$(\lambda)_n N_m$-3' including 5'-$(\lambda)_1 N_1$-3' where 5'-$(\lambda)_1 N_1$-3' is 5'-GC-3', and at least one oligonucleotide primer having an anchor region 5'-$(\lambda)_n N_m$-3' including 5'-$(\lambda)_1 N_1$-3' where 5'-$(\lambda)_1 N_1$-3' is 5'-GG-3'. In each case, each of the specified nucleotides of 5'-(λ)$_1$N$_1$-3' can be the specified nucleotides or one or both can be a corresponding nucleotide analog.

Kits are provided according to aspects of the disclosure which include an oligonucleotide primer set including at least 12 or more oligonucleotide primers for use where the complementary elements are "C", i.e. a poly(C) tract, then each oligonucleotide primer set according to aspects of the present disclosure includes at least one oligonucleotide primer having an anchor region 5'-(λ)$_n$N$_m$-3' including 5'-(λ)$_1$N$_1$-3' where 5'-(λ)$_1$N$_1$-3' is 5'-AA-3', at least one oligonucleotide primer having an anchor region 5'-(λ)$_n$N$_m$-3' including 5'-(λ)$_1$N$_1$-3' where 5'-(λ)$_1$N$_1$-3' is 5'-AT/U-3', at least one oligonucleotide primer having an anchor region 5'-(λ)$_n$N$_m$-3' including 5'-(λ)$_1$N$_1$-3' where 5'-(λ)$_1$N$_1$-3' is 5'-AC-3', at least one oligonucleotide primer having an anchor region 5'-(λ)$_n$N$_m$-3' including 5'-(λ)$_1$N$_1$-3' where 5'-(λ)$_1$N$_1$-3' is 5'-AG-3', at least one oligonucleotide primer having an anchor region 5'-(λ)$_n$N$_m$-3' including 5'-(λ)$_1$N$_1$-3' where 5'-(λ)$_1$N$_1$-3' is 5'-CA-3', at least one oligonucleotide primer having an anchor region 5'-(λ)$_n$N$_m$-3' including 5'-(λ)$_1$N$_1$-3' where 5'-(λ)$_1$N$_1$-3' is 5'-CT/U-3' at least one oligonucleotide primer having an anchor region 5'-(λ)$_n$N$_m$-3' including 5'-(λ)$_1$N$_1$-3' where 5'-(λ)$_1$N$_1$-3' is 5'-CC-3', at least one oligonucleotide primer having an anchor region 5'-(λ)$_n$N$_m$-3' including 5'-(λ)$_1$N$_1$-3' where 5'-(λ)$_1$N$_1$-3' is 5'-CG-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UA-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UT/U-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UC-3', and at least one oligonucleotide primer having an anchor region 5'-(λ)$_n$N$_m$-3' including 5'-(λ)$_1$N$_1$-3' where 5'-(λ)$_1$N$_1$-3' is 5'-T/UG-3'. In each case, each of the specified nucleotides of 5'-(λ)$_1$N$_1$-3' can be the specified nucleotides or one or both can be a corresponding nucleotide analog.

Kits are provided according to aspects of the disclosure which include an oligonucleotide primer set including at least 12 or more oligonucleotide primers for use where the complementary elements are "G", i.e. a poly(G) tract, then each oligonucleotide primer set according to aspects of the present disclosure includes at least one oligonucleotide primer having an anchor region 5'-(λ)$_n$N$_m$-3' including 5'-(λ)$_1$N$_1$-3' where 5'-(λ)$_1$N$_1$-3' is 5'-AA-3', at least one oligonucleotide primer having an anchor region 5'-(λ)$_n$N$_m$-3' including 5'-(λ)$_1$N$_1$-3' where 5'-(λ)$_1$N$_1$-3' is 5'-AT/U-3', at least one oligonucleotide primer having an anchor region 5'-(λ)$_n$N$_m$-3' including 5'-(λ)$_1$N$_1$-3' where 5'-(λ)$_1$N$_1$-3' is 5'-AC-3', at least one oligonucleotide primer having an anchor region 5'-(λ)$_n$N$_m$-3' including 5'-(λ)$_1$N$_1$-3' where 5'-(λ)$_1$N$_1$-3' is 5'-AG-3', at least one oligonucleotide primer having an anchor region 5'-(λ)$_n$N$_m$-3' including 5'-(λ)$_1$N$_1$-3' where 5'-(λ)$_1$N$_1$-3' is 5'-GA-3', at least one oligonucleotide primer having an anchor region 5'-(λ)$_n$N$_m$-3' including 5'-(λ)$_1$N$_1$-3' where 5'-(λ)$_1$N$_1$-3' is 5'-GT/U-3' at least one oligonucleotide primer having an anchor region 5'-(λ)$_n$N$_m$-3' including 5'-(λ)$_1$N$_1$-3' where 5'-(λ)$_1$N$_1$-3' is 5'-GC-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UA-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UT/U-3', at least one oligonucleotide primer having an anchor region 5'-(λ)$_n$N$_m$-3' including 5'-(λ)$_1$N$_1$-3' where 5'-(λ)$_1$N$_1$-3' is 5'-CC-3', at least one oligonucleotide primer having an anchor region 5'-(λ)$_n$N$_m$-3' including 5'-(λ)$_1$N$_1$-3' where 5'-(λ)$_1$N$_1$-3' is 5'-CG-3', at least one oligonucleotide primer having an anchor region 5'-(λ)$_n$N$_m$-3' including 5'-(λ)$_1$N$_1$-3' where 5'-(λ)$_1$N$_1$-3' is 5'-GA-3', at least one oligonucleotide primer having an anchor region 5'-(λ)$_n$N$_m$-3' including 5'-(λ)$_1$N$_1$-3' where 5'-(λ)$_1$N$_1$-3' is 5'-GT/U-3' at least one oligonucleotide primer having an anchor region 5'-(λ)$_n$N$_m$-3' including 5'-(λ)$_1$N$_1$-3' where 5'-(λ)$_1$N$_1$-3' is 5'-GC-3', at least one oligonucleotide primer having an anchor region 5'-(λ)$_n$N$_m$-3' including 5'-(λ)$_1$N$_1$-3' where 5'-(λ)$_1$N$_1$-3' is 5'-GG-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UA-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UT/U-3', at least one oligonucleotide primer having an anchor region 5'-(λ)$_n$N$_m$-3' including 5'-(λ)$_1$N$_1$-3' where 5'-(λ)$_1$N$_1$-3' is 5'-T/UC-3', and at least one oligonucleotide primer having an anchor region 5'-(λ)$_n$N$_m$-3' including 5'-(λ)$_1$N$_1$-3' where 5'-(λ)$_1$N$_1$-3' is 5'-T/UG-3'. In each case, each of the specified nucleotides of 5'-(λ)$_1$N$_1$-3' can be the specified nucleotides or one or both can be a corresponding nucleotide analog.

Optionally, a primer tag sequence (PTS) is included in oligonucleotide primers of an oligonucleotide set.

According to aspects of the present disclosure, the oligonucleotide primers of an oligonucleotide primer set are provided in an equimolar mixture. The term "equimolar mixture" as used herein refers to a mixture of primers in which the primers are present in equal molar amounts.

Instructional material for use of the oligonucleotide in methods of generating sequencing libraries from starting input nucleic acid such as RNA or DNA is optionally included in a kit of the disclosure. One or more ancillary reagents such as PCR primers, buffers, enzymes, paramagnetic beads, other types of oligonucleotides, washing solutions, hybridization solutions, detectable labels, detection reagents and the like are also optionally included.

Embodiments of inventive compositions and methods are illustrated in the following examples. These examples are provided for illustrative purposes and are not considered limitations on the scope of inventive compositions and methods.

EXAMPLES

Example 1

The protocol of this example includes two aspects: mRNA fragmentation and library preparation.

In the mRNA fragmentation process of this example (Step A below), oligo(dT)-primed reverse transcription first generates DNA:RNA duplexes from poly(A)-tailed RNA species in the sample. Next, an attenuated RNase H reaction specifically fragments RNA molecules that are complexed with cDNA. The mRNA fragments generated by RNase H feature a 5'-monophosphate and a 3'-hydroxyl, which allows them to be ligated and polyadenylated in the following steps along with miRNAs and other small RNAs.

In the library preparation process of this example (Steps B to F below), mRNA fragments and small RNAs resulting from step A are first 3'-polyadenylated and then NEXTFLEX® Combo-Seq™ 5' 4N adapters featuring bias-reducing randomized ends are ligated to the 5' ends of the polyadenylated RNA. First strand synthesis is then performed using an oligonucleotide primer of the present disclosure, optionally with an overhanging PTS sequence. PCR amplification is then used to amplify the first-strand synthesis product and to add sequences necessary for Illumina® sequencing.

Step A: Reverse Transcription & RNase H Digestion of mRNA

In this example, 5 ng of MCF7 total RNA (ordered from Biochain R1255830-50) was used as RNA to be sequenced.

For each sample, the following reagents were combined on ice in nuclease-free PCR strip tubes:

x μL RNA
y μL Nuclease-free Water
2 μL RT/RNase H Annealing Buffer
2 μL NEXTFLEX® Anchored Oligo(dT) Primer: 5' TTTTTTTTTTTTTTTTTTTTVN 3' (SEQ ID NO:16)
where x+y+4=15 μL TOTAL In a clean microcentrifuge tube, the RT1 Master Mix was prepared on ice using the following volumes per reaction plus a 10% overage: 4.8 μL RT/RNase H Reaction Buffer+1.2 L NEXTFLEX® Combo-Seq™ Reverse Transcriptase=6 μL RT1 Master Mix per intermediate aliquot. For each reaction, 6 μL RT1 Master Mix was pre-aliquoted into adjacent wells of an "intermediate" PCR strip and brought to room temperature.

A thermal cycler was programmed as follows:
3 min 70° C.
Pause1 50° C.
30 min 50° C.
Pause2 74° C.
15 min 74° C.
HOLD 4° C.

The sample tubes were placed in the thermal cycler, the heated lid was then closed and the thermal cycler program was started.

Once the thermal cycler finished ramping down from 70° C. to 50° C. to Pause1, a multichannel pipette was used to add 5 μL room temperature RT1 Master Mix to each sample.

Then a multichannel pipette set to 13 μL was used to mix thoroughly by pipetting up and down 6 times. The samples were not removed from the thermal cycler during this step. The heated lid was then closed and the reaction was incubated at 50° C. for 30 min.

For each sample, 5 μL Thermostable RNase H was pre-aliquoted into adjacent wells of an "intermediate" PCR strip and brought to room temperature.

Once the thermal cycler finished ramping up from 50° C. to 74° C. to Pause2, a multichannel pipette was used to add 4 μL Thermostable RNase H to each sample. Then a multichannel pipette set to 16 μL was used to mix thoroughly by pipetting up and down 6 times. The samples were not removed from the thermal cycler during this step. The heated lid was then closed and the reaction was incubated at 74° C. for 15 min.

Once the thermal cycler ramped down to 4° C., the samples were transferred to a nuclease-free 96-well PCR plate. Then, 20 μL of NEXTFLEX® Cleanup Beads (magnetic) was to each sample and mixed thoroughly by pipetting. 60 μL isopropanol was added and mixed thoroughly by pipetting. The mixtures were then incubated for 5 minutes. The resulting samples were magnetized for 5 minutes or until solution was clear. The supernatant was then removed and discarded. 200 μL of freshly prepared 80% ethanol was added, incubated for 30 seconds, and then the supernatant was removed. This step was repeated for a total of 2 ethanol washes. Freshly prepared 80% ethanol was used and the bead pellet was not incubated with 80% ethanol for extended periods. The samples were incubated for 3 minutes. After one minute, all residual liquid that may have collected at the bottom of the wells was removed. The plate was removed from the magnetic stand and magnetic bead pellets were resuspended in 12 μL Nuclease-free Water by pipetting volume up and down. The samples were then incubated for 2 minutes. The resulting samples were magnetized for 3 minutes or until solution was clear.

10 μL of supernatant containing the Digested RNA product was then transferred to a new PCR strip.

Step B: Polyadenylation

For each sample, the following reagents were combined on ice in nuclease-free PCR strip tubes:

10 μL Digested RNA (product from Step A)+4 μL NEXTFLEX® PAP Buffer+1 μL NEXTFLEX® Poly(A) Polymerase=15 μL total volume.

The samples were incubated in a thermal cycler as follows:
15 min 37° C.
20 min 90° C.
<5 min 4° C.

After thermal cycling finished, the samples were transferred to a nuclease-free 96-well PCR plate.

20 μL of NEXTFLEX® Cleanup Beads (magnetic) was added to each sample and mixed thoroughly by pipetting. 60 μL isopropanol was added and mixed thoroughly by pipetting. The mixtures were then incubated for 5 minutes. Then, the samples were magnetized for 5 minutes or until solution was clear. The supernatant was removed and discarded. 200 μL of freshly prepared 80% ethanol was added, then the samples were incubated for 30 seconds, followed by removal of all of the supernatant. This step was repeated for a total of 2 ethanol washes. Freshly prepared 80% ethanol was used and the bead pellet was not incubated with 80% ethanol for extended periods. The samples were then incubated for 3 minutes. After one minute, all residual liquid that may have collected at the bottom of the wells was removed. The plate was removed from the magnetic stand and the magnetic bead pellets were resuspended in 17 μL Nuclease-free Water by pipetting up and down. The samples were then incubated for 2 minutes. The samples were then magnetized for 3 minutes and or until the solution appeared clear.

15 μL of supernatant containing the Polyadenylated RNA product from each sample was transferred to a new PCR strip.

Step C: NEXTFLEX® 5' 4N Adapter Ligation.

For each sample, the following reagents were combined on ice in nuclease-free PCR strip tubes:

15 µL Polyadenylated RNA (product from Step B)+1.5 µL NEXTFLEX® Combo-Seq™ 5' 4N Adapter (3'ddNVTTTTTTTTTT5'-5'rGrUrUrCrArGrArGrUrUrCrUrArCrArGrUrCrCrGrArGrArUr-CrNrNrNrN3') (SEQ ID NO:17)+6.5 µL NEXTFLEX® Combo-Seq™ 5' Ligation Buffer+2 µL NEXTFLEX® 5'

Ligation Enzyme Mix=25 µL TOTAL

The samples were then mixed thoroughly by pipetting. The samples were then incubated as follows in a thermal cycler with heated lid turned off or left open:

60 min 20° C.
HOLD 4° C.

The product is polyadenylated and 5'-ligated RNA.

Step D: First Strand Synthesis

The RT2 Master Mix was prepared in a clean microcentrifuge tube on ice using the following volumes per reaction plus a 10% overage: 14.3 µL Reverse Transcriptase buffer (RT Buffer) including one of the oligonucleotide primer sets disclosed in Table III (at a molar concentration equal to that used for the 20T RT primer and with all other buffer components unchanged)+2.2 µL NEXTFLEX® Combo-Seq™ Reverse Transcriptase=16.5 µL RT2 Master Mix per intermediate aliquot.

For each reaction, 16.5 µL RT2 Master Mix was prealiqoted into adjacent wells of an "intermediate" PCR strip and bring to room temperature.

A thermal cycler was programmed as follows:

2 min 70° C.
Pause 50° C.
30 min 50° C.
5 min 90° C.
HOLD 4° C.

The thermal cycler program is then started with the polyadenylated and 5'-ligated RNA from Step C in the thermal cycler and the heated lid closed.

Once the thermal cycler has finished ramping down from 70° C. to 50° C., a multichannel pipette is used to add 15 µL room temperature RT2 Master Mix to each 25 µL reaction during the pause. A multichannel pipette set to 30 µL was used to mix thoroughly by pipetting up and down 8 times without removing the samples from the thermal cycler. The heated lid was then closed and the reaction was incubated at 50° C. for 30 min, then 90° C. for 5 min.

Once the thermal cycler ramped down to 4° C., the samples were transferred to a nuclease-free 96-well PCR plate. 40 µL of Adapter Depletion Solution was added to each sample and mixed thoroughly by pipetting. 40 µL of NEXTFLEX® Cleanup Beads (magnetic) was added to each sample and mixed thoroughly by pipetting. Then, 90 µL isopropanol was added to each sample and mixed thoroughly by pipetting. The samples were then incubated for 5 minutes. The samples were then magnetized for 6 minutes or until the solution was clear. The supernatant was removed and discarded. 200 µL of freshly prepared 80% ethanol was added and incubated for 30 seconds, followed by removal of the supernatant. This step was repeated for a total of 2 ethanol washes. Freshly prepared 80% ethanol was used and the bead pellet was not incubated with 80% ethanol for extended periods. The samples were incubated for 3 minutes. After one minute, all residual liquid that may have collected at the bottom of the wells was removed. The plate was removed from the magnetic stand and the bead pellet was resuspended in 20 µL Nuclease-free Water by pipetting volume up and down. The samples were then incubated for 2 minutes. The samples were magnetized for 3 minutes and the solution was clear. The product is Purified First Strand Synthesis Product. 18 µL of supernatant containing Purified First Strand Synthesis Product was then transferred to a new well.

Step E: PCR Amplification

For each sample, the following reagents were combined on ice in nuclease-free PCR strip tubes:

18 µL Purified First Strand Synthesis Product (from Step D)+2 µL NEXTFLEX® UDI Barcoded Primer Mix (e.g. 5'CAAGCAGAAGACGGCATACGAGAT (XXXXXXXX1)GTGACTGGAGTTCCTTGGCAC CCGAGAATTCCA 3' (SEQ ID NO:18) (where (XXXXXXXX1) is the reverse complement of the i7 index sequence) or 5'AATGATACGGCGACCACCGAGATCTA-CAC(XXXXXXXX2)ACACGTTCAGAGTTCT ACAGTCCGAv 3' (SEQ ID NO: 19) (where (XXXXXXXX2) is the i5 index sequence)+5 µL NEXTFLEX® PCR Master Mix=25 µL TOTAL. i7 and i5 index sequences are exemplified in Table II.

TABLE II

| UDI primer # | I7 Index | I5 Index |
|---|---|---|
| UDI 1 | AAGATCAT | AATAATAG |
| UDI 2 | TGCTATTC | TTAGTAGC |
| UDI 3 | GACGTGTC | TGCGTGGC |
| UDI 4 | CGGTAGTC | ACCAATTG |
| UDI 5 | GACAGCAG | CTACTGGT |
| UDI 6 | CTTGTACA | AGCAGAGT |
| UDI 7 | GACAAGTG | CATTATCG |
| UDI 8 | CTCGCCTT | GTGCAGTC |
| UDI 9 | GAGCGTCA | GTTCACAC |
| UDI 10 | CGCGCTCG | CCGCATAC |
| UDI 11 | GAGCTCTA | GTGGCGAA |
| UDI 12 | CTATAGGA | GTGGATAC |
| UDI 13 | AAGAGAGC | AATATAAC |
| UDI 14 | TTATAGCG | TTCTAGGT |
| UDI 15 | GAGCTAAG | AGATTGTG |
| UDI 16 | CGAAGCCA | CAATCCGT |
| UDI 17 | TTGTGGCT | TTACTTAC |
| UDI 18 | CGCGAGAC | TTGTCGAC |
| UDI 19 | GAGATCGG | AAGGAGCG |
| UDI 20 | CGCACTTA | CTCGAAGC |
| UDI 21 | GATGTCAG | GTTAGAAC |
| UDI 22 | CTACTTCG | CGAACTGT |
| UDI 23 | GATTACTC | CATGTCTC |
| UDI 24 | ACTCAGAC | CGACTATA |
| UDI 25 | AAGAGTTG | AATATTGA |

TABLE II-continued

| UDI primer # | I7 Index | I5 Index |
|---|---|---|
| UDI 26 | TTATACAA | TTCTCAAT |
| UDI 27 | GATTAGGA | GTGGAACG |
| UDI 28 | CTCTGGCG | AGTTACGG |
| UDI 29 | GATACCTA | GCGAGATC |
| UDI 30 | CGCGTATC | AGCGTACG |
| UDI 31 | GATACGAT | CTTGGTAC |
| UDI 32 | CTGGAGCT | CGCAGCTG |
| UDI 33 | GAACGATA | ACGGCACA |
| UDI 34 | CGGTCCAT | GCGGTGTG |
| UDI 35 | GAACTGGC | CGATACTA |
| UDI 36 | CGGTGAGA | CAGCTACA |
| UDI 37 | AAGACATA | AATATGCT |
| UDI 38 | TTATGTAT | TTCTCCGC |
| UDI 39 | GAACAGAT | CTATATTG |
| UDI 40 | CTTGGCCT | CAGGAAGG |
| UDI 41 | GAACATTC | GCCGTGCA |
| UDI 42 | CTGATATA | GAGTTGCG |
| UDI 43 | GAAGCGAG | AACCTCAC |
| UDI 44 | CGGCCTCT | AACCATGG |
| UDI 45 | GAAGTCGA | TCACTGTT |
| UDI 46 | CGGCCATG | GACTGAGC |
| UDI 47 | GAAGTTAC | GTCCAAGT |
| UDI 48 | CTTAGAGA | CCGATGCG |

These mixtures were then incubated as follows in a thermal cycler:
a) 30 sec 98° C.
b) 10 sec 98° C.
c) 20 sec 65° C.
d) 15 sec 72° C.
e) 2 min 72° C.
f) HOLD 4° C.
Steps b), c), and d) were repeated for a 16 cycles and amplification products were formed.

Step F: Size Selection & Cleanup

Samples including the amplification products from Step E were transferred to a nuclease-free 96-well PCR plate. If sample volume was less than 25 µL, Nuclease-free Water was added to bring the entire volume up to 25 µL. To each sample, 22.5 µL of NEXTFLEX® Cleanup Beads were added and mixed thoroughly by pipetting. The bead mixture was incubated for 5 minutes. The samples were then magnetized for 5 minutes or until the solution was clear. 42.5 µL of supernatant was transferred to a new well. The plate was removed from the magnetic stand. 20 L NEXTFLEX® Cleanup Beads (magnetic) was then added to each sample and mixed thoroughly by pipetting. The bead mixture was incubated for 5 minutes. The samples were then magnetized for 5 minutes or until the solution was clear. The supernatants were then removed and discarded. 200 µL of freshly prepared 80% ethanol was added, the mixtures incubated for 30 seconds, and then all of the supernatant was removed. This step was repeated for a total of 2 ethanol washes. Freshly prepared 80% ethanol was used and the bead pellet was not incubated with 80% ethanol for extended periods. The samples were incubated for 3 minutes. After one minute, all residual liquid that may have collected at the bottom of the well was removed. The plate was removed from the magnetic stand and the bead pellet was resuspended in 14 µL Resuspension Buffer by pipetting volume up and down. The samples were incubated for 2 minutes. The samples were magnetized for 3 minutes or until solution appeared clear. Then, 12 µL of supernatant, containing the sequencing library was transferred to a new well or clean microcentrifuge tube.

The size distribution of the sequencing library can be checked using the LabChip® GX Touch™ HT instrument (PerkinElmer®) or similar.

Example 2

Synthetic Experimental Nucleic Acid Libraries: Experimental Design

The inventors hypothesized that a sufficiently long poly (A) tract in R1 ("Read 1") would cause both low i7 index quality and the inability to (practically) sequence R2 ("Read 2") and/or low R2 quality. This hypothesis was tested by amplifying oligonucleotides containing homopolymer tracts of defined lengths to generate "synthetic" libraries with poly(A) tracts of defined lengths, as described below.

For this procedure, DNA oligonucleotides having sequences of the following form were synthesized, where $(T)_n$, which refers to the number of consecutive T's, varies between each oligonucleotide.

(SEQ ID NO: 20)
5'TCCTTGGCACCCGAGAATTCCA(T)nVNNNNNNNNNNNNNNNNNNNN NNNGATCGTCGGACTGTAGAACTCTGAAC 3'

The general formula for the oligonucleotide used (i.e. SEQ ID NO:20) represents an equimolar mixture of oligonucleotides used where V was A, G, or C, and where N was A, G, C, or T (or U).

A 25 µL volume of each oligonucleotide of varying $(T)_n$ at a concentration of ~10 pM was amplified via 11 cycles of PCR, in duplicate, using the following index primers, where each library generated would contain a unique i7 and i5 index:

(SEQ ID NO: 21)
5'CAAGCAGAAGACGGCATACGAGAT<u>XXXXXXXX</u>$_1$GTGACTGGAGTTCCT TGGCACCCGAGAATTCCA 3'

(SEQ ID NO: 22)
5'AATGATACGGCGACCACCGAGATCTACAC<u>XXXXXXXX</u>$_2$ACACGTTCA GAGTTCTACAGTCCGA 3' where <u>XXXXXXXX</u>$_1$ represents the reverse complement sequence of the 8-nt i7 index sequence and <u>XXXXXXXX</u>$_2$ represents the sequence of the 8-nt i5 index, respectively. Examples of i7 and i5 index sequence pairs are shown in Table II.

This strategy effectively generated sequencing libraries having the following structure:

(SEQ ID NO: 23)
5'AATGATACGGCGACCACCGAGATCTACAC[i5]ACACGTTCAGAGTT
CTACAGTCCGACGATCNNNNNNNNNNNNNNNNNNNNNNNNNB(A)nTGGAA
TTCTCGGGTGCCAAGGAACTCCAGTCAC[i7]ATCTCGTATGCCGTCTT
CTGCTTG 3' such that for R1, the sequencer would read 23 N's, 1 B, then a poly(A) run of a certain length, depending on $(A)_n$. "B" in this sequence is the IUB (International Union of Biochemistry) code for G, C, T (or U). "N" in this sequence is the IUB code for A, C, G, T/U. The general formula for the oligonucleotide used (i.e. SEQ ID NO:23) represents an equimolar mixture of oligonucleotides used where B was T (or U), G, or C, and where N was A, G, C, or T (or U).

Figure 2:
FIG. 2 is a graph showing that longer poly(A) runs in a target nucleic acid cause a decrease in index quality, here i7 quality, an effect that was detected with 15A and 20A configurations.

Libraries with 0, 5, 10, 15, and 20 A's, with each condition in duplicate, were sequenced on an Illumina® MiSeq®. The sequencing run: R1=150 cycles, i7=12 cycles Following the sequencing run, the median predicted % correct sequences of the i7 index, based on the phred scores, using a computer-implemented script was determined. Next, the % of index reads that match the expected barcode sequence was determined, when one mismatch is allowed during demultiplexing. The results showed that longer poly (A) runs cause a decrease in i7 quality, an effect that was detected with 15A and 20A configurations, see FIGS. 1 and 2.

In a second experiment, libraries with 10, 11, 12, 13, 14, 15, and 20 A's, with each condition in duplicate, were sequenced on an Illumina® MiSeq®. The sequencing run: R1=150 cycles, i7=12 cycles.

Figure 3:
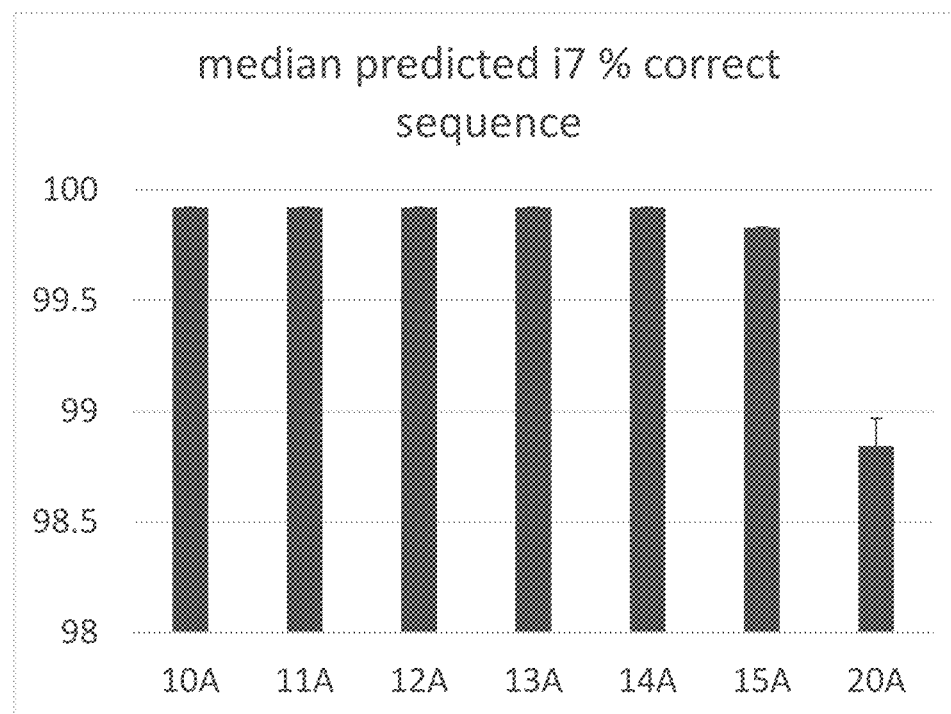
FIG. 3 is a graph showing that longer poly(A) runs cause a decrease in index quality, here i7 quality, an effect that was detected with 12A, 13A, 14A, 15A, and 20A configurations.
Figure 4:
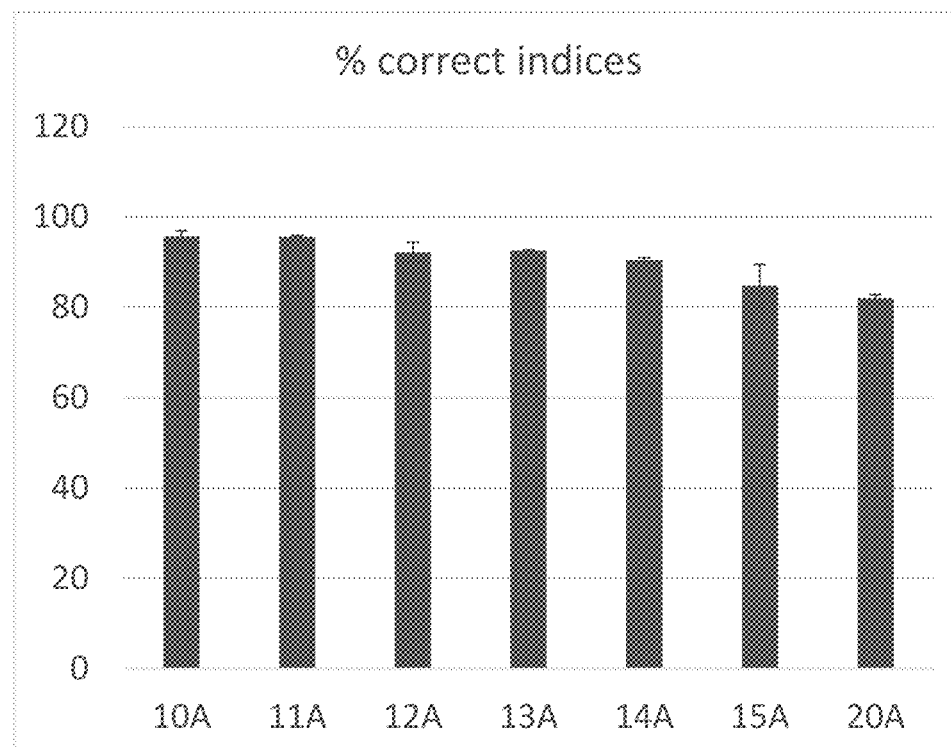
FIG. 4 is a graph showing that longer poly(A) runs cause a decrease in index quality, here i7 quality, an effect that was detected with 12A, 13A, 14A, 15A, and 20A configurations.

Following the sequencing run, the median predicted % correct sequences of the i7 index, based on the phred scores, using a computer implemented script was determined. Next, the % of index reads that match the expected barcode sequence was determined, when one mismatch is allowed during demultiplexing. The results showed that longer poly (A) runs cause a decrease in i7 quality, an effect that was detected with 12A, 13A, 14A, 15A, and 20A configurations, see FIGS. 3 and 4.

Figure 5:
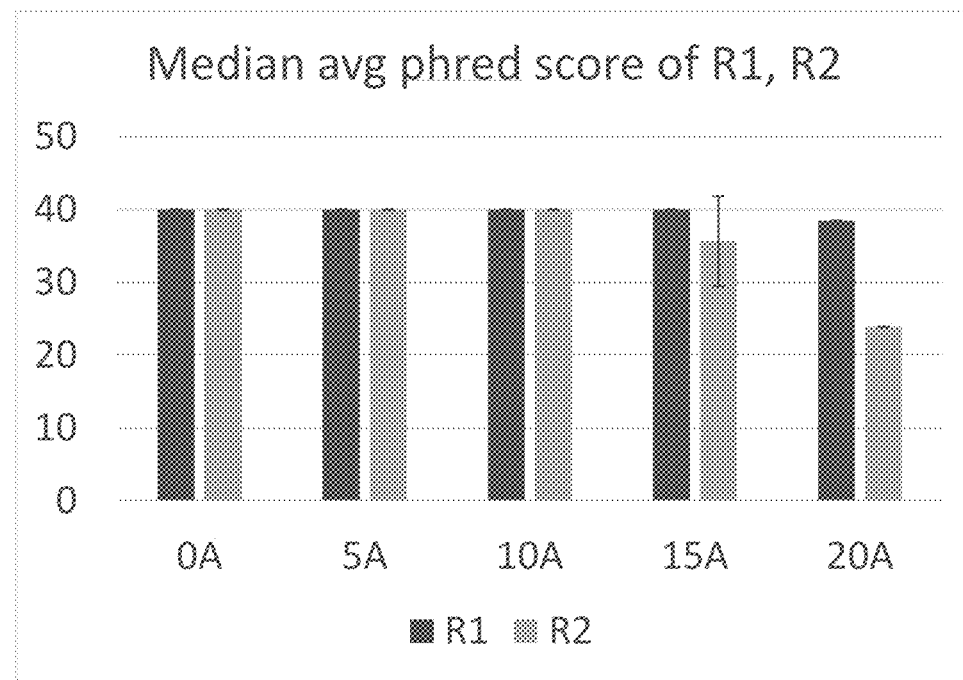
FIG. 5 is a graph showing that longer poly(A) runs cause a decrease in R2 quality, an effect that was detected with 15A and 20A configurations.
Figure 6:
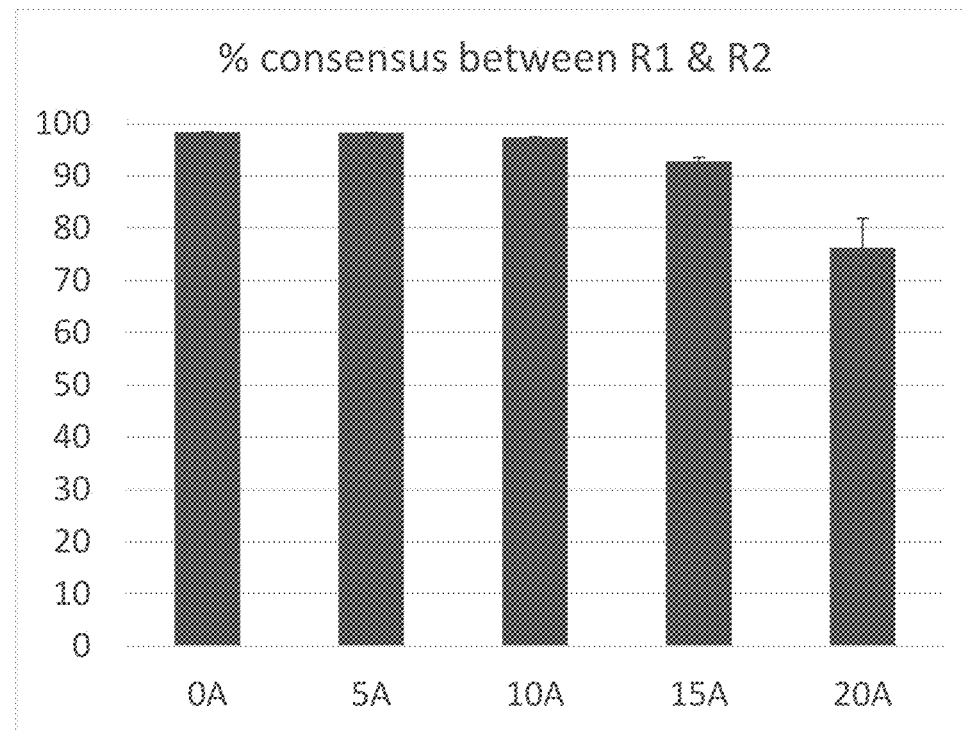
FIG. 6 is a graph showing that longer poly(A) runs cause a decrease in R2 quality, an effect that was detected with 15A and 20A configurations.

In a third experiment, libraries with 0, 5, 10, 15, and 20 A's, with each condition in duplicate, were sequenced on an Illumina® MiSeq®, along with other assorted libraries. The sequencing run: R1=75 cycles, R2=75 cycles, i7=8 cycles Following the sequencing run, the median average phred quality of R1 and R2 was determined using a computer-implemented script examining only the first 20 bases for R1 and the first 20 bases following the poly(T) tract for R2. Next, the % consensus between R1 & R2 using a computer-implemented script was determined. This is a measure of the real-world R2 quality. The results showed that longer poly (A) runs cause a decrease in R2 quality, an effect that was detected with 15A and 20A configurations, see FIGS. 5 and 6.

In a fourth experiment, libraries with 10, 11, 12, 13, 14, 15, and 20 A's, with each condition in duplicate, were sequenced on an Illumina® MiSeq®, along with other assorted libraries. The sequencing run: R1=75 cycles, R2=75 cycles, i7=8 cycles Following the sequencing run, the median average phred quality of R1 and R2 was determined using a computer-implemented script examining only the first 20 bases for R1 and the first 20 bases following the poly(T) tract for R2. Next, the % consensus between R1 & R2 using a computer-implemented script was determined.

Figure 7:
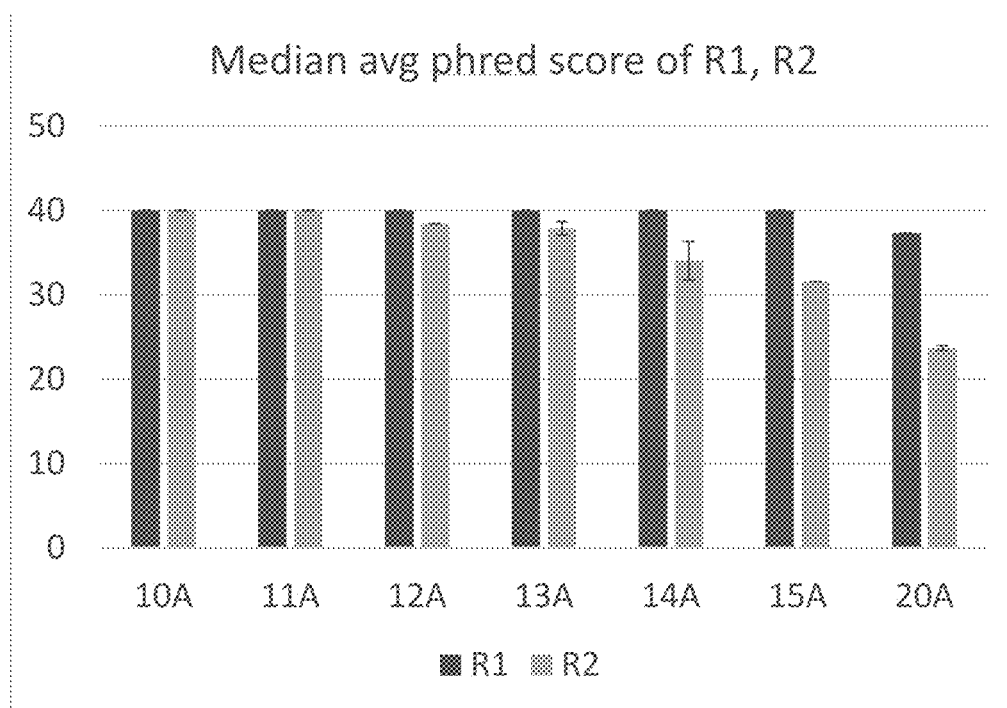
FIG. 7 is a graph showing longer poly(A) runs cause a decrease in R2 quality, an effect that was detected with 12A, 13A, 14A, 15A, and 20A configurations.
Figure 8:
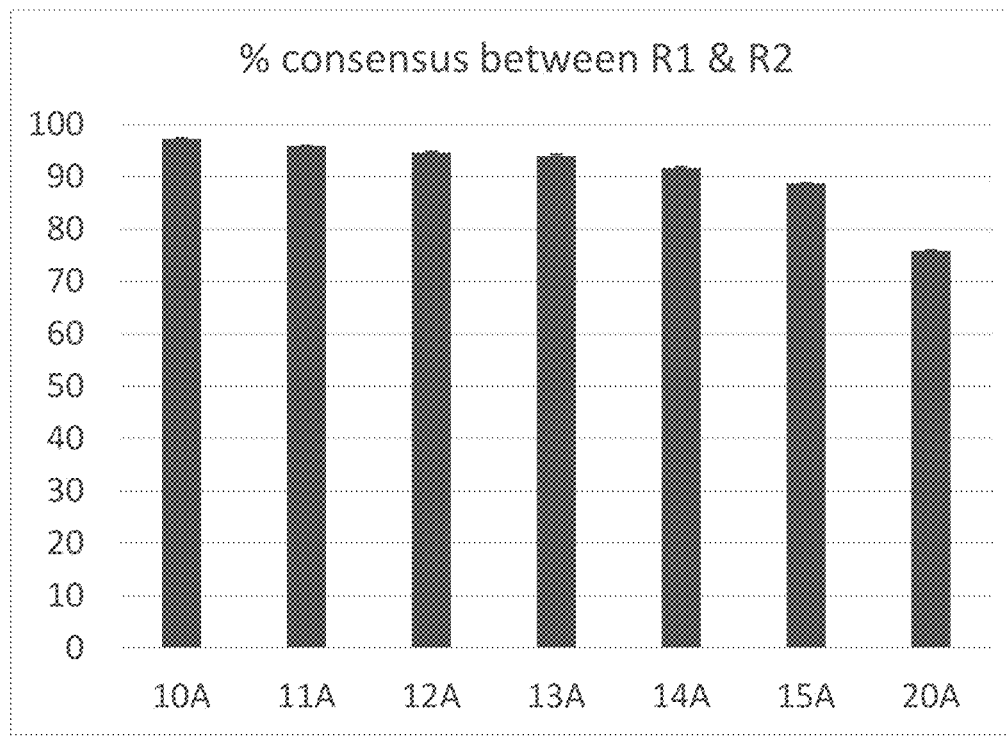
FIG. 8 is a graph showing longer poly(A) runs cause a decrease in R2 quality, an effect that was detected with 12A, 13A, 14A, 15A, and 20A configurations.

The results showed that longer poly(A) runs cause a decrease in R2 quality, an effect that was detected with 12A, 13A, 14A, 15A, and 20A configurations, see FIGS. 7 and 8.

Example 3

Libraries Generated Using Oligonucleotides of the Present Disclosure Compared with Standard Oligonucleotides For this procedure, DNA oligonucleotides were synthesized and tested with the sequences shown in Table III.

TABLE III

| Oligonucleotide Primer Set Name | Sequence | i7 Quality | SEQ ID NO | Successfully Made Library? |
|---|---|---|---|---|
| /X1/(10) VN | 5' PTS-X1X1X1X1X1X1X1X1X1X1VN 3' | GOOD | (SEQ ID NO:24) | YES |
| /X1/(9)TVN | 5' PTS-X1X1X1X1X1X1X1X1X1TVN 3' | GOOD | (SEQ ID NO:25) | YES |
| /X2/(8)TTVN | 5' PTS-X2X2X2X2X2X2X2X2TTVN 3' | GOOD | (SEQ ID NO:26) | YES |
| /X2/(7)TTTVN | 5' PTS-X2X2X2X2X2X2X2TTTVN 3' | GOOD | (SEQ ID NO:27) | YES |
| /X2/(5)T/X2/TTTVN | 5' PTS-X2X2X2X2X2TX2TTTVN 3' | GOOD | (SEQ ID NO:28) | YES |
| /X2/(6)TTTTVN | 5' PTS-X2X2X2X2X2X2TTTTVN 3' | GOOD | (SEQ ID NO:29) | YES |
| /X2/(10)VN | 5' PTS-X2X2X2X2X2X2X2X2X2X2VN 3' | GOOD | (SEQ ID NO:30) | YES |
| /X2/(9)TVN | 5' PTS-X2X2X2X2X2X2X2X2X2TVN 3' | GOOD | (SEQ ID NO:31) | YES |

TABLE III-continued

| Oligonucleotide Primer Set Name | Sequence | i7 Quality | SEQ ID NO | Successfully Made Library? |
|---|---|---|---|---|
| /X2//X2/T(3)TVN | 5' PTS-X2X2TX2X2TX2X2TTVN 3' | GOOD | (SEQ ID NO:32) | YES |
| /X1/(8)TTVN | 5' PTS-X1X1X1X1X1X1X1X1TTVN 3' | GOOD | (SEQ ID NO:33) | YES |
| /X1/(7)TTTVN | 5' PTS-X1X1X1X1X1X1X1TTTVN 3' | GOOD | (SEQ ID NO:34) | YES |
| /X1//X1/T(3)TVN | 5' PTS-X1X1TX1X1TX1X1TTVN 3' | GOOD | (SEQ ID NO:35) | YES |
| 20T | 5' PTS-TTTTTTTTTTTTTTTTTTTVN 3' | BAD | (SEQ ID NO:36) | YES |
| 10T | 5' PTS-TTTTTTTTTVN 3' | N/A | (SEQ ID NO:37) | FAILED |
| /X1/(6)TTTTVN | 5' PTS-X1X1X1X1X1X1TTTTVN 3' | GOOD | (SEQ ID NO:38) | YES |
| /X1/(5)TTTTTVN | 5' PTS-X1X1X1X1X1TTTTTVN 3' | GOOD | (SEQ ID NO:39) | YES |
| /X1/(4)TTTTTTVN | 5' PTS-X1X1X1X1TTTTTTVN 3' | GOOD | (SEQ ID NO:40) | YES |

X1 = 5-hydroxybutynl-2'-deoxyuridine (Super T);
X2 = propynyl-deoxyuridine;
5' PTS used = TCCTTGGCACCCGAGAATTCCA (SEQ ID NO: 41); in these sequences, V is A, G, or C; N is A, G, C, or T(or U). Each "Oligonucleotide Primer Set" used included all 12 variations defined by the formula shown in equimolar proportions, e.g. for X1(10)VN, the "Oligonucleotide Primer Set" includes X1(10)AA, X1(10)AT, X1(10)AC, X1(10)AG, X1(10)CA, X1(10)CT, X1(10)CC, X1(10)CG, X1(10)GA, X1(10)GT, X1(10)GC, and X1(10)GG, in equimolar proportions.

Combo-Seq™ libraries were prepared according to the method of Example 1, using 5 ng MCF7 total RNA (ordered from Biochain R1255830-50) per prep. A different oligonucleotide primer according to the present disclosure (contained in NEXTFLEX® Combo-Seq™ RT Buffer) was used for each test, see Table III for specific oligonucleotide primers used. Each test was prepared in duplicate. Libraries were sequenced on an Illumina® MiSeq®. The % of index reads that match the expected barcode sequence was determined, when one mismatch is allowed during demultiplexing. The quality of the i7 index read was said to be "GOOD" if >=95% of index reads matched the correct index sequence, or "BAD" if <95% of index reads matched the correct index sequence. The 10T formulation failed to generate a library at all, indicating that a poly(A)-hybridizing region composed of 10 T's is insufficient to form library under the described conditions. As shown in Table III, libraries constructed using oligonucleotides of the present disclosure show improved i7 read quality compared to an oligonucleotide in which the poly(A)-hybridizing region consists of 20 T's.

Example 4

Figure 9:
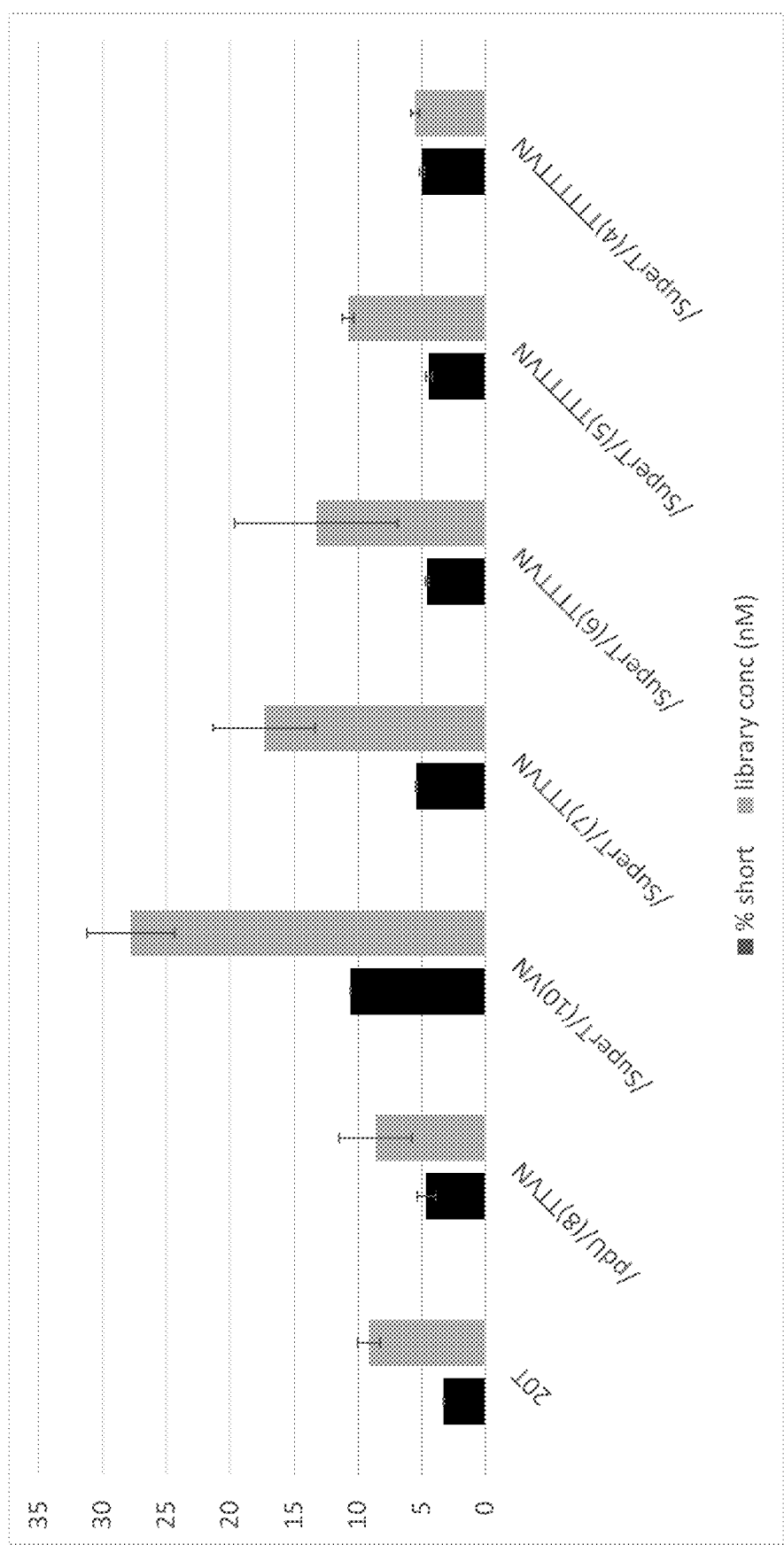
FIG. 9 is a graph showing results of library production by a method including first strand synthesis performed using the indicated oligonucleotide primers of the present disclosure where final library yields in nM are shown compared with the % short as defined in Example 4.

Combo-Seq™ libraries were prepared from 5 ng MCF7 total RNA (ordered from Biochain R1255830-50) according to the procedure of Example 1. A different oligonucleotide primer according to the present disclosure (contained in NEXTFLEX® Combo-Seq™ RT Buffer) was used for each test, see FIG. 9 for specific oligonucleotide primers used.

Each test was prepared in duplicate. Final library yields in nM were calculated using Agilent Bioanalyzer (to determine average size) and Qubit (to determine ng/uL). Libraries were sequenced on an Illumina® MiSeq®. "% short" was calculated as follows:

$$\% \text{ short} = 100 \times \frac{\text{the proportion of reads with inserts in the range}[10, 14]}{\text{the proportion of reads with inserts in the range}[10, 57]}$$

All oligonucleotide primers tested produced libraries which exhibited good i7 read quality. The different oligonucleotide primers produced libraries which varied in yield and size distribution. Regarding size distribution, in Combo-Seq™ libraries, a certain amount of inserts in the sequencing library, most of which correspond to fragmented mRNA, will be less than 15 bases in length. These short fragments are not desired, since they are much less likely than longer fragments to map uniquely to the transcriptome. The /X1/(10)VN formulation had an unacceptably high "% short" for this purpose; /X1/(9)VN and /X1/(8)TVN were also tested and also had an unacceptably high "% short" for this purpose. The /X1/(7)TTTVN, /X1/(6)TTTTVN, /X1/(5)TTTTTVN, and /X1/(4)TTTTTTVN formulations all produce libraries with acceptable "% short" for this purpose. X1 (Super T) is 5-hydroxybutynl-2'-deoxyuridine.

Standard IUPAC nucleotide codes are used herein as shown in Table IV.

TABLE IV

| Symbol | Description | \multicolumn{4}{c|}{Bases represented} | Complement |
|---|---|---|---|---|---|---|
| | | A | C | G | T/U | |
| A | Adenine | A | | | | T |
| C | Cytosine | | C | | | G |
| G | Guanine | | | G | | C |
| T | Thymine | | | | T | A |
| U | Uracil | | | | U | A |
| W | Weak | A | | | T | W |
| S | Strong | | C | G | | S |
| M | aMino | A | C | | | K |
| K | Keto | | | G | T | M |
| R | puRine | A | | G | | Y |
| Y | pYrimidine | | C | | T | R |
| B | not A | | C | G | T | V |
| D | not C | A | | G | T | H |
| H | not G | A | C | | T | D |
| V | not T | A | C | G | | B |
| N | any Nucleotide (not a gap) | A | C | G | T/U | N |

Items

Item 1. An oligonucleotide primer, comprising, from 5' to 3', a homopolymer-hybridizing region, and an anchor region comprising 5'-($\lambda$)$_n$N$_m$-3', where n is an integer in the range of 1 to 20, or greater, and m is an integer in the range of 1-10, or greater, wherein the homopolymer-hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer-hybridizing region hybridizes to a complementary homopolymer tract of a target nucleic acid, wherein the complementary homopolymer tract comprises a contiguous sequence of complementary elements, wherein $\lambda$ is any nucleotide or nucleotide analog with the proviso that $\lambda$ is not a nucleotide or nucleotide analog complementary to a complementary element of the complementary homopolymer tract, and wherein N is any nucleotide or nucleotide analog.

Item 2. The oligonucleotide primer of item 1, comprising, from 5' to 3', a poly(A) homopolymer-hybridizing region, and the anchor region comprising 5'-($\lambda$)$_n$N$_m$-3', where n is an integer in the range of 1 to 20, or greater, and m is an integer in the range of 1-10, or greater, wherein the poly(A) homopolymer-hybridizing region is a contiguous sequence of 5 to 20 elements, wherein the elements are nucleotides or $T_m$ increasing nucleotide analogs, wherein the poly(A) homopolymer-hybridizing region hybridizes to a poly(A) homopolymer tract of a target nucleic acid, wherein at least 4 of the elements are $T_m$ increasing nucleotide analogs, wherein $\lambda$ is any nucleotide or nucleotide analog with the proviso that $\lambda$ is not a nucleotide or nucleotide analog complementary to a residue of the poly(A) homopolymer tract, and wherein N is any nucleotide or nucleotide analog.

Item 3. The oligonucleotide primer of item 1, comprising, from 5' to 3', a poly(U) homopolymer-hybridizing region, and the anchor region comprising 5'-($\lambda$)$_n$N$_m$-3', where n is an integer in the range of 1 to 20, or greater, and m is an integer in the range of 1-10, or greater, wherein the poly(U) homopolymer-hybridizing region is a contiguous sequence of 5 to 20 elements, wherein the elements are nucleotides or $T_m$ increasing nucleotide analogs, wherein the poly(U) homopolymer-hybridizing region hybridizes to a poly(U) homopolymer tract of a target nucleic acid, wherein at least 4 of the elements are $T_m$ increasing nucleotide analogs, wherein $\lambda$ is any nucleotide or nucleotide analog with the proviso that $\lambda$ is not a nucleotide or nucleotide analog complementary to a residue of the poly(U) homopolymer tract, and wherein N is any nucleotide or nucleotide analog.

Item 4. The oligonucleotide primer of item 1, comprising, from 5' to 3', a poly(G) homopolymer-hybridizing region, and the anchor region comprising 5'-($\lambda$)$_n$N$_m$-3', where n is an integer in the range of 1 to 20, or greater, and m is an integer in the range of 1-10, or greater, wherein the poly(G) homopolymer-hybridizing region is a contiguous sequence of 5 to 20 elements, wherein the elements are nucleotides or $T_m$ increasing nucleotide analogs, wherein the homopolymer-hybridizing region hybridizes to a poly(G) homopolymer tract of a target nucleic acid, wherein at least 4 of the elements are $T_m$ increasing nucleotide analogs, wherein $\lambda$ is any nucleotide or nucleotide analog with the proviso that $\lambda$ is not a nucleotide or nucleotide analog complementary to a residue of the poly(G) homopolymer tract, and wherein N is any nucleotide or nucleotide analog.

Item 5. The oligonucleotide primer of item 1, comprising, from 5' to 3', a poly(C)-homopolymer-hybridizing region, and the anchor region comprising 5'-($\lambda$)$_n$N$_m$-3', where n is an integer in the range of 1 to 20, or greater, and m is an integer in the range of 1-10, or greater, wherein the poly(C) homopolymer-hybridizing region is a contiguous sequence of 5 to 20 elements, wherein the elements are nucleotides or $T_m$ increasing nucleotide analogs, wherein the homopolymer-hybridizing region hybridizes to a poly(C) homopolymer tract of a target nucleic acid, wherein at least 4 of the elements are $T_m$ increasing nucleotide analogs, wherein $\lambda$ is any nucleotide or nucleotide analog with the proviso that $\lambda$ is not a nucleotide or nucleotide analog complementary to a residue of the poly(C) homopolymer tract, and wherein N is any nucleotide or nucleotide analog.

Item 6. The oligonucleotide primer of item 1, comprising, from 5' to 3', a poly(T)-homopolymer-hybridizing region, and the anchor region comprising 5'-($\lambda$)$_n$N$_m$-3', where n is an integer in the range of 1 to 20, or greater, and m is an integer in the range of 1-10, or greater, wherein the poly(T) homopolymer-hybridizing region is a contiguous sequence of 5 to 20 elements, wherein the elements are nucleotides or $T_m$ increasing nucleotide analogs, wherein the homopolymer-hybridizing region hybridizes to a poly(T) homopolymer tract of a target nucleic acid, wherein at least 4 of the elements are $T_m$ increasing nucleotide analogs, wherein $\lambda$ is any nucleotide or nucleotide analog with the proviso that $\lambda$ is not a nucleotide or nucleotide analog complementary to a residue of the poly(T) homopolymer tract, and wherein N is any nucleotide or nucleotide analog.

Item 7. The oligonucleotide primer of any of items 1 to 6, wherein the $T_m$ increasing nucleotide analogs are independently selected from: a locked nucleic acid, a peptide nucleic acid, a bridged nucleic acid, 5-methyl dC, 2, 6-diaminopurine, propynyl-deoxyuridine and 5-hydroxybutynl-2'-deoxyuridine, and combinations of any two or more thereof.

Item 8. The oligonucleotide primer of any of items 1 to 7, further comprising a 5' primer tag sequence (PTS) covalently bonded to a 5' residue of the homopolymer-hybridizing region.

Item 9. The oligonucleotide primer of any of items 1 to 8, wherein the homopolymer-hybridizing region is a contiguous sequence of 7 to 11 elements, and wherein 5, 6, or 7 of the elements are $T_m$ increasing nucleotide analogs.

Item 10. The oligonucleotide primer of any of items 1 to 9, comprising from 5' to 3', a primer tag sequence, a homopolymer hybridizing region, and an anchor region comprising 5'-($\lambda$)$_n$N$_m$-3', where n is an integer in the range of 1 to 20, or greater, and m is an integer in the range of 1-10, or greater, wherein the homopolymer hybridizing region is a contiguous sequence of 5 to 20 elements, wherein the elements are nucleotides or $T_m$ increasing nucleotide analogs, wherein at least 4 of the elements are $T_m$ increasing nucleotide analogs, wherein the homopolymer hybridizing region hybridizes to a complementary homopolymer tract of a target nucleic acid, wherein the complementary homopolymer tract comprises a contiguous sequence of complementary elements, wherein λ is any nucleotide or nucleotide analog with the proviso that λ is not a nucleotide or nucleotide analog complementary to a complementary element of the complementary homopolymer tract, and wherein N is any nucleotide or nucleotide analog.

Item 11. The oligonucleotide primer of any of items 1 to 10, wherein the homopolymer hybridizing region is a contiguous sequence of 5 to 15 elements.

Item 12. The oligonucleotide primer of item 11, comprising, from 5' to 3', a poly(A) homopolymer-hybridizing region, and the anchor region comprising 5'-(λ)$_n$N$_m$-3', where n is an integer in the range of 1 to 20, or greater, and m is an integer in the range of 1-10, or greater, wherein the poly(A) homopolymer-hybridizing region is a contiguous sequence of 5 to 15 elements, wherein the elements are nucleotides or $T_m$ increasing nucleotide analogs, wherein the poly(A) homopolymer-hybridizing region hybridizes to a poly(A) homopolymer tract of a target nucleic acid, wherein at least 4 of the elements are $T_m$ increasing nucleotide analogs, wherein λ is any nucleotide or nucleotide analog with the proviso that λ is not a nucleotide or nucleotide analog complementary to a residue of the poly(A) homopolymer tract, and wherein N is any nucleotide or nucleotide analog.

Item 13. The oligonucleotide primer of item 11, comprising, from 5' to 3', the primer tag sequence (PTS), the poly(A) homopolymer-hybridizing region, and the anchor region comprising 5'-(λ)$_n$N$_m$-3', where n is an integer in the range of 1 to 20, or greater, and m is an integer in the range of 1-10, or greater, wherein the poly(A) homopolymer-hybridizing region is a contiguous sequence of 5 to 15 elements, wherein the elements are nucleotides or $T_m$ increasing nucleotide analogs, wherein the poly(A) homopolymer-hybridizing region hybridizes to the poly(A) homopolymer tract of a target nucleic acid, wherein at least 4 of the elements are $T_m$ increasing nucleotide analogs, wherein λ is any nucleotide or nucleotide analog with the proviso that λ is not a nucleotide or nucleotide analog complementary to a residue of the poly(A) homopolymer tract, and wherein N is any nucleotide or nucleotide analog.

Item 14. An oligonucleotide primer set, comprising two or more oligonucleotide primers according to any of items 1 to 13.

Item 15. The oligonucleotide primer set of item 14, wherein at least two of the two or more oligonucleotide primers have different anchor regions.

Item 16. The oligonucleotide primer set of item 14 or 15, comprising at least 12 or more oligonucleotide primers for use where the complementary elements of the target nucleic acid are "A", wherein the oligonucleotide primer set comprises at least one oligonucleotide primer where 5'-(λ)$_1$N$_1$-3' is 5'-AA-3', at least one oligonucleotide primer where 5'-(λ)$_1$N$_1$-3' is 5'-AT-3', at least one oligonucleotide primer where 5'-(λ)$_1$N$_1$-3' is 5'-AC-3', at least one oligonucleotide primer where 5'-(λ)$_1$N$_1$-3' is 5'-AG-3', at least one oligonucleotide primer where 5'-(λ)$_1$N$_1$-3' is 5'-CA-3', at least one oligonucleotide primer where 5'-(λ)$_1$N$_1$-3' is 5'-CT-3' at least one oligonucleotide primer where 5'-(λ)$_1$N$_1$-3' is 5'-CC-3', at least one oligonucleotide primer where 5'-(λ)$_1$N$_1$-3' is 5'-CG-3', at least one oligonucleotide primer where 5'-(λ)$_1$N$_1$-3' is 5'-GA-3', at least one oligonucleotide primer where 5'-(λ)$_1$N$_1$-3' is 5'-GT-3', at least one oligonucleotide primer where 5'-(λ)$_1$N$_1$-3' is 5'-GC-3', and at least one oligonucleotide primer where 5'-(λ)$_1$N$_1$-3' is 5'-GG-3'.

Item 17. The oligonucleotide primer set of item 14 or 15, comprising at least 12 or more oligonucleotide primers for use where the complementary elements of the target nucleic acid are "C", wherein the oligonucleotide primer set comprises at least one oligonucleotide primer where 5'-(λ)$_1$N$_1$-3' is 5'-AA-3', at least one oligonucleotide primer where 5'-(λ)$_1$N$_1$-3' is 5'-AT-3', at least one oligonucleotide primer where 5'-(λ)$_1$N$_1$-3' is 5'-AC-3', at least one oligonucleotide primer where 5'-(λ)$_1$N$_1$-3' is 5'-AG-3', at least one oligonucleotide primer where 5'-(λ)$_1$N$_1$-3' is 5'-CA-3', at least one oligonucleotide primer where 5'-(λ)$_1$N$_1$-3' is 5'-CT-3' at least one oligonucleotide primer where 5'-(λ)$_1$N$_1$-3' is 5'-CC-3', at least one oligonucleotide primer where 5'-(λ)$_1$N$_1$-3' is 5'-CG-3', at least one oligonucleotide primer where 5'-(λ)$_1$N$_1$-3' is 5'-TA-3', at least one oligonucleotide primer where 5'-(λ)$_1$N$_1$-3' is 5'-TT-3', at least one oligonucleotide primer where 5'-(λ)$_1$N$_1$-3' is 5'-TC-3', and at least one oligonucleotide primer where 5'-(λ)$_1$N$_1$-3' is 5'-TG-3'.

Item 18. The oligonucleotide primer set of item 14 or 15, comprising at least 12 or more oligonucleotide primers for use where the complementary elements of the target nucleic acid are "G", wherein the oligonucleotide primer set comprises at least one oligonucleotide primer where 5'-(λ)$_1$N$_1$-3' is 5'-AA-3', at least one oligonucleotide primer where 5'-(λ)$_1$N$_1$-3' is 5'-AT-3', at least one oligonucleotide primer where 5'-(λ)$_1$N$_1$-3' is 5'-AC-3', at least one oligonucleotide primer where 5'-(λ)$_1$N$_1$-3' is 5'-AG-3', at least one oligonucleotide primer where 5'-(λ)$_1$N$_1$-3' is 5'-GA-3', at least one oligonucleotide primer where 5'-(λ)$_1$N$_1$-3' is 5'-GT-3' at least one oligonucleotide primer where 5'-(λ)$_1$N$_1$-3' is 5'-GC-3', at least one oligonucleotide primer where 5'-(λ)$_1$N$_1$-3' is 5'-GG-3', at least one oligonucleotide primer where 5'-(λ)$_1$N$_1$-3' is 5'-TA-3', at least one oligonucleotide primer where 5'-(λ)$_1$N$_1$-3' is 5'-TT-3', at least one oligonucleotide primer where 5'-(λ)$_1$N$_1$-3' is 5'-TC-3', and at least one oligonucleotide primer where 5'-(λ)$_1$N$_1$-3' is 5'-TG-3'.

Item 19. The oligonucleotide primer set of item 14 or 15, comprising at least 12 or more oligonucleotide primers for use where the complementary elements of the target nucleic acid are "T" or "U", wherein the oligonucleotide primer set comprises at least one oligonucleotide primer where 5'-(λ)$_1$N$_1$-3' is 5'-CA-3', at least one oligonucleotide primer where 5'-(λ)$_1$N$_1$-3' is 5'-CT-3', at least one oligonucleotide primer where 5'-(λ)$_1$N$_1$-3' is 5'-CC-3', at least one oligonucleotide primer where 5'-(λ)$_1$N$_1$-3' is 5'-CG-3', at least one oligonucleotide primer where 5'-(λ)$_1$N$_1$-3' is 5'-GA-3', at least one oligonucleotide primer where 5'-(λ)$_1$N$_1$-3' is 5'-GT-3' at least one oligonucleotide primer where 5'-(λ)$_1$N$_1$-3' is 5'-GC-3', at least one oligonucleotide primer where 5'-(λ)$_1$N$_1$-3' is 5'-GG-3', at least one oligonucleotide primer where 5'-(λ)$_1$N$_1$-3' is 5'-TA-3', at least one oligonucleotide primer where 5'-(λ)$_1$N$_1$-3' is 5'-TT-3', at least one oligonucleotide primer where 5'-(λ)$_1$N$_1$-3' is 5'-TC-3', and at least one oligonucleotide primer where 5'-(λ)$_1$N$_1$-3' is 5'-TG-3'.

Item 20. The oligonucleotide primer set of any of items 14 to 19, wherein the oligonucleotide primers of the primer set are provided in an equimolar mixture.

Item 21. A method of generating a sequencing library, comprising:
providing an oligonucleotide primer or oligonucleotide primer set according to any of items 1 to 20; annealing the oligonucleotide primer or oligonucleotide primer set to target nucleic acid, the target nucleic acid comprising the complementary homopolymer tract having at least 5 to 20 contiguous complementary elements;

and extending the oligonucleotide primer under extension reaction conditions, producing an extension product complementary to at least a portion of the target nucleic acid.

Item 22. The method of item 21, wherein the target nucleic acid is RNA and extending the oligonucleotide primer or primers of the oligonucleotide primer set comprises reverse transcription using a reverse transcriptase to produce a complementary DNA (cDNA).

Item 23. The method of item 21 or 22, further comprising polymerizing a second strand of DNA complementary to the extension product, producing double-stranded nucleic acid.

Item 24. The method of any of items 21 to 23, further comprising amplifying the double-stranded nucleic acid.

Item 25. A kit, comprising an oligonucleotide or oligonucleotide primer set according to any of items 1 to 20.

Item 26. An oligonucleotide primer substantially as shown or described herein.

Item 27. A method of generating a sequencing library, and/or a sequencing library, and/or a method of sequencing the sequencing library, substantially as shown or described herein.

Item 28. A kit substantially as shown or described herein.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. An oligonucleotide primer, comprising, from 5' to 3', a 5' primer tag sequence (PTS) covalently bonded to a 5' residue of a homopolymer-hybridizing region, wherein the PTS consists of a linker and/or one or more nucleic acid sequences useful in nucleic acid sequence manipulation selected from: a sequencing site, a PCR site, and a hybridization site; the homopolymer-hybridizing region, and an anchor region comprising 5'-$(\lambda)_n N_m$-3', wherein the homopolymer-hybridizing region hybridizes to a complementary homopolymer tract of a target nucleic acid, wherein the complementary homopolymer tract comprises a contiguous sequence of complementary elements, wherein the homopolymer-hybridizing region, and the anchor region together have a sequence selected from the group consisting of: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, and SEQ ID NO: 15, and wherein λ is any nucleotide or nucleotide analog with the proviso that k is not a nucleotide or nucleotide analog complementary to a complementary element of the complementary homopolymer tract, and wherein N is any nucleotide or nucleotide analog.

2. An oligonucleotide primer set, comprising two or more oligonucleotide primers according to claim 1.

3. The oligonucleotide primer set of claim 2, wherein at least two of the two or more oligonucleotide primers have different anchor regions.

4. The oligonucleotide primer set of claim 2, comprising at least 12 or more oligonucleotide primers for use where the complementary elements of the target nucleic acid are "A", wherein the oligonucleotide primer set comprises at least one oligonucleotide primer where 5'-$(\lambda)_1 N_1$-3' is 5'-AA-3', at least one oligonucleotide primer where 5'-$(\lambda)_1 N_1$-3' is 5'-AT-3', at least one oligonucleotide primer where 5'-$(\lambda)_1 N_1$-3' is 5'-AC-3', at least one oligonucleotide primer where 5'-$(\lambda)_1 N_1$-3' is 5'-AG-3', at least one oligonucleotide primer where 5'-$(\lambda)_1 N_1$-3' is 5'-CA-3', at least one oligonucleotide primer where 5'-$(\lambda)_1 N_1$-3' is 5'-CT-3' at least one oligonucleotide primer where 5'-$(\lambda)_1 N_1$-3' is 5'-CC-3', at least one oligonucleotide primer where 5'-$(\lambda)_1 N_1$-3' is 5'-CG-3', at least one oligonucleotide primer where 5'-$(\lambda)_1 N_1$-3' is 5'-GA-3', at least one oligonucleotide primer where 5'-$(\lambda)_1 N_1$-3' is 5'-GT-3', at least one oligonucleotide primer where 5'-$(\lambda)_1 N_1$-3' is 5'-GC-3', and at least one oligonucleotide primer where 5'-$(\lambda)_1 N_1$-3' is 5'-GG-3'.

5. The oligonucleotide primer set of claim 2, wherein the oligonucleotide primers of the primer set are provided in an equimolar mixture.

6. A method of generating a sequencing library, comprising:

providing an oligonucleotide primer according to claim 1;

annealing the oligonucleotide primer or oligonucleotide primer set to target nucleic acid, the target nucleic acid comprising the complementary homopolymer tract having at least 5 to 20 contiguous complementary elements;

extending the oligonucleotide primer under extension reaction conditions, producing an extension product complementary to at least a portion of the target nucleic acid;

polymerizing a second strand of DNA complementary to the extension product, producing double-stranded nucleic acid; and amplifying the double-stranded nucleic acid using amplification primers, producing amplicons, thereby introducing one or more primer-derived nucleic acids into the amplicons, the one or more primer-derived nucleic acids comprising at least a sequencing primer binding site sequence.

7. The method of claim 6, wherein the target nucleic acid is RNA and extending the oligonucleotide primer or primers of the oligonucleotide primer set comprises reverse transcription using a reverse transcriptase to produce a complementary DNA (cDNA).

8. A kit, comprising an oligonucleotide according to claim 1.

* * * * *